US007569387B2

(12) United States Patent
Theill et al.

(10) Patent No.: US 7,569,387 B2
(45) Date of Patent: Aug. 4, 2009

(54) ANTIBODY TO TNF RECEPTOR-LIKE MOLECULES

(75) Inventors: Lars Eyde Theill, Thousand Oaks, CA (US); Richard Yeh, Ithaca, NY (US); Scott Michael Silbiger, Woodland Hills, CA (US); Gang Yu, Thousand Oaks, CA (US); Giorgio Senaldi, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 198 days.

(21) Appl. No.: 11/436,207

(22) Filed: May 17, 2006

(65) Prior Publication Data
US 2007/0015219 A1   Jan. 18, 2007

Related U.S. Application Data

(63) Continuation of application No. 09/948,018, filed on Sep. 5, 2001, now Pat. No. 7,153,669.

(60) Provisional application No. 60/230,191, filed on Sep. 5, 2000.

(51) Int. Cl.
*C07K 16/28* (2006.01)
*C12N 5/16* (2006.01)

(52) U.S. Cl. ............... 435/334; 530/388.22; 530/388.1; 530/388.15; 530/387.1; 530/391.5; 530/391.1

(58) Field of Classification Search ........................ None
See application file for complete search history.

(56) References Cited

U.S. PATENT DOCUMENTS

| 5,194,596 | A | * | 3/1993 | Tischer et al. |
| 5,350,836 | A | * | 9/1994 | Kopchick et al. |
| 5,580,756 | A | * | 12/1996 | Linsley et al. |
| 5,843,789 | A | | 12/1998 | Nomura et al. |
| 6,342,351 | B1 | * | 1/2002 | Chen et al. |

FOREIGN PATENT DOCUMENTS

| EP | 393438 | 10/1990 |
| EP | 422339 | 1/1998 |
| WO | WO 01/55206 | 8/2001 |
| WO | WO 01/55314 | 8/2001 |
| WO | WO 01/57182 | 8/2001 |

OTHER PUBLICATIONS

Yount et al., Rat neutrophil defensins, J. immunol. 155:4476-4484, 1995.*
GenBank Accession Q9H665, Transmembrane protein 149 precurson (U2 small nuclear RNA auxiliary factor 1-like 4), Mar. 1, 2001, accessed Jun. 10, 2008.*
Wattanabe et al., Database GenEmbl, Accession No. AK026226, Sep. 29, 2000.*
Lamerdin, Database GenEmbl, Accession No. AD000671, Dec. 10, 1997.*
NCI/CGAP, Database EST, Accession No. AI372981, Feb. 16, 1999.*
NCI/NINDS-CGAP, Database EST, Accession No. AI597639, May 12, 1999.*
Vukicevic et al., 1996, PNAS USA 93:9021-9026.*
Aderka, "The potential biological and clinical significance of the soluble tumor necrosis factor receptors," *Cytokine & Growth Factor Reviews* 7:231-240, 1996.
Banner et al., Crystal structure of the soluble human 55kd TNF receptor-human TNFβ complex: Implications for TNF receptor activation, *Cell* 73:431-445, 1993.
Castro et al., "Fas modulation of apoptosis during negative selection of thymocytes," *Immunity* 5:617-627, 1996.
Chichepotiche et al., "Tweak, a new secreted ligand in the tumor necrosis factor family that weakly induces apoptosis," *J. Biol. Chem.* 272:32401-32410, 1997.
Fu et al., "Development and maturation of secondary lymphoid tissues," *Ann. Rev. Immunol.* 17:399-433, 1999.
Grewal et al., "CD40 and CD154 in cell-mediated immunity," *Ann. Rev. Immunol.* 16:111-135, 1998.
Guo et al., "Stimulatory effects of B7-related protein-1 on cellular and humoral immune responses in mice," *J. Immunol.* 166:5578-5584, 2001.
Hahne et al., "April, a new ligand of the tumor necrosis factor family, stimulates tumor cell growth," *J. Exp. Med.*, 188:1185-1190, 1998.
Han et al., "Molecular cloning of human p38 MAP kinase," *Biochimica et Biophysica Acta* 1265:224-227, 1995.
Idriss et al., "TNFα and the TNF receptor superfamily: Structure-function relationship(s)," *Microsc. Res. Tech.* 50:184-195, 2000.
Lacey et al., "Osteoprotegerin ligand is a cytokine that regulates osteoclast differentiation and activation," *Cell* 93:165-176, 1998.
Lee et al., "A protein kinase involved in the regulation of inflammatory cytokine biosynthesis," *Nature* 372:739-746, 1994.
Locksley et al., "The TNF and TNF receptor superfamilies: integrating mammalian biology," *Cell* 104:487-501, 2001.
Madry et al., "The characterization of murine BCMA gene defines it as a new member of the tumor necrosis factor receptor superfamily," *International Immunology* 10:1693-1702, 1998.
Mauri et al., "LIGHT, a new member of the TNF superfamily, and lymphotoxin α are ligands for herpesvirus entry mediator," *Immunity* 8:21-30, 1998.
Mizushima et al., "pEF-BOS, a powerful mammalian expression vector," *Nucl. Acids Res.* 18:5322, 1990.
Nagata et al., "Fas and Fas ligand: *lpr* and *gld* mutations," *Immunology Today* 16:39-43, 1995.
Naismith et al., "Modularity in the TNF-receptor family," *TIBS Trends Biochem. Sci..* 23:74-79, 1998.
Noelle, "CD40 and its ligand in host defense," *Immunity* 4:415-419, 1996.
Nophar et al., "Soluble forms of tumor necrosis factor receptors (TNF-Rs). The cDNA for the type 1 TNF-R, cloned using amino acid sequence data of its soluble form, encodes both the cell surface and a soluble form of the receptor," *EMBO J.* 9:3269-3278, 1990. 1999.

(Continued)

*Primary Examiner*—Lorraine Spector
*Assistant Examiner*—Claire Kaufman
(74) *Attorney, Agent, or Firm*—Randolph N. Mohr

(57) ABSTRACT

Novel MK61 polypeptides and nucleic acid molecules encoding the same. The invention also provides vectors, host cells, selective binding agents, and methods for producing MK61 polypeptides. Also provided for are methods for the treatment, diagnosis, amelioration, or prevention of diseases with MK61 polypeptides.

15 Claims, 24 Drawing Sheets

OTHER PUBLICATIONS

Shu et al., "TALL-1 is a novel member of the TNF family that is down-regulated by mitogens," *J. Leukocyte Biology* 65:680-683,
Smith et al., "A receptor for tumor necrosis factor defines an unusual family of cellular and viral proteins," *Science* 248:1019-1023, 1990.
Smith et al., "The TNF receptor superfamily of cellular and viral proteins: Activation, costimulation, and death," *Cell* 76:959-962, 1994.
Strasser et al., "FADD/MORTI, a signal transducer that can promote cell death or cell growth," *Intl. J. Biochem. Cell Biol*. 31:533-537, 1997.
Tracey et al., "Tumor Necrosis Factor: A pleiotropic cytokine and therapeutic target," *Ann. Rev. Med*. 45:491-503, 1994.
Wallach et al., "Soluble and cell surface receptors for tumor necrosis factor," *Agents Actions Suppl*. 35:51-57, 1991.
Williams et al., "Cartilage destruction and bone erosion in arthritis: the role of tumour necrosis factor α," *Ann. Rheum. Dis*. 59(suppll):i75-i80, 2000.
Yamada et al., "Initiation of liver growth by tumor necrosis factor: Deficient liver regeneration in mice lacking type I tumor necrosis factor receptor," *Proc. Natl. Acad. Sci. (U.S.A)*. 94:1441-1446, 1997.
International Search Report, PCT/US01/27631, European Patent Office.
Database EMBL Accession No. AI819838, XP002197573, Dec. 23, 1999, the whole document.
Database EMBL Accession No. AI597639, XP002197574, Mar. 4, 2000, the whole document.
Database EMBL Accession No. AI806948, XP002197575, Dec. 22, 1999, the whole document.
Database EMBL Accession No. BE254397, XP002197576, Jul. 14, 2000, the whole document.
Database EMBL Accession No. AI571409, XP002197577, Mar. 4, 2000, the whole document.
Database EMBL Accession No. AI090681, XP002197578, Mar. 3, 2000, the whole document.
Database EMBL Accession No. AW274489, XP002197579, Jan. 6, 2000, the whole document.
Database EMBL Accession No. AW553050, XP002197580, Mar. 13, 2000, the whole document.
Database EMBL Accession No. AK026226, XP002197581, Sep. 29, 2000, "*Homo sapiens* cDNA: FLJ22573 fis, clone HSI02387," the whole document.
Database EMBL Accession No. AAK89843, XP002197582, Aug. 2, 2001, SEQ ID No. 3419 and the whole document.
Database EMBL Accession No. AAK89845, XP002197583, Aug. 2, 2001, SEQ ID No. 3421 and the whole document.
Database EMBL Accession No. ABA07211, XP002197584, Jan. 14, 2002, SEQ ID No. 530 and the whole document.
Database EMBL Accession No. ABA07213, XP002197585, Jan. 14, 2002, SEQ ID No. 532 and the whole document.
Database EMBL Accession No. NP_078936.1, hypothetical protein FLJ22573 [*Homo sapiens*], Apr. 24, 2003.
Database EMBL Accession No. VT-1097106, *Homo sapiens*, Nov. 16, 2001.
"Novel TNF Receptor-like molecules and their bioloical uses," Expert Opin. Ther. Patents 12:1737-1739, 2002; from PCT Application No. WO 02/20762, Amgen, Inc.

\* cited by examiner

FIG. 1

Nucleic Acid Sequence (SEQ ID NO:1) and Amino Acid Sequence (SEQ ID NO:2) Encoding Human MK61T1 (hMK61T1)

Nucleic Acid Sequence

```
   1 GTAAAGATGG GGTTTCATTT TGTTGTCCAG GCTGATCTCT CGAACTCCTG
  51 GGCTCAAGTG ATCCTCCTGT CTTGGCCTCC CAAAGTGTTG GGATTACAGG
 101 CATGAGCCAC CACACCCAGC CCCTGCTTTA CTTCTAATGA CGGTTCTAAT
 151 TCTCCACAAT AACCCTATGA GACAGGTGCT ATCATTGTCT TATTTTAGGG
 201 ATGGAAAAGG GAGGGTGGGT GGGTGAGGAC ACGGCAGAGG TGGGATATGC
 251 ATTCTTGCAA TCTAGATCCG CAGCCCTGTT AGTCCCCTAG TGGCCTTGTG
 301 GGCTTCTCTG ATAACCGGCT CAGTTGGGGG ATGAGGGCTC GGGGGTAGAT
 351 TCCCGGCTTC CGAAGAGGCG TGAGAATTCT GTTCCCCCAC ATCACCGCGT
 401 CCTTTCTTCT GCCCGATTTC CCCGGAAAGT GTAGCAGAGG CGCTGTGTTT
 451 GGAAGTCCCG CTATCACGGC CCCCAGATG GGGCCTGGAC GATGCCTCCT
 501 GACGGCCTTG TTGCTTCTGG CCCTGGCGCC ACCGCCGGAA GCCTCCCAGT
 551 ACTGCGGCCG CCTTGAATAC TGGAACCCAG ACAACAAGTG CTGCAGCAGC
 601 TGCCTGCAAC GCTTCGGGCC GCCCCCCTGC CCGGACTATG AGTTCCGGGA
 651 AAACTGCGGA CTCAATGACC ACGGCGATTT CGTAACGCCC CCGTTCCGAA
 701 AGTGTTCTTC TGGGCAGTGC AACCCCGACG GCGCGGAGCT ATGTAGCCCC
 751 TGCGGCGGCG GAGCCGTGAC CCCTACTCCC GCCGCGGGCG GGGGCAGAAC
 801 CCCGTGGCGC TGCAGAGAGA GGCCGGTCCC TGCCAAGGGG CACTGCCCCC
 851 TCACACCTGG AAACCCAGGC GCCCCTAGCT CCCAGGAGCG CAGCTCACCA
 901 GCAAGTTCCA TTGCCTGGAG GACCCCTGAG CCTGTCCCTC AGCAGGCCTG
 951 GCCGAATTTC CTTCCGCTCG TGGTGCTGGT CCTGCTCCTG ACCTTGGCGG
1001 TGATAGCGAT CCTCCTGTTT ATTCTGCTCT GGCATCTCTG CTGGCCCAAG
1051 GAGAAAGCCG ACCCCTATCC CTATCCTGGC TTGGTCTGCG GAGTCCCCAA
1101 CACCCACACC CCTTCCTCCT CGCATCTGTC CTCCCCAGGC GCCCTGGAGA
1151 CAGGGGACAC ATGGAAGGAG GCCTCACTAC TTCCACTCCT GAGCAGGGAA
1201 CTGTCCAGTC TGGCGTCACA ACCCTGTCT CGCCTCCTGG ATGAGCTGGA
1251 GGTGCTGGAA GAGCTGATTG TACTGCTGGA CCCTGAGCCT GGGCCAGGTG
1301 GGGGTATGGC CCATGGCACT ACTCGACACC TGGCCGCAAG ATATGGGCTG
1351 CCTGCTGCCT GGTCCACCTT TGCCTATTCG CTGAGGCCGA GTCGCTCGCC
1401 GCTGCGGGCT CTGATTGAGA TGGTGGTGGC AAGGGAGCCC TCTGCCTCCC
1451 TGGGCCAGCT TGGCACACAC CTCGCCCAGC TAGGGCGGGC AGATGCATTG
1501 CGGGTGCTGT CCAAGCTTGG CTCATCTGGG GTTTGCTGGG CTTAACACCC
1551 AATAAAGAAC TTTGCTGACT ACTAAGCCCA GTATACAATT AGCACTGAAG
1601 TACTTCTTGA AGTACAATCC TAATTGGGCA AAGACCCAAC AGATAGCCTC
1651 ACTGCTCTTC GCCCTAGA
```

Amino Acid Sequence

```
   1 MGPGRCLLTA LLLLALAPPP EASQYCGRLE YWNPDNKCCS SCLQRFGPPP
  51 CPDYEFRENC GLNDHGDFVT PPFRKCSSGQ CNPDGAELCS PCGGGAVTPT
 101 PAAGGGRTPW RCRERPVPAK GHCPLTPGNP GAPSSQERSS PASSIAWRTP
 151 EPVPQQAWPN FLPLVVLVLL LTLAVIAILL FILLWHLCWP KEKADPYPYP
 201 GLVCGVPNTH TPSSSHLSSP GALETGDTWK EASLLPLLSR ELSSLASQPL
 251 SRLLDELEVL EELIVLLDPE PGPGGMAHG TTRHLAARYG LPAAWSTFAY
 301 SLRPSRSPLR ALIEMVVARE PSASLGQLGT HLAQLGRADA LRVLSKLGSS
 351 GVCWA
```

FIG. 2

Nucleic Acid Sequence (SEQ ID NO:3) and Amino Acid
Sequence (SEQ ID NO:4) Encoding Human MK61T2 (hMK61T2)

Nucleic Acid Sequence

```
   1  GTAAAGATGG GGTTTCATTT TGTTGTCCAG GCTGATCTCT CGAACTCCTG
  51  GGCTCAAGTG ATCCTCCTGT CTTGGCCTCC CAAAGTGTTG GGATTACAGG
 101  CATGAGCCAC CACACCCAGC CCCTGCTTTA CTTCTAATGA CGGTTCTAAT
 151  TCTCCACAAT AACCCTATGA GACAGGTGCT ATCATTGTCT TATTTTAGGG
 201  ATGGAAAAGG GAGGGTGGGT GGGTGAGGAC ACGGCAGAGG TGGGATATGC
 251  ATTCTTGCAA TCTAGATCCG CAGCCCTGTT AGTCCCCTAG TGGCCTTGTG
 301  GGCTTCTCTG ATAACCGGCT CAGTTGGGGG ATGAGGGCTC GGGGGTAGAT
 351  TCCCGGCTTC CGAAGAGGCG TGAGAATTCT GTTCCCCCAC ATCACCGCGT
 401  CCTTTCTTCT GCCCGATTTC CCCGGAAAGT GTAGCAGAGG CGCTGTGTTT
 451  GGAAGTCCCG CTATCACGGC CCCCAGATG GGGCCTGGAC GATGCCTCCT
 501  GACGGCCTTG TTGCTTCTGG CCCTGGCGCC ACCGCCGGAA GCCTCCCAGT
 551  ACTGCGGCCG CCTTGAATAC TGGAACCCAG ACAACAAGTG CTGCAGCAGC
 601  TGCCTGCAAC GCTTCGGGCC GCCCCCCTGC CCGGGTGAGA ATCCGAGACC
 651  GAGCCTTGGT TGGGCGGAGC TTGCAGAGGC CGGTCCCTGC CAAGGGGCAC
 701  TGCCCCCTCA CACCTGGAAA CCCAGGCGCC CCTAGCTCCC AGGAGCGCAG
 751  CTCACCAGCA AGTTCCATTG CCTGGAGGAC CCCTGAGCCT GTCCCTCAGC
 801  AGGCCTGGCC GAATTTCCTT CCGCTCGTGG TGCTGGTCCT GCTCCTGACC
 851  TTGGCGGTGA TAGCGATCCT CCTGTTTATT CTGCTCTGGC ATCTCTGCTG
 901  GCCCAAGGAG AAAGCCGACC CCTATCCCTA TCCTGGCTTG GTCTGCGGAG
 951  TCCCCAACAC CCACACCCCT TCCTCCTCGC ATCTGTCCTC CCCAGGCGCC
1001  CTGGAGACAG GGGACACATG GAAGGAGGCC TCACTACTTC CACTCCTGAG
1051  CAGGGAACTG TCCAGTCTGG CGTCACAACC CCTGTCTCGC CTCCTGGATG
1101  AGCTGGAGGT GCTGGAAGAG CTGATTGTAC TGCTGGACCC TGAGCCTGGG
1151  CCAGGTGGGG GTATGGCCCA TGGCACTACT CGACACCTGG CCGCAAGATA
1201  TGGGCTGCCT GCTGCCTGGT CCACCTTTGC CTATTCGCTG AGGCCGAGTC
1251  GCTCGCCGCT GCGGGCTCTG ATTGAGATGG TGGTGGCAAG GGAGCCCTCT
1301  GCCTCCCTGG GCCAGCTTGG CACACACCTC GCCCAGCTAG GGCGGGCAGA
1351  TGCATTGCGG GTGCTGTCCA AGCTTGGCTC ATCTGGGGTT TGCTGGGCTT
1401  AACACCCAAT AAAGAACTTT GCTGACTACT AAGCCCAGTA TACAATTAGC
1451  ACTGAAGTAC TTCTTGAAGT ACAATCCTAA TTGGGCAAAG ACCCAACAGA
1501  TAGCCTCACT GCTCTTCGCC CTAGA
```

Amino Acid Sequence

```
  1  MGPGRCLLTA LLLLALAPPP EASQYCGRLE YWNPDNKCCS SCLQRFGPPP
 51  CPGENPRPSL AWAELAEAGP CQGALPPHTW KPRRP*
```

FIG. 3

Nucleic Acid Sequence (SEQ ID NO:5) and Amino Acid
Sequence (SEQ ID NO:6) Encoding Human MK61T3 (hMK61T3)

Nucleic Acid Sequence

```
   1 GTAAAGATGG GGTTTCATTT TGTTGTCCAG GCTGATCTCT CGAACTCCTG
  51 GGCTCAAGTG ATCCTCCTGT CTTGGCCTCC CAAAGTGTTG GGATTACAGG
 101 CATGAGCCAC CACACCCAGC CCCTGCTTTA CTTCTAATGA CGGTTCTAAT
 151 TCTCCACAAT AACCCTATGA GACAGGTGCT ATCATTGTCT TATTTTAGGG
 201 ATGGAAAAGG GAGGGTGGGT GGGTGAGGAC ACGGCAGAGG TGGGATATGC
 251 ATTCTTGCAA TCTAGATCCG CAGCCCTGTT AGTCCCCTAG TGGCCTTGTG
 301 GGCTTCTCTG ATAACCGGCT CAGTTGGGGG ATGAGGGCTC GGGGGTAGAT
 351 TCCCGGCTTC CGAAGAGGCG TGAGAATTCT GTTCCCCCAC ATCACCGCGT
 401 CCTTTCTTCT GCCCGATTTC CCCGGAAAGT GTAGCAGAGG CGCTGTGTTT
 451 GGAAGTCCCG CTATCACGGC CCCCAGATG GGGCCTGGAC GATGCCTCCT
 501 GACGGCCTTG TTGCTTCTGG CCCTGGCGCC ACCGCCGGAA GCCTCCCAGT
 551 ACTGCGGCCG CCTTGAATAC TGGAACCCAG ACAACAAGTG CTGCAGCAGC
 601 TGCCTGCAAC GCTTCGGGCC GCCCCCCTGC CCGGACTATG AGTTCCGGGA
 651 AAACTGCGGA CTCAATGACC ACGGCGATTT CGTAACGCCC CCGTTCCGAA
 701 AGTGTTCTTC TGGGCAGTGC AACCCCGACG GCGCGGAGCT ATGTAGCCCC
 751 TGCGGCGGCG GAGCCGTGAC CCCTACTCCC GCCGCGGGCG GGGCAGAAC
 801 CCCGTGGCGC TGCAGAGAGA ACTGTCCAGT CTGGCGTCAC AACCCCTGTC
 851 TCGCCTCCTG GATGAGCTGG AGGTGCTGGA AGAGCTGATT GTACTGCTGG
 901 ACCCTGAGCC TGGGCCAGGT GGGGGTATGG CCCATGGCAC TACTCGACAC
 951 CTGGCCGCAA GATATGGGCT GCCTGCTGCC TGGTCCACCT TTGCCTATTC
1001 GCTGAGGCCG AGTCGCTCGC CGCTGCGGGC TCTGATTGAG ATGGTGGTGG
1051 CAAGGGAGCC CTCTGCCTCC CTGGGCCAGC TTGGCACACA CCTCGCCCAG
1101 CTAGGCGGG CAGATGCATT GCGGGTGCTG TCCAAGCTTG GCTCATCTGG
1151 GGTTTGCTGG GCTTAACACC CAATAAAGAA CTTTGCTGAC TACTAAGCCC
1201 AGTATACAAT TAGCACTGAA GTACTCTTG AAGTACAATC CTAATTGGGC
1251 AAAGACCCAA CAGATAGCCT CACTGCTCTT CGCCCTAGA
```

Amino Acid Sequence

```
   1 MGPGRCLLTA LLLLALAPPP EASQYCGRLE YWNPDNKCCS SCLQRFGPPP
  51 CPDYEFRENC GLNDHGDFVT PPFRKCSSGQ CNPDGAELCS PCGGGAVTPT
 101 PAAGGGRTPW RCRENCPVWR HNPCLASWMS WRCWKS*
```

FIG. 4

Nucleic Acid Sequence (SEQ ID NO:7) and Amino Acid
Sequence (SEQ ID NO:8) Encoding Human MK61T4 (hMK61T4)

Nucleic Acid Sequence

```
   1  GTAAAGATGG GGTTTCATTT TGTTGTCCAG GCTGATCTCT CGAACTCCTG
  51  GGCTCAAGTG ATCCTCCTGT CTTGGCCTCC CAAAGTGTTG GGATTACAGG
 101  CATGAGCCAC CACACCCAGC CCTGCTTTA CTTCTAATGA CGGTTCTAAT
 151  TCTCCACAAT AACCCTATGA GACAGGTGCT ATCATTGTCT TATTTTAGGG
 201  ATGGAAAAGG GAGGGTGGGT GGGTGAGGAC ACGGCAGAGG TGGGATATGC
 251  ATTCTTGCAA TCTAGATCCG CAGCCCTGTT AGTCCCCTAG TGGCCTTGTG
 301  GGCTTCTCTG ATAACCGGCT CAGTTGGGGG ATGAGGGCTC GGGGGTAGAT
 351  TCCCGGCTTC CGAAGAGGCG TGAGAATTCT GTTCCCCCAC ATCACCGCGT
 401  CCTTTCTTCT GCCCGATTTC CCCGGAAAGT GTAGCAGAGG CGCTGTGTTT
 451  GGAAGTCCCG CTATCACGGC CCCCCAGATG GGGCCTGGAC GATGCCTCCT
 501  GACGGCCTTG TTGCTTCTGG CCCTGGCGCC ACCGCCGGAA GCCTCCCAGT
 551  ACTGCGGCCG CCTTGAATAC TGGAACCCAG ACAACAAGTG CTGCAGCAGC
 601  TGCCTGCAAC GCTTCGGGCC GCCCCCCTGC CCGGGCGCCC TGGAGACAGG
 651  GGACACATGG AAGGAGGCCT CACTACTTCC ACTCCTGAGC AGGGAACTGT
 701  CCAGTCTGGC GTCACAACCC CTGTCTCGCC TCCTGGATGA GCTGGAGGTG
 751  CTGGAAGAGC TGATTGTACT GCTGGACCCT GAGCCTGGGC CAGGTGGGGG
 801  TATGGCCCAT GGCACTACTC GACACCTGGC CGCAAGATAT GGGCTGCCTG
 851  CTGCCTGGTC CACCTTTGCC TATTCGCTGA GGCCGAGTCG CTCGCCGCTG
 901  CGGGCTCTGA TTGAGATGGT GGTGGCAAGG GAGCCCTCTG CCTCCCTGGG
 951  CCAGCTTGGC ACACACCTCG CCCAGCTAGG GCGGGCAGAT GCATTGCGGG
1001  TGCTGTCCAA GCTTGGCTCA TCTGGGGTTT GCTGGGCTTA ACACCCAATA
1051  AAGAACTTTG CTGACTACTA AGCCCAGTAT ACAATTAGCA CTGAAGTACT
1101  TCTTGAAGTA CAATCCTAAT TGGGCAAAGA CCCAACAGAT AGCCTCACTG
1151  CTCTTCGCCC TAGA
```

Amino Acid Sequence

```
   1  MGPGRCLLTA LLLLALAPPP EASQYCGRLE YWNPDNKCCS SCLQRFGPPP
  51  CPGALETGDT WKEASLLPLL SRELSSLASQ PLSRLLDELE VLEELIVLLD
 101  PEPGPGGGMA HGTTRHLAAR YGLPAAWSTF AYSLRPSRSP LRALIEMVVA
 151  REPSASLGQL GTHLAQLGRA DALRVLSKLG SSGVCWA*
```

FIG. 5

Nucleic Acid Sequence (SEQ ID NO:9) and Amino Acid Sequence (SEQ ID NO:10) Encoding Human MK61T5 (hMK61T5)

Nucleic Acid Sequence

```
   1 GTAAAGATGG GGTTTCATTT TGTTGTCCAG GCTGATCTCT CGAACTCCTG
  51 GGCTCAAGTG ATCCTCCTGT CTTGGCCTCC CAAAGTGTTG GGATTACAGG
 101 CATGAGCCAC CACACCCAGC CCCTGCTTTA CTTCTAATGA CGGTTCTAAT
 151 TCTCCACAAT AACCCTATGA GACAGGTGCT ATCATTGTCT TATTTTAGGG
 201 ATGGAAAAGG GAGGGTGGGT GGGTGAGGAC ACGGCAGAGG TGGGATATGC
 251 ATTCTTGCAA TCTAGATCCG CAGCCCTGTT AGTCCCTAG TGGCCTTGTG
 301 GGCTTCTCTG ATAACCGGCT CAGTTGGGGG ATGAGGGCTC GGGGGTAGAT
 351 TCCCGGCTTC CGAAGAGGCG TGAGAATTCT GTTCCCCAC ATCACCGCGT
 401 CCTTTCTTCT GCCCGATTTC CCCGAAAGT GTAGCAGAGG CGCTGTGTTT
 451 GGAAGTCCCG CTATCACGGC CCCCAGATG GGGCCTGGAC GATGCCTCCT
 501 GACGGCCTTG TTGCTTCTGG CCCTGGCGCC ACCGCCGGAA GCCTCCCAGT
 551 ACTGCGGCCG CCTTGAATAC TGGAACCCAG ACAACAAGTG CTGCAGCAGC
 601 TGCCTGCAAC GCTTCGGGCC GCCCCCCTGC CCGGAGGCCG GTCCCTGCCA
 651 AGGGGCACTG CCCCCTCACA CCTGGAAACC CAGGCGCCCC TAGCTCCCAG
 701 GAGCGCAGCT CACCAGCAAG TTCCATTGCC TGGAGGACCC CTGAGCCTGT
 751 CCCTCAGCAG GCCTGGCCGA ATTTCCTTCC GCTCGTGGTG CTGGTCCTGC
 801 TCCTGACCTT GGCGGTGATA GCGATCCTCC TGTTTATTCT GCTCTGGCAT
 851 CTCTGCTGGC CCAAGGAGAA AGCCGACCCC TATCCCTATC CTGGCTTGGT
 901 CTGCGGAGTC CCCAACACCC ACACCCCTTC CTCCTCGCAT CTGTCCTCCC
 951 CAGGCGCCCT GGAGACAGGG GACACATGGA AGGAGGCCTC ACTACTTCCA
1001 CTCCTGAGCA GGGAACTGTC CAGTCTGGCG TCACAACCCC TGTCTCGCCT
1051 CCTGGATGAG CTGGAGGTGC TGGAAGAGCT GATTGTACTG CTGGACCCTG
1101 AGCCTGGGCC AGGTGGGGGT ATGGCCCATG GCACTACTCG ACACCTGGCC
1151 GCAAGATATG GGCTGCCTGC TGCCTGGTCC ACCTTTGCCT ATTCGCTGAG
1201 GCCGAGTCGC TCGCCGCTGC GGGCTCTGAT TGAGATGGTG GTGGCAAGGG
1251 AGCCCTCTGC CTCCCTGGGC CAGCTTGGCA CACACCTCGC CCAGCTAGGG
1301 CGGGCAGATG CATTGCGGGT GCTGTCCAAG CTTGGCTCAT CTGGGGTTTG
1351 CTGGGCTTAA CACCCAATAA AGAACTTTGC TGACTACTAA GCCCAGTATA
1401 CAATTAGCAC TGAAGTACTT CTTGAAGTAC AATCCTAATT GGGCAAAGAC
1451 CCAACAGATA GCCTCACTGC TCTTCGCCCT AGA
```

Amino Acid Sequence

```
 1 MGPGRCLLTA LLLLALAPPP EASQYCGRLE YWNPDNKCCS SCLQRFGPPP
51 CPEAGPCQGA LPPHTWKPRR P*
```

FIG. 6

Nucleic Acid Sequence (SEQ ID NO:11) and Amino Acid Sequence (SEQ ID NO:12) Encoding Human MK61T6 (hMK·

Nucleic Acid Sequence

```
   1  GTAAAGATGG GGTTTCATTT TGTTGTCCAG GCTGATCTCT CGAACTCCTG
  51  GGCTCAAGTG ATCCTCCTGT CTTGGCCTCC CAAAGTGTTG GGATTACAGG
 101  CATGAGCCAC CACACCCAGC CCCTGCTTTA CTTCTAATGA CGGTTCTAAT
 151  TCTCCACAAT AACCCTATGA GACAGGTGCT ATCATTGTCT TATTTTAGGG
 201  ATGGAAAAGG GAGGGTGGGT GGGTGAGGAC ACGGCAGAGG TGGGATATGC
 251  ATTCTTGCAA TCTAGATCCG CAGCCCTGTT AGTCCCCTAG TGGCCTTGTG
 301  GGCTTCTCTG ATAACCGGCT CAGTTGGGGG ATGAGGGCTC GGGGGTAGAT
 351  TCCCGGCTTC CGAAGAGGCG TGAGAATTCT GTTCCCCCAC ATCACCGCGT
 401  CCTTTCTTCT GCCCGATTTC CCCGGAAAGT GTAGCAGAGG CGCTGTGTTT
 451  GGAAGTCCCG CTATCACGGC CCCCAGATG GGGCCTGGAC GATGCCTCCT
 501  GACGGCCTTG TTGCTTCTGG CCCTGGCGCC ACCGCCGGAA GCCTCCCAGT
 551  ACTGCGGCCG CCTTGAATAC TGGAACCCAG ACAACAAGTG CTGCAGCAGC
 601  TGCCTGCAAC GCTTCGGGCC GCCCCCCTGC CCGGAACTGT CCAGTCTGGC
 651  GTCACAACCC CTGTCTCGCC TCCTGGATGA GCTGGAGGTG CTGGAAGAGC
 701  TGATTGTACT GCTGGACCCT GAGCCTGGGC CAGGTGGGGG TATGGCCCAT
 751  GGCACTACTC GACACCTGGC CGCAAGATAT GGGCTGCCTG CTGCCTGGTC
 801  CACCTTTGCC TATTCGCTGA GGCCGAGTCG CTCGCCGCTG CGGGCTCTGA
 851  TTGAGATGGT GGTGGCAAGG GAGCCCTCTG CCTCCCTGGG CCAGCTTGGC
 901  ACACACCTCG CCCAGCTAGG GCGGGCAGAT GCATTGCGGG TGCTGTCCAA
 951  GCTTGGCTCA TCTGGGGTTT GCTGGGCTTA ACACCCAATA AAGAACTTTG
1001  CTGACTACTA AGCCCAGTAT ACAATTAGCA CTGAAGTACT TCTTGAAGTA
1051  CAATCCTAAT TGGGCAAAGA CCCAACAGAT AGCCTCACTG CTCTTCGCCC
1105  TAGA
```

Amino Acid Sequence

```
  1  MGPGRCLLTA LLLLALAPPP EASQYCGRLE YWNPDNKCCS SCLQRFGPPP
 51  CPELSSLASQ PLSRLLDELE VLEELIVLLD PEPGPGGGMA HGTTRHLAAR
101  YGLPAAWSTF AYSLRPSRSP LRALIEMVVA REPSASLGQL GTHLAQLGRA
151  DALRVLSKLG SSGVCWA*
```

FIG. 7

Nucleic Acid Sequence (SEQ ID NO:13) and Amino Acid Sequence (SEQ ID NO:14) Encoding Mouse MK61 (mMK61; Smi12-00051-F3)

Nucleic Acid Sequence

```
   1 CGGACGCGTG GGCGGACGCG TGGGTGGGTC TGCACTGAAA CAGTGTGGGT
  51 GGAAGTGGTC ACAGCCCTCA AGCTGCAGGC TCTGCTGAGA TGGGGCCCAG
 101 CTGGCTTCTC TGGACAGTGG CGGTGGCAGT GCTGCTCCTG ACCCGGGCTG
 151 CGTCAATGGA AGCCTCTAGC TTCTGTGGCC ACCTTGAGTA CTGGAACTCT
 201 GACAAGAGGT GCTGCAGCCG CTGCCTGCAA CGCTTTGGGC CTCCTGCATG
 251 TCCTGATCAC GAGTTCACGG AAAACTGCGG GCTCAATGAC TTCGGCGATA
 301 CTGTAGCACA TCCTTTCAAA AAGTGTTCCC CTGGGTATTG CAACCCCAAT
 351 GGCACAGAGC TGTGTAGCCA GTGTAGCAGC GGAGCCGCCG CAGCCCCAGC
 401 TCACGTGGAG AGCCCTGGTA GAACCCACAA GCAGTGTAGA AAGAAGCCCG
 451 TCCCTCCCAA GGATGTCTGT CCTCTTAAAC CTGAAGACGC AGGTGCCTCT
 501 AGCTCACCTG GGAGGTGGAG CCTTGGGCAG ACAACCAAGA ATGAGGTCTC
 551 CAGCCGACCA GGTTTTGTCT CAGCCTCAGT GCTGCCTCTG GCAGTGTTGC
 601 CACTGTTGCT GGTGCTGCTT CTGATATTGG CAGTGGTCTT GCTCTCTTTG
 651 TTCAAGAGAA AGTCCGTTC CCGTCCTGGT TCCAGCTCAG CTTTTGGAGA
 701 TCCCAGCACC TCTCTACATT ACTGGCCCTG CCCAGGTACC CTGGAGGTAT
 751 TGGAAAGTAG AAACAGAGGG AAAGCTAATC TGCTGCAGCT CTCAAGCTGG
 801 GAGCTTCAGG GTCTGGCCTC TCAGCCCCTC TCCCTCCTGC TGGATGAGCT
 851 GGAAGTTCTG GAGGAGCTGA TTATGCTATT GGACCCTGAG CCTGGGCCGA
 901 GCGGGAGCAC GGCTTATGGT ACCACACGAC ACCTGGCTGC AAGATACGGG
 951 CTGCCTGCCA CCTGGTCTAC CTTCGCCTAC TCACTTGGC CCAGTCGCTC
1001 ACCCCTGCGG GCCCTGATTG AGATGGTTGT GGCAAGGGAG CCTTCTGCTA
1051 CTCTGGGTCA ATTCGGCACA TATTTGGCTC AGCTAGGTCG CACAGATGCT
1101 CTGCAGGTGC TATCTAAACT TGGCTGAGTC AGAGTTTGCT GGGGCTTACT
1151 ACTCCATCAA TAAAGTTTCC CTTGAAGCCA AAAAAAAAAA AAAAAAAAAA
1201 AA
```

Amino Acid Sequence

```
  1 MGFSWLLWTV AVAVLLLTRA ASMEASSFCG HLEYWNSDKR CCSRCLQRFG
 51 FFACFDHEFT ENCGLNDFGD TVAHPFKKCS PGYCNPNGTE LCSQCSSGAA
101 AAPAHVESPG RTHKQCRKKP VPPKDVCPLK PEDAGASSSP GRWSLGQTTK
151 NEVSSRPGFV SASVLPLAVL PLLLVLLLIL AVVLLSLFKR KVRSRPGSSS
201 AFGDPSTSLH YWPCPGTLEV LESRNRGKAN LLQLSSWELQ GLASQPLSLL
251 LDELEVLEEL IMLLDPEPGP SGSTAYGTTR HLAARYGLPA TWSTFAYSLR
301 PSRSPLRALI EMVVAREPSA TLGQFGTYLA QLGRTDALQV LSKLG*
```

FIG. 8

Nucleic Acid Sequence (SEQ ID NO:15) and Amino Acid Sequence (SEQ ID NO:16) Encoding Mouse mMK61-Fc Fusion Polypeptide (mMK61-Fc)

Nucleic Acid Sequence

```
   1  CCACCATGGG GCCCAGCTGG CTTCTCTGGA CAGTGGCGGT GGCAGTGCTG
  51  CTCCTGACCC GGGCTGCGTC AATGGAAGCC TCTAGCTTCT GTGGCCACCT
 101  TGAGTACTGG AACTCTGACA AGAGGTGCTG CAGCCGCTGC CTGCAACGCT
 151  TTGGGCCTCC TGCATGTCCT GATCACGAGT TCACGGAAAA CTGCGGGCTC
 201  AATGACTTCG GCGATACTGT AGCACATCCT TTCAAAAAGT GTTCCCCTGG
 251  GTATTGCAAC CCCAATGGCA CAGAGCTGTG TAGCCAGTGT AGCAGCGGAG
 301  CCGCCGCAGC CCCAGCTCAC GTGGAGAGCC CTGGTAGAAC CACAAAGCAG
 351  TGTAGAAAGA AGCCCGTCCC TCCCAAGGAT GTCTGTCCTC TTAAACCTGA
 401  AGACGCAGGT GCCTCTAGCT CACCTGGGAG GTGGAGCCTT GGGCAGACAA
 451  CCAAGAATGA GGTCGCGGCC GCTCGTCGTG CATCAGTAGA GCCCAAATCT
 501  TGTGACAAAA CTCACACATG CCCACCGTGC CCAGCACCTG AACTCCTGGG
 551  GGGACCGTCA GTCTTCCTCT TCCCCCCAAA ACCCAAGGAC ACCCTCATGA
 601  TCTCCCGGAC CCCTGAGGTC ACATGCGTGG TGGTGGACGT GAGCCACGAA
 651  GACCCTGAGG TCAAGTTCAA CTGGTACGTG GACGGCGTGG AGGTGCATAA
 701  TGCCAAGACA AAGCCGCGGG AGGAGCAGTA CAACAGCACG TACCGTGTGG
 751  TCAGCGTCCT CACCGTCCTG CACCAGGACT GGCTGAATGG CAAGGAGTAC
 801  AAGTGCAAGG TCTCCAACAA AGCCCTCCCA GCCCCCATCG AGAAAACCAT
 851  CTCCAAAGCC AAAGGGCAGC CCCGAGAACC ACAGGTGTAC ACCCTGCCCC
 901  CATCCCGGGA TGAGCTGACC AAGAACCAGG TCAGCCTGAC CTGCCTGGTC
 951  AAAGGCTTCT ATCCCAGCGA CATCGCCGTG GAGTGGGAGA GCAATGGGCA
1001  GCCGGAGAAC AACTACAAGA CCACGCCTCC CGTGCTGGAC TCCGACGGCT
1051  CCTTCTTCCT CTACAGCAAG CTCACCGTGG ACAAGAGCAG GTGGCAGCAG
1101  GGGAACGTCT TCTCATGCTC CGTGATGCAT GAGGCTCTGC ACAACCACTA
1151  CACGCAGAAG AGCCTCTCCC TGTCTCCGGG TAAAAGAAGA GCTAGTCTCC
1201  ATCATCATCA TCATCATTGA TAAGTCGAC
```

Amino Acid Sequence

```
  1  MGPSWLLWTV AVAVLLLTRA ASMEASSFCG HLEYWNSDKR CCSRCLQRFG
 51  FPACPDHEFT ENCGLNDFGD TVAHPFKKCS PGYCNPNGTE LCSQCSSGAA
101  AAPAHVESPG RTHKQCRKKP VPPKDVCPLK PEDAGASSSP GRWSLGQTTK
151  NEVAAARRAS VEPKSCDKTH TCPPCPAPEL LGGPSVFLFP PKPKDTLMIS
201  RTPEVTCVVV DVSHEDPEVK FNWYVDGVEV HNAKTKPREE QYNSTYRVVS
251  VLTVLHQDWL NGKEYKCKVS NKALPAPIEK TISKAKGQPR EPQVYTLPPS
301  RDELTKNQVS LTCLVKGFYP SDIAVEWESN GQPENNYKTT PPVLDSDGSF
351  FLYSKLTVDK SRWQQGNVFS CSVMHEALHN HYTQKSLSLS PGKRRASLHH
401  HHHH**
```

Lane 1: Positive control lysate
Lane 2: Positive control Medium (the detected protein is 300kd)
Lane 3: Negative control lysate
Lane 4: Negative control medium
Lane 5: Smil2-00051-f3 Fc transfected cell lysate
Lane 6: Smil2-00051-f3 Fc (sample 1) transfected cell Medium
Lane 7: Smil2-00051-f3 Fc (sample 2) transfected cell Medium
Lane 8: Smil2-00051-f3 Fc (sample 3) transfected cell medium

FIG. 10

Comparison of mMK61 Amino Acid Sequence (SEQ ID NO:14), (mMK61) to the Amino Acid Sequence of an OPG receptor, Mrank, a Known TNFR Family Member: (SEQ ID NO:17)

```
                    10        20        30        40        50
         60
       Mrank    MAFRARRRRQLPAPLLALCVLLVPLQVTLQVTPPCTQERHYEHLGRCCSRCEPGKYLSSK
                 :|: |||:  .::::::  | : ::::    ||||||   ::
       mMK61     MGFSWLLWTVAVAVLLLTRAASMEASSFCGHLEYWNSDKRCCSRCLQ-RFGPPA
                       10        20        30        40        50

70        80        90       100       110
       Mrank    CTPTSDSVCLPCGFDEYLDTWNEE-DKCLLHKVCDAGKALVA-VDPGNHTAP
                | | :    || ::: ||  :   ||         | | :  : | · :||
       mMK61    C-FDHE-FTENCGLNDFGDTVAHPFKKCSPGYCNPNGTELCSQCSSGAAAAP
                      60        70        80        90       100
```

FIG. 11

Comparison of mMK61 Amino Acid Sequence (SEQ ID NO:14), (mMK61) to the Amino Acid Sequence of a Fas Ligand Receptor, Mfasr, (SEQ ID NO:18)

```
                    10         20         30         40         50
Mfasr       MLWIWAVLFLVLAGSQLRVHTQGTNSISESLKLRRRVHETDKNC-SEGLYQGGPF
            :||   ||   |:|:    |: ::  ::|:     |:     ::|| | |: | : ||
mMK61       MGFSWLLWTVAVAVLLLT----RAASMEASSFCGHLEYW----NSDKRCCSRCLQRFGPP
                    10         20         30             40         50

60         70         80         90        100
                                                                            110
Mfasr       CCQPCQPGKKKVEDCKMNG-GTPTCAP---CTEGKEYMDKNHYADKCRRCTLCDEEHGLE
            |    |  ::  :|:| :|   |   :   |   |: |   |  :   ::    | :|:          :
mMK61       AC----FDHEFTENCGLNDFGDTVAHPFKKCSPG--YCNPNG-TELCSQCSSGAAAAPAH
                    60         70         80         90        100

120        130        140        150        160
Mfasr       VETNCTLTQNTKCKCKPDFYCDSPGCEHCVRCASCEHGTLEPCTATSNTNCRKQS-----
            ||:    :   :|: ||    |    :     ||    |      :|:|       : :
mMK61       VESPGRTHR--QCRKKFVPPKDVCFLKFEDAGASSSPGRWSLGQTTKNEVSSRPGFVSAS
                   110        120        130        140        150        160

170        180        190        200
Mfasr       --FRNRLWLLTILVLLIPLVFIY---RKYRKRKCWKRRQDDPES
              |    | ||  :|:|::  :|::     || |:|    :      || :
mMK61       VLPLAVLPLLLVLLLILAVVLLSLFKRKVRSRPGSSSAFGDPST
                   170        180        190        200
```

FIG. 12

Comparison of mMK61 Amino Acid Sequence (SEQ ID NO:14),
(mMK61) to the Amino Acid Sequence of a Known Mouse
Lymphotoxin-Beta Receptor, Tnfrc, (SEQ ID NO:19)

```
                                 90          100         110
Tnfrc                            EHWNYLTICQLCRPCDPVMGLEEIAP--CT
                                 |:||    |   |   |     |::::| |
mMK61                            EYWNSDKRC--CSRC-----LQRFGPPACP
                                         40              50

120           130         140         150         160
Tnfrc        SKRKTQ-C-------------RCQPGMFCAAWALECTHCELLSDCPPGTEAELKDEVGK
             :::  |: |            :|:|| :|       :  || |:|  |: |         :
mMK61        DHEFTENCGLNDFGDTVAHFFKKCSPG-YCNP-----NGTELCSQCSSGAAAAPAHVESP
                60        70        80              90        100

170         180         190         200         210         220
Tnfrc        GNNHCVFCKAGHFQNTSSFSARCQPHTRCENQGLVEAAPGTAQSDTTCKNPLEPLPPEMS
             | :|    |:     ::    |:    | |    :  |:   |   ::||    :   |||  :    |    :|
mMK61        GRTHK-QCR----KKPVFPKDVC-P-LKPEDAG-ASSSPGRWSLGQTTKNEVSSRPGFVS
             110         120         130.        140         150
160

230         240         250         260         270
Tnfrc        GTMLMLAVL-LPLAFFLLLATVFSCIWK----SHPSLCRKLG---SLLKRRPQGEGPNPV
             :::| ||||  |  |:::|:||:|:    ::|       :|      :|:     |    |
mMK61        ASVLPLAVLFLLLVLLLILAVVLLSLFKRKVRSRPGSSSAFGDPSTSLHYWPC-PGTLEV
             170         180         190         200         210
220

280         290         300         310         320         330
Tnfrc        AGSWEFPKAHPYFPDLVQ-FLLPISGDVS-PVSTGLPAAPVLEAGVPQQQSPLDLTREPQ
             |  :  ||          :|:|       ::| :|  |:| |     |||         | :|            | :|
mMK61        LESRNRGKA-----NLLQLSSWELQGLASQPLSLLLDELEVLEE--------LIMLLDP-
                          230         240         250                 260

340
Tnfrc        LEPGEQSQVAHGTN
             ||| ::::|:||:
mMK61        -EPGPSGSTAYGTT
              270
```

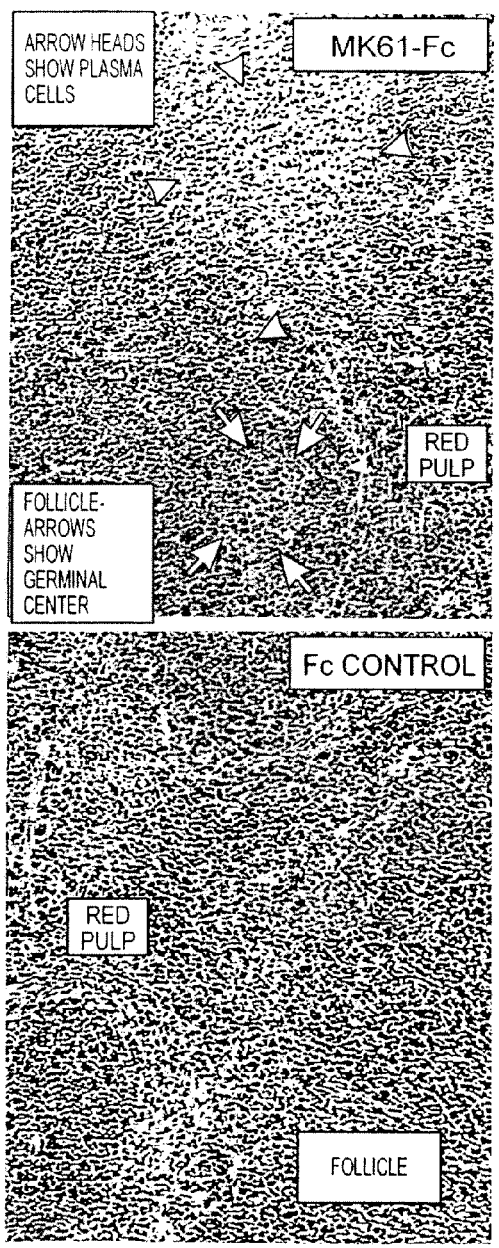
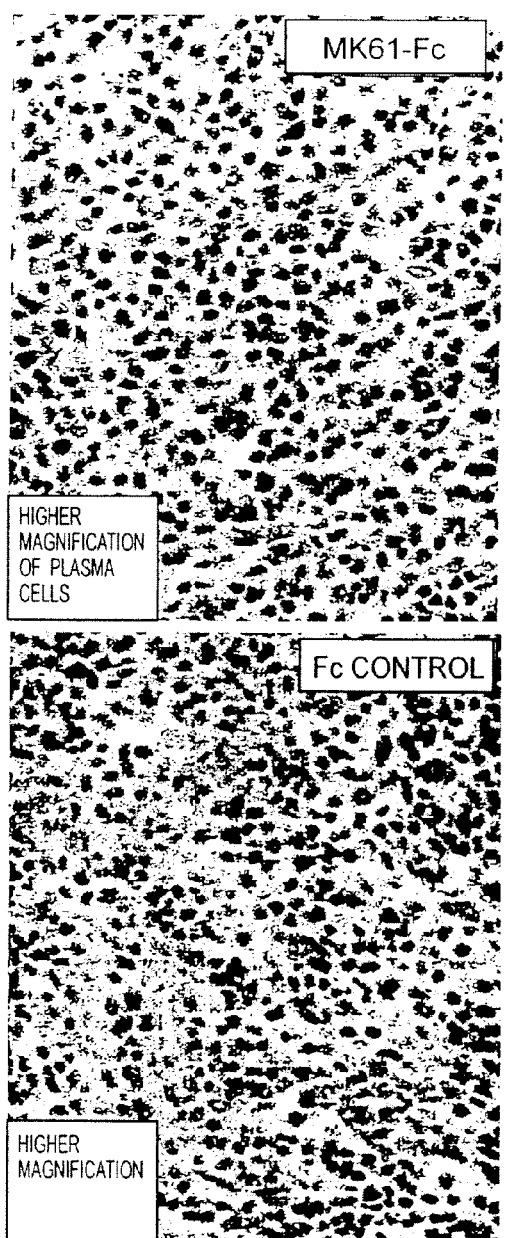
FIG. 20A  FIG. 20B
FIG. 20C  FIG. 20D

FIG. 24

```
  1  MGPGRCLLTA LLLLALAPPP EASQYCGRLE YWNPDNKCCS SCLQRFGPPP
 51  CPDYEFRENC GLNDHGDFVT PPFRKCSSGQ CNPDGAELCS PCGGAVTPT
101  PAAGGGRTPW RCRERPVPAK GHCPLTPGNP GAPSSQERSS PASSIAWRTP
151  EPVDKTHTCP PCPAPELLGG PSVFLFPPKP KDTLMISRTP EVTCVVVDVS
201  HEDPEVKFNW YVDGVEVHNA KTKPREEQYN STYRVVSVLT VLHQDWLNGK
251  EYKCKVSNKA LPAPIEKTIS KAKGQPREPQ VYTLPPSRDE LTKNQVSLTC
301  LVKGFYPSDI AVEWESNGQP ENNYKTTPPV LDSDGSFFLY SKLTVDKSRW
351  QQGNVFSCSV MHEALHNHYT QKSLSLSPGK
```

FIG. 25

```
  1  MGPSWLLWTV AVAVLLLTRA ASMEASSFCG HLEYWNSDKR CCSRCLQRFG
 51  PPACPDHEFT ENCGLNDFGD TVAHPFKKCS PGYCNPNGTE LCSQCSSGAA
101  AAPAHVESPG RTHKQCRKKP VPPKDVCPLK PEDAGASSSP GRWSLGQTTK
151  NEVDKTHTCP PCPAPELLGG PSVFLFPPKP KDTLMISRTP EVTCVVVDVS
201  HEDPEVKFNW YVDGVEVHNA KTKPREEQYN STYRVVSVLT VLHQDWLNGK
251  EYKCKVSNKA LPAPIEKTIS KAKGQPREPQ VYTLPPSRDE LTKNQVSLTC
301  LVKGFYPSDI AVEWESNGQP ENNYKTTPPV LDSDGSFFLY SKLTVDKSRW
351  QQGNVFSCSV MHEALHNHYT QKSLSLSPGK
```

ANTIBODY TO TNF RECEPTOR-LIKE MOLECULES

The present application is a continuation application of U.S. patent application Ser. No. 09/948,018, now issued U.S. Pat. No. 7,153,669, which was filed Sep. 5, 2001, which in turn claims benefit under 35 U.S.C. § 119 of U.S. Application Ser. No. 60/230,191, which was filed Sep. 5, 2000, which is incorporated herein by reference in its entirety.

FIELD OF THE INVENTION

The present invention relates to novel TNF receptor. (TNFr)-like polypeptides and nucleic acid molecules encoding the same, termed "MK61" herein.

The invention also relates to vectors, host cells, pharmaceutical compositions, selective binding agents and methods for producing MK61 polypeptides. Also provided for are methods for the diagnosis, treatment, amelioration, and/or prevention of diseases associated with MK61 polypeptides.

BACKGROUND OF THE INVENTION

Technical advances in identification, cloning, expression and manipulation of nucleic acid molecules and deciphering of the human genome have greatly accelerated discovery of novel therapeutics based upon deciphering of the human genome. Rapid nucleic acid sequencing techniques can now generate sequence information at unprecedented rates and, coupled with computational analyses, allow the assembly of overlapping sequences into the partial and entire genomes as well as identification of polypeptide-encoding regions. A comparison of a predicted amino acid sequence against a database compilation of known amino acid sequences allows one to determine the extent of homology to previously identified sequences and/or structural landmarks. The cloning and expression of a polypeptide-encoding region of a nucleic acid molecule provides a polypeptide product for structural and functional analyses. The manipulation of nucleic acid molecules and encoded polypeptides to create variant and derivatives thereof may confer advantageous properties on a product for use as a therapeutic.

In spite of significant technical advances in genome research over the past decade, the potential for development of novel therapeutics based on the human genome is still largely unrealized. Many genes encoding potentially beneficial polypeptide therapeutics or those encoding polypeptides, which may act as "targets" for therapeutic molecules, have still not been identified.

Accordingly, it is an object of the invention to identify novel polypeptides, and nucleic acid molecules encoding the same, which have diagnostic or therapeutic benefit.

After years of study in necrosis of tumors, tumor necrosis factors (TNFs) α and β were finally cloned in 1984. The ensuing years witnessed the emergence of a superfamily of TNF cytokines, including fas ligand (FasL), CD27 ligand (CD27L), CD30 ligand (CD30L), CD40 ligand (CD40L), TNF-related apoptosis-inducing ligand (TRAIL, also designated AGP-1), osteoprotegerin binding protein (OPG-BP or OPG ligand), 4-1BB ligand, LIGHT, APRIL, and TALL-1. Smith et al. (1994), *Cell,* 76: 959-962; Lacey et al. (1998), *Cell,* 93: 165-176; Chichepotiche et al. (1997), *J. Biol. Chem.,* 272: 32401-32410; Mauri et al. (1998), *Immunity,* 8: 21-30; Hahne et al. (1998), *J. Exp. Med.,* 188: 1185-90; Shu et al. (1999), *J. Leukocyte Biology,* 65: 680-3. This family is unified by its structure, particularly at the C-terminus. In addition, most members known to date are expressed in immune compartments, although some members are also expressed in other tissues or organs, as well. Smith et al. (1994), *Cell* 76: 959-62. All ligand members, with the exception of LT-α, are type II transmembrane proteins, characterized by a conserved 150 amino acid region within C-terminal extracellular domain. Though restricted to only 20-25% identity, the conserved 150 amino acid domain folds into a characteristic β-pleated sheet sandwich and trimerizes. This conserved region can be proteolyticaly released, thus generating a soluble functional form. Banner et al. (1993), *Cell,* 73: 431-445.

Many members within this ligand family are expressed in lymphoid enriched tissues and play important roles in the immune system development and modulation. Smith et al. (1994). For example, TNFα is mainly synthesized by macrophages and is an important mediator for inflammatory responses and immune defenses. Tracey & Cerami (1994), *Annu. Rev. Med.,* 45: 491-503. Fas-L, predominantly expressed in activated T cell, modulates TCR-mediated apoptosis of thymocyts. Nagata et al. (1995) *Immunology Today,* 16:39-43; Castrim et al. (1996), *Immunity,* 5:617-27. CD40L, also expressed by activated T cells, provides an essential signal for B cell survival, proliferation and immunoglobulin isotype switching. Noelle (1996), *Immunity,* 4: 415-9.

The cognate receptors for most of the TNF ligand family members have been identified. These receptors share characteristic multiple cysteine-rich repeats within their extracellular domains, and do not possess catalytic motifs within cytoplasmic regions. Smith et al. (1994). Two subgroups of TNFR homologues: Fas, TNFR1, DR3, DR4, DR5, and DR6 contains intracellular death domain which bind TRAD or FADD. This leads to activation of caspase 8 and apoptosis. Locksley et al. (2001) *Cell* 104: 487-501. However, signaling through death-receptors can also be required for proliferation of hepatocytes and T cells. Strasser et al., (1999) *Intl. J. Biochem. Cell Biol.* 31: 533-537, Yamada et al. (1997), *Proc. Natl. Acad. Of Sci. U.S.A,* 94: 1441-6. The other group including TNFR2, CD40, or CD30 bind TNF-Receptor Associated Factors (TRAFs), molecular adapters that couple these surface receptors to downstream signaling cascades. This leads to activation of JNK and NFKB which can promote cell growth and survival. These proteins therefore play critical roles in morphogenesis, the control of apoptosis, differentiation, or proliferation. TNF/TNFR superfamily proteins are now extensively studied as targets for therapies against many human diseases such as atherosclerosis, allograft rejection, arthritis, and cancer. Locksley et al. (2001), Williams et al. (2000), *Ann. Rhem. Dis.* 59: i75-80.

In addition to the membrane associated receptor molecules described above, a number the receptors belonging to the TNF-receptor supergene family exist as soluble ligand binding proteins. Many of the soluble forms of the transmembrane receptors were subsequently identified as containing only the extracellular ligand binding domain(s) of the receptors. For example, a soluble form of TNF receptor has been found in urine and serum (see U.S. Pat. No. 5,843,789 and Nophar et al., *EMBO J.,* 9(10):3269-3278, 1990), and have been shown to arise by proteolytic cleavage of cell surface TNF-receptors (Wallach et al., *Agents Actions Suppl.,* 35:51-57, 1991). These soluble forms of receptor molecules have been implicated in the modulation of TNF activity by not only interfering with TNF binding to its receptor, but also by stabilizing the TNF structure and preserving its activity, thus prolonging some of its effects (Aderka et al, *Cytokine & Growth Factor Reviews,* 7(3):231-240, 1996).

Members of the tumor necrosis factor superfamilies of ligands and cell-surface receptors regulate immune function and most TNF/TNFR superfamily proteins, such as FASL/ FAS, CD40L/CD40, TNF/TNFR, or LTβ/LTβR to name a few, are expressed in the immune system, where the coordinate immune cell homeostasis, activation induced cell death, T cells priming, functions and survival of dendritic cells, or the formation of germinal centers and lymphoid organs such as Peyer's patches and lymph nodes. Fu et al. (1999), *Ann. Rev. Immunol.* 17: 399-433, Grewal et al. (1998), *Ann. Rev. Immunol.* 166: 111-135. Recently, novel members of this large families have been identified that have critical functions in immunity and couple lymphoid cells with other organ systems such as bone morphogenesis and mammary gland formation in pregnancy.

Because of the crucial role that members of the TNF family of ligands and their receptors (membrane-associated and soluble) play in the immunological system and in a variety of disease processes, a need exists to identify and characterize novel members of these families, for use to improve diagnosis and therapy.

SUMMARY OF THE INVENTION

The present invention relates to novel MK61 nucleic acid molecules and encoded polypeptides.

In accordance with the invention, a number of human MK61 isoforms are described herein: "hMK61T1", "hMK61T2", "hMK61T3", "hMK61T4", "hMK61T5", and "hMK61T6". Additionally, a mouse isoform ("mMK61") and an Fc-fusion polypeptide thereof ("mMK61-Fc" and "hMK61-Fc") are described herein.

The invention provides for an isolated nucleic acid molecule comprising a nucleotide sequence selected from the group consisting of:

(a) the nucleotide sequence as set forth in SEQ ID NO:1, SEQ ID NO:3, SEQ ID NO:5, SEQ ID NO:7, SEQ ID NO:9, SEQ ID NO:11, SEQ ID NO:13, or SEQ ID NO:15;

(b) a nucleotide sequence encoding the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16;

(c) a nucleotide sequence which hybridizes under moderately or highly stringent conditions to the complement of (a) or (b), wherein the encoded polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16; and (d) a nucleotide sequence complementary to any of (a) through (c).

The invention also provides for an isolated nucleic acid molecule comprising a nucleotide sequence selected from the group consisting of:

(a) a nucleotide sequence encoding a polypeptide that is at least about 70, 75, 80, 85, 90, 95, 96, 97, 98 or 99 percent identical to the polypeptide as set forth in SEQ ID NO:2, SEQ ID NO:4, SEQ ID NO:6, SEQ ID NO:8, SEQ ID NO:10, SEQ ID NO:12, SEQ ID NO:14, OR SEQ ID NO:16, wherein the encoded polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16;

(b) a nucleotide sequence encoding an allelic variant or splice variant of the nucleotide sequence as set forth in SEQ ID NO:1, SEQ ID NO:3, SEQ ID NO:5, SEQ ID NO:7, SEQ ID NO:9, SEQ ID NO:11, SEQ ID NO:13, or SEQ ID NO:15, wherein the encoded polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16;

(c) a nucleotide sequence of SEQ ID NO:1, (a), or (b) encoding a polypeptide fragment of at least about 25 amino acid residues, wherein the polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16;

(d) a nucleotide sequence encoding a polypeptide that has at least one amino acid substitution and/or deletion of the amino sequence set forth in any of SEQ ID NO:2, SEQ ID NO:4, SEQ ID NO:6, SEQ ID NO:8, SEQ ID NO:10, SEQ ID NO:12, SEQ ID NO:14, or SEQ ID NO:16, wherein the encoded polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16;

(e) a nucleotide sequence of SEQ ID NO:1, or (a)-(d) comprising a fragment of at least about 16 nucleotides;

(f) a nucleotide sequence which hybridizes under moderately or highly stringent conditions to the complement of any of (a)-(e), wherein the encoded polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, OR SEQ ID NO:16; and (g) a nucleotide sequence complementary to any of (a)-(e).

The invention further provides for an isolated nucleic acid molecule comprising a nucleotide sequence selected from the group consisting of:

(a) a nucleotide sequence encoding a polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16 with at least one conservative amino acid substitution, wherein the encoded polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16;

(b) a nucleotide sequence encoding a polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16 with at least one amino acid insertion, wherein the encoded polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16;

(c) a nucleotide sequence encoding a polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16 with at least one amino acid deletion, wherein the encoded polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16;

(d) a nucleotide sequence encoding a polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16 which has a C- and/or N-terminal truncation, wherein the encoded polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16;

(e) a nucleotide sequence encoding a polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16 with at least one modification selected from the group consisting of amino acid substitutions, amino acid insertions, amino acid deletions, C-terminal truncation, and N-terminal truncation, wherein the encoded polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16;

(f) a nucleotide sequence of (a)-(e) comprising a fragment of at least about 16 nucleotides;

(g) a nucleotide sequence which hybridizes under moderately or highly stringent conditions to the complement of any of (a)-(f), wherein the encoded polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16; and (h) a nucleotide sequence complementary to any of (a)-(e).

The invention also provides for an expression vector comprising the isolated nucleic acid molecules set forth herein; recombinant host cells (eukaryotic and/or prokaryotic) that comprise the vector; the process for producing a h2520 polypeptide comprising culturing the host cell under suitable conditions to express the polypeptide and optionally isolating the polypeptide from the culture; and the isolated polypeptide produced by this process. The nucleic acid molecule used in this process may also comprise promoter DNA other than the promoter DNA for the native MK61 polypeptide operatively linked to the nucleotide sequence encoding the MK61 polypeptide.

The invention also provides for a nucleic acid molecule as described in the previous paragraphs wherein the percent identity is determined using a computer program selected from the group consisting of GAP, BLASTP, BLASTN, FASTA, BLASTA, BLASTX, BestFit, and the Smith-Waterman algorithm.

The present invention provides a process for identifying candidate inhibitors and/or stimulators of MK61 polypeptide activity or production comprising exposing a host cell to the candidate inhibitors and/or stimulators, measuring MK61 polypeptide activity or production in the host cell, and comparing this activity with control cells (i.e., cells not exposed to the candidate inhibitor and/or stimulator). In a related aspect, the invention provides for the inhibitors and/or stimulators identified by any of the preceding methods.

The invention also provides for an isolated polypeptide comprising the amino acid sequence set forth in SEQ ID NO: 2, SEQ ID NO: 4, SEQ ID NO: 6, SEQ ID NO: 8, SEQ ID NO: 10, SEQ ID No: 12, SEQ ID NO: 14 or SEQ. ID NO: 16.

The invention also provides for an isolated polypeptide comprising the amino acid sequence selected from the group consisting of:

(a) the mature amino acid sequence set forth in SEQ ID NO:2, SEQ ID NO:4, SEQ ID NO:6, SEQ ID. NO:8, SEQ ID NO:10, SEQ ID NO:12, SEQ ID NO:14, or SEQ ID NO:16, and optionally further comprising an amino-terminal methionine;

(b) an amino acid sequence for an ortholog of SEQ ID NO:2, SEQ ID NO:4, SEQ ID NO:6, SEQ ID NO:8, SEQ ID NO:10, SEQ ID NO:12, SEQ ID NO:14, or SEQ ID NO:16, wherein the polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16;

(c) an amino acid sequence exhibits at least about 70, 75, 80, 85, 90, 95, 96, 97, 98 or 99 percent identity to the amino acid sequence of SEQ ID NO:2, SEQ ID NO:4, SEQ ID NO:6, SEQ ID NO:8, SEQ ID NO:10, SEQ ID NO:12, SEQ ID NO:14, or SEQ ID NO:16, wherein the polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16 as determined using a computer program selected from the group consisting of GAP, BLASTP, BLASTN, FASTA, BLASTA, BLASTX, BestFit and the Smith-Waterman algorithm.;

(d) a fragment of the amino acid sequence set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16 comprising at least about 25 amino acid residues, wherein the polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16; and (e) an amino acid sequence for an allelic variant or splice variant of either the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, or at least one of (a)-(c) wherein the polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16.

The invention further provides for an isolated polypeptide comprising the amino acid sequence selected from the group consisting of:

(a) the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, with at least one conservative amino acid substitution, wherein the polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16;

(b) the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, with at least one amino acid insertion, wherein the polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16;

(c) the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, with at least one amino acid deletion, wherein the polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16;

(d) the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16 which has a C- and/or N-terminal truncation, wherein the polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16; and (e) the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, with at least one modification selected from the group consisting of amino acid substitutions, amino acid insertions, amino acid deletions, C-terminal truncation, and N-terminal truncation, wherein the polypeptide has an activity of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16.

Analogs of MK61 are provided for in the present invention which result from conservative and non-conservative amino acid substitutions of the MK61 polypeptide of SEQ ID NO: 2, SEQ ID NO: 4, SEQ ID NO: 6, SEQ ID NO:8, SEQ ID NO:10, SEQ ID NO:12, SEQ ID NO:14, or SEQ ID NO:16.

Such analogs include a MK61 polypeptide wherein the amino acid corresponding to position 38, 39 or 51 of SEQ ID NOS: 2, 4, 6, 8, 10 or 12 is cysteine, serine or alanine; a MK61 polypeptide wherein the amino acid corresponding to position 60 or 76 of SEQ ID NOS: 2 or 6 is cysteine, serine or alanine a MK61 polypeptide wherein the amino acid corresponding to position 41, 42, 54, 63 or 79 of SEQ ID NOS: 14 or 16 is cysteine, serine or alanine; a MK61 polypeptide wherein the amino acid corresponding to position 171 or 172 of SEQ ID NO: 2 is leucine, norleucine, valine, methionine, alanine or phenylalanine; a MK61 polypeptide wherein the amino acid corresponding to position 178 or 180 of SEQ ID NOS: 14 or 16 is leucine, norleucine, valine, methionine, alanine or phenylalanine; a MK61 polypeptide wherein the amino acid corresponding to position 141 of SEQ ID NOS: 14 or 16 is glycine, proline or alanine.

The invention also provides methods of inhibiting MK61 receptor and/or ligand activity in a mammal, which comprises administering at least one polypeptide set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16.

Also provided are fusion polypeptides comprising the amino acid sequences of (a)-(e) above. In addition, the invention encompasses fusion polypeptides comprising the amino acid sequences of SEQ ID NO: 16, SEQ ID NO: 36 and SEQ ID NO: 39.

The present invention also provides for an expression vector comprising the isolated nucleic acid molecules as set forth herein, recombinant host cells comprising recombinant nucleic acid molecules as set forth herein, and a method of producing an MK61 polypeptide comprising culturing the host cells and optionally isolating the polypeptide so produced.

A transgenic non-human animal comprising a nucleic acid molecule encoding an MK61 polypeptide is also encompassed by the invention. The MK61 nucleic acid molecules are introduced into the animal in a manner that allows expression and increased levels of the MK61 polypeptide, which may include increased circulating levels. The transgenic non-human animal is preferably a mammal.

Also provided are derivatives of the MK61 polypeptides of the present invention.

The present invention further provides for an antibody or fragment thereof that specifically binds an MK61 polypeptide as set forth herein. This antibody can be polyclonal or monoclonal, and can be produced by immunizing an animal with a peptide comprising an amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16.

Also provided is the hybridoma that produces a monoclonal antibody that binds to a peptide comprising an amino acid sequence of SEQ ID NO: 2

The present invention also provides for a method of detecting or quantitating the amount of MK61 polypeptide in a sample comprising contacting a sample suspected of containing MK61 polypeptide with the anti-MK61 antibody or antibody fragment set forth herein and detecting the binding of said antibody or antibody fragment.

Additionally provided by the invention are selective binding agents or fragments thereof that are capable of specifically binding the MK61 polypeptides, derivatives, variants, and fragments (preferably having sequences of at least about 25 amino acids) thereof. These selective binding agents may be antibodies such as humanized antibodies, human antibodies, polyclonal antibodies, monoclonal antibodies, chimeric antibodies, complementarity determining region (CDR)-grafted antibodies, anti-idiotypic antibodies, and fragments thereof. Furthermore, the selective binding agents may be antibody variable region fragments, such as Fab or Fab' fragments, or fragments thereof, and may comprise at least one complementarity determining region with specificity for a MK61 polypeptide set forth herein. The selective binding agent may also be bound to a detectable label, such as a radiolabel, a fluorescent label, an enzyme label, or any other label known in the art. Further, the selective binding agent may antagonize MK61 polypeptide biological activity, and/or be produced by immunizing an animal with a MK61 polypeptide as set forth herein.

The present invention also provides for a hybridoma that produces a selective binding agent capable of binding MK61 polypeptide as set forth herein.

Also provided is a method for treating, preventing, or ameliorating a disease, condition, or disorder comprising administering to a patient an effective amount of a selective binding agent as set forth herein. An effective amount, or a therapeutically effective amount, is an amount sufficient to result in a detectable change in the course or magnitude of the disease, condition or disorder, such as the intensity or duration of presentment of any symptom associated therewith.

Pharmaceutical compositions comprising the above-described nucleic acid molecules, polypeptides or selective binding agents and one or more pharmaceutically acceptable formulation agents are also encompassed by the invention. The pharmaceutical acceptable formulation agent may be a carrier, adjuvant, soubilizer, stabilizer, or anti-oxidant. The nucleic acid molecules of the present invention may be contained in viral vectors. The compositions are used to provide therapeutically effective amounts of the nucleic acid molecules or polypeptides of the present invention. The invention is also directed to methods of using the polypeptides, nucleic acid molecules, and selective binding agents.

Also provided are derivatives of the MK61 polypeptides of the present invention. These polypeptides may be covalently modified with a water-soluble polymer wherein the water-soluble polymer is selected from the group consisting of polyethylene glycol, monomethoxy-polyethylene glycol, dextran, cellulose, poly-(N-vinyl pyrrolidone) polyethylene glycol, propylene glycol homopolymers, polypropylene oxide/ethylene oxide co-polymers, polyoxyethylated polyols, and polyvinyl alcohol.

The present invention also provides for fusion polypeptides comprising the polypeptide sequences set forth herein fused to a heterologous amino acid sequence, which may be an IgG constant domain or fragment thereof.

Methods for treating, preventing or ameliorating a medical condition, such as cancer, in a mammal resulting from decreased levels of MK61 polypeptide are also included in the present invention. These methods include administering to a patient a therapeutically effective amount of an antagonist selected from the group consisting of selective binding agents, small molecules, peptides, peptide derivatives and antisense oligonucleotides. These medical conditions may include those characterized by immune system stimulation such as autoimmune diseases and leukemias and lymphomas.

Methods for treating, preventing or ameliorating a medical condition in a mammal resulting from increased levels of MK61 polypeptide are also included in the present invention. These methods comprise administering to a patient a therapeutically effective amount of a MK61 polypeptide; a nucleic acid molecule encoding a MK61 polypeptide; or a nucleic acid molecule comprising elements that regulate or modulate the expression of a MK61 polypeptide. Examples of these methods include gene therapy and cell therapy and are further described herein. These medical conditions may include those characterized by immune system suppression such as AIDs and cancers.

The invention encompasses methods of diagnosing a pathological condition or a susceptibility to a pathological condition in a subject caused by or resulting from abnormal levels of MK61 polypeptide comprising determining the presence or amount of expression of the MK61 polypeptide in a biological, tissue, or cellular sample; and comparing the level of said polypeptide in a biological, tissue, or cellular sample from either normal subjects or the subject at a different time, wherein susceptibility to a pathological condition is based on the presence or amount of expression of the polypeptide.

The MK61 polypeptides and nucleic acid molecules of the present invention may be used to treat, prevent, ameliorate and/or detect diseases and disorders, including those recited herein.

The present invention also provides a method of identifying coumpounds which bind to a MK61 polypeptide. The method comprises contacting an MK61 polypeptide with a test molecule and determining the extent of binding of the test molecule to the polypeptide. The method may further comprise determining whether such test molecules are agonists or antagonists of an MK61 polypeptide. The present invention further provides a method of testing the impact of molecules on the expression of an MK61 polypeptide or on the activity of an MK61 polypeptide.

Methods of regulating expression and modulating (i.e., increasing or decreasing) levels of an MK61 polypeptide are also encompassed by the invention. One method comprises administering to an animal a nucleic acid molecule encoding an MK61 polypeptide. In another method, a nucleic acid molecule comprising elements that regulate or modulate the expression of an MK61 polypeptide may be administered. Examples of these methods include gene therapy, cell therapy and anti-sense therapy as further described herein.

The present invention further provides a method of modulating levels of a MK61 polypeptide in an animal comprising administering to the animal the nucleic acid molecule set forth herein.

A transgenic non-human animal comprising a nucleic acid molecule encoding a MK61 polypeptide is also encompassed by the invention. The MK61 nucleic acid molecule is introduced into the animal in a manner that allows expression and increased levels of the MK61 polypeptide, which may include increased circulating levels. The transgenic non-human animal is preferably a mammal.

The present invention provides for a diagnostic reagent comprising a detectably labeled polynucleotide encoding the amino acid sequence set out in SEQ ID NO: 2, or a fragment, variant or homolog thereof, including allelic variants and spliced variants thereof. The detectably labeled polynucleotide may be a first-strand cDNA, DNA, or RNA.

The invention also provides a method for detecting the presence of MK61 nucleic acid molecules in a biological sample comprising the steps of:

(a) providing a biological sample suspected of containing MK61 nucleic acid molecules;

(b) contacting the biological sample with a diagnostic reagent under conditions wherein the diagnostic reagent will hybridize with MK61 nucleic acid molecules contained in said biological sample;

(c) detecting hybridization between MK61 nucleic acid molecules in the biological sample and the diagnostic reagent; and (d) comparing the level of hybridization between the biological sample and diagnostic reagent with the level of hybridization between a known concentration of MK61 nucleic acid molecules and the diagnostic reagent.

The invention also provides a method for detecting the presence of MK61 nucleic acid molecules in a tissue or cellular sample comprising the steps of:

(a) providing a tissue or cellular sample suspected of containing MK61 nucleic acid molecules;

(b) contacting the tissue or cellular sample with a diagnostic reagent under conditions wherein the diagnostic reagent will hybridize with MK61 nucleic acid molecules;

(c) detecting hybridization between MK61 nucleic acid molecules in the tissue or cellular sample and the diagnostic reagent; and (d) comparing the level of hybridization between the tissue or cellular sample and diagnostic reagent with the level of hybridization between a known concentration of MK61 nucleic acid molecules and the diagnostic reagent.

The invention provides for methods of inhibiting MK61 receptor activity in a mammal comprising administering at least one of the amino acid sequences selected from the group consisting of SEQ ID NOS: 2, 4, 6, 8, 10, 12, 14, 16, 36 and 38.

The invention provides for methods of inhibiting MK61 ligand activity in a mammal comprising administering at least one of the amino acid sequences selected from the group consisting of SEQ ID NOS: 2, 4, 6, 8, 10, 12, 14, 16, 36 and 38.

The invention provides for methods of stimulating an immune response in a mammal by administering a negative regulator of MK61 receptor signaling. A negative regulator is a molecule which inhibits the signaling of the MK61 receptor. Negative regulators include but are not limited to fusion proteins, such as those set out in SEQ ID NOS: 16, 36 and 39, antibodies, small molecules, peptides and peptide derivatives.

The invention also provides for methods of inhibiting an immune response comprising administering a positive regulator or MK61 receptor signaling. A positive regulator is a molecule which activates the signaling of MK61 receptor. Positive regulators include MK61 ligands and agonistic antibodies.

The invention provides for methods of stimulating reverse signaling through a cell surface bound MK61 ligand comprising a positive regulator of MK61 ligand reverse signaling. The positive regulators include but are not limited to MK61 fusion proteins, antibodies, small molecules and peptide derivatives. The term "reverse signaling" refers to activation of cellular signaling induced by a molecule binding to a cell surface bound ligand such as binding by the ligand's receptor or an anti-ligand antibody.

The invention also provides for methods of inhibiting reverse signaling through a cell surface bound MK61 ligand comprising a negative regulator of MK61 ligand reverse signaling. The negative regulators include but are not limited to MK61 fusion proteins, antibodies, small molecules and peptide derivatives.

The invention provides for methods of treating a B cell or T cell lymphoproliferative disorder, an autoimmune disease or an inflammatory disease in a mammal comprising administering a therapeutically effective amount of MK61-Fc fusion protein, an anti-MK-61 antibody, an antisense oligonucleotide, a MK61 ligand, or a anti-MK61 ligand antibody to said mammal. The lymphoproliferative diseases that may be treated include but are not limited to myeloma; B lymphoma, leukemia; and non-hodgkins lymphoma. The autoimmune diseases include but are not limited to rheumatoid arthritis, systemic lupus erythematosus, intestinal bowel disease and Crohn's Disease. The inflammatory diseases include but are not limited to rheumatoid arthritis, sepsis, intestinal bowel disease and Crohn's Disease.

The invention also encompasses a polypeptide fragment having an amino acid sequence comprising the cysteine rich domain residues 26-60 of SEQ ID NO: 36. The cysteine rich domain matches the TNFR superfamily cysteine-rich region signature as defined in Madry et. al (Intl. Immunol. 10:1693-1702, 1998) and references therein and is expected to encompass the MK61 ligand-binding domain.

The MK61 polypeptides can be used for identifying ligands thereof. Various forms of "expression cloning" have been used for cloning ligands for receptors, see e.g., Davis et al., *Cell*, 87:1161-1169 (1996). These and other MK61 ligand cloning experiments are described in greater detail herein. Isolation of the MK61 ligand(s) allows for the identification or development of novel agonists and/or antagonists of the MK61 signaling pathway. Such agonists and antagonists include MK61 ligand(s), anti-MK61 ligand antibodies and derivatives thereof, small molecules, carbohydrates, lipid, polynucleotides (including antisense oligonucleotides), any of which can be used for potentially treating one or more diseases or disorders, including those recited herein.

BRIEF DESCRIPTION OF THE FIGURES

It will be understood that in the figures described below, the nucleotides 5' to those nucleotides encoding the signal peptide are part of the 5'-untranslated (5'-UTR) flanking sequence. Additionally, nucleotides 3' to the stop codon represent the 3'-untranslated (3'-UTR) sequence.

FIG. 1 depicts a nucleic acid sequence (SEQ ID NO:1) encoding human MK61T1 (hMK61T1). Also depicted is the amino acid sequence (SEQ ID NO:2) of human hMK61T1. hMK61T1 is a cell surface receptor which contains a signal peptide (SP), one TNFr type cysteine rich domain (CRD), spacer, transmembrane domain (TM), and a long intracellular domain with two regions highly conserved between species. The predicted signal peptide is underlined in this figure, and the stop codon in SEQ ID NO:1 is double-underlined.

FIG. 2 depicts a nucleic acid sequence (SEQ ID NO:3) encoding human MK61T2 (hMK61T2), believed to be a soluble receptor. Also depicted is the amino acid sequence (SEQ ID NO:4) of human hMK61T2. The predicted signal peptide is underlined in this figure, and the stop codon in SEQ ID NO:3 is double-underlined.

FIG. 3 depicts a nucleic acid sequence (SEQ ID NO:5) encoding human MK61T3 (hMK61T3). Also depicted is the amino acid sequence (SEQ ID NO:6) of human hMK61T3. hMK61T3 is believed to be a soluble receptor, having a signal peptide and TNFr-type CRD. The predicted signal peptide is underlined in this figure, and the stop codon in SEQ ID NO:5 is double-underlined.

FIG. 4 depicts a nucleic acid sequence (SEQ ID NO:7) and amino acid sequence (SEQ ID NO:8) encoding human MK61T4 (hMK61T4), believed to be a soluble receptor. The predicted signal peptide is underlined in this figure, and the stop codon in SEQ ID NO:7 is double-underlined.

FIG. 5 depicts a nucleic acid sequence (SEQ ID NO:9) and amino acid sequence (SEQ ID NO:10) encoding human MK61T5 (hMK61T5), believed to be a soluble receptor. The predicted signal peptide is underlined in this figure, and the stop codon in SEQ ID NO:9 is double-underlined.

FIG. 6 depicts a nucleic acid sequence (SEQ ID NO:11) and amino acid sequence (SEQ ID NO:12) encoding human MK61T6 (hMK61T6), believed to be a soluble receptor. The predicted signal peptide is underlined in this figure, and the stop codon in SEQ ID NO:11 is double-underlined.

FIG. 7 depicts the nucleic acid sequence (SEQ ID NO:13) and amino acid sequence (SEQ ID NO:14) encoding mouse MK61 (mMK61), also called "Smil2-00051-F3", or "Smil2-00051". In this figure, the predicted signal peptide is underlined, and the stop codon in SEQ ID NO:13 is double-underlined.

FIG. 8 depicts the nucleic acid sequence (SEQ ID NO:15) and amino acid sequence (SEQ ID NO:16) encoding the mouse mMK61-Fc fusion polypeptide (mMK61-Fc). In this figure, the predicted signal peptide is underlined, the Fc portion of the sequence is double-underlined, the NotI restrict site for joining MK61 to Fc is in bold, and the Kozak consensus sequence (which is not translated) is in italics.

FIG. 10 sets forth an amino acid comparison of mMK61 (SEQ ID NO:14) with an OPG receptor, Mrank, (SEQ ID NO:17), a known TNFr family member. Mrank is the mouse OPG (osteoprotegerin) receptor precursor.

FIG. 11 sets forth an amino acid comparison of mMK61 (SEQ ID NO:14) with the Fas ligand receptor (mfas), (SEQ ID NO:18). mfas is an apoptosis-mediating surface antigen receptor precursor.

FIG. 12 sets forth an amino acid comparison of mMK61 (SEQ ID NO:14) with a known mouse lymphotoxin-beta receptor (Tnfrc), SEQ ID NO.:19. Tnfrc is a lymphotoxin-beta receptor precursor, and is also called "tumor necrosis factor receptor 2 related protein" or "tumor necrosis factor-c receptor precursor".

FIG. 20 depicts the histological analysis of the spleens of MK61-Fc treated mice. The histological analysis indicated the presence of lymphoid hyperplasia.

FIG. 24 sets out the amino acid sequence of the human MK61-delta Fc CHO (SEQ ID NO: 36).

FIG. 25 sets out the amino acid sequence of the human MK61-Fc CHO (SEQ ID NO: 39).

DETAILED DESCRIPTION OF THE INVENTION

Figure 9:
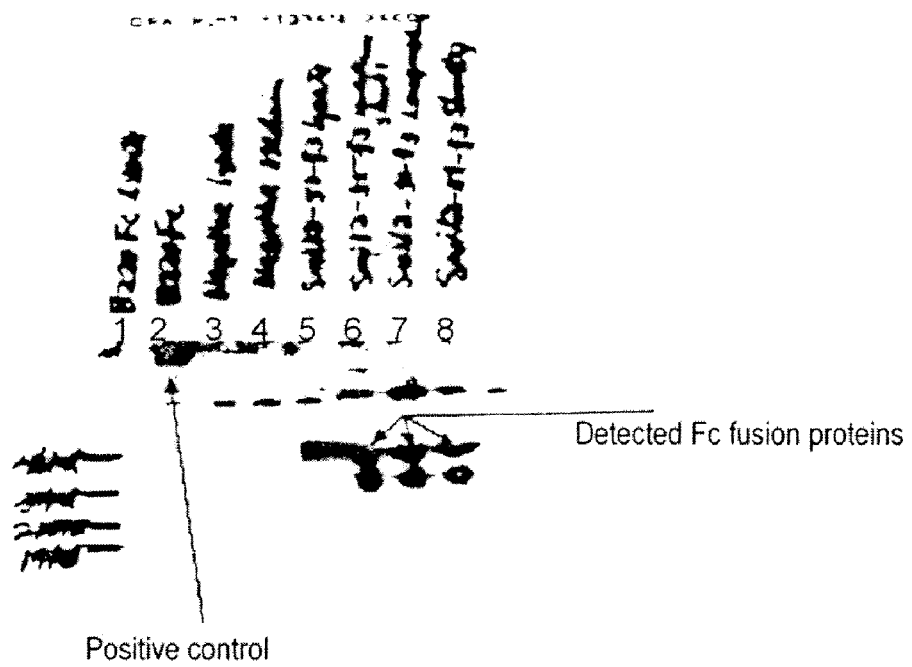
FIG. 9 sets forth a Western Blot showing that the mMK61 Fc fusion protein (mMK61-Fc) is capable of being secreted from mammalian cells.

The section headings used herein are for organizational purposes only and are not to be construed as limiting the subject matter described. All references cited in this application are expressly incorporated by reference herein.

The hMK61T1 isoform is a cell-surface receptor having a signal peptide, a TNF receptor (TNFR) cysteine rich domain (CRD), a transmembrane domain (TM), and a long and highly conserved intracellular domain.

The remaining five human isoforms (hMK61T2, hMK61T3, hMK61T4, hMK61TS, and hMK61T6) are believed to be soluble receptor forms of MK61. hMK61T3 and hMK61T5 each contain a complete TNFr CRD, and are likely naturally-occurring inhibitors of the hMK61T1 mediated signal transduction. The hMK61T2, hMK61T4, and hMK61T6 isoforms each contain partial CRD's.

mMK61 is a mouse MK61 isoform, and mMK61-Fc is an Fc-fusion polypeptide thereof.

Definitions

The terms "MK61 gene" or "MK61 nucleic acid molecule" or "polynucleotide" refers to a nucleic acid molecule comprising or consisting of a nucleotide sequence as set forth in SEQ ID NO:1, SEQ ID NO:3, SEQ ID NO:5, SEQ ID NO:7, SEQ ID NO:9, SEQ ID NO:11, SEQ ID NO:13, or SEQ ID NO:15, a nucleotide sequence encoding the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, and nucleic acid molecules as defined herein.

The term "MK61 polypeptide" refers to a polypeptide comprising the amino acid sequence of SEQ ID NO:2, SEQ ID NO:4, SEQ ID NO:6, SEQ ID NO:8, SEQ ID NO:10, SEQ ID NO:12, SEQ ID NO:14, or SEQ ID NO:16, and related polypeptides. Related polypeptides include: MK61 polypeptide allelic variants, MK61 polypeptide orthologs, MK61 polypeptide splice variants, MK61 polypeptide variants and MK61 polypeptide derivatives. MK61 polypeptides may be mature polypeptides, as defined herein, and may or may not have an amino terminal methionine residue, depending on the method by which they are prepared.

The term "MK61 polypeptide allelic variant" refers to the polypeptide encoded by one of several possible naturally occurring alternate forms of a gene occupying a given locus on a chromosome of an organism or a population of organisms.

The term "MK61 polypeptide derivatives" refers to a polypeptide having the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, MK61 polypeptide allelic variants, MK61 polypeptide orthologs, MK61 polypeptide splice variants, or MK61 polypeptide variants, as defined herein, that have been chemically modified.

The term "MK61 polypeptide fragment "refers to a polypeptide that comprises a truncation at the amino terminus (with or without a leader sequence) and/or a truncation at the carboxy terminus of the polypeptide whose sequence is as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, MK61 polypeptide allelic variants, MK61 polypeptide orthologs, MK61 polypeptide splice variants and/or an MK61 polypeptide variant having one or more amino acid additions or substitutions or internal deletions (wherein the resulting polypeptide is at least six (6) amino acids or more in length) as compared to the MK61 polypeptide amino acid sequence set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16. MK61 polypeptide fragments may result from alternative RNA splicing or from in vivo protease activity. For transmembrane or membrane-bound forms of the MK61 polypeptides, preferred fragments include soluble forms such as those lacking a transmembrane or membrane-binding domain.

In preferred embodiments, truncations comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, about 50 amino acids, or about 75 amino acids, or about 100 amino acids, or about 150 amino acids, or about 200 amino acids. Such MK61 polypeptide fragments may optionally comprise an amino terminal methionine residue. It will be appreciated that such fragments can be used, for example, to generate antibodies to MK61 polypeptides.

The term "MK61 fusion polypeptide" refers to a fusion of one or more amino acids (such as a heterologous peptide or polypeptide) at the amino or carboxy terminus of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, MK61 polypeptide allelic variants, MK61 polypeptide orthologs, MK61 polypeptide splice variants, or MK61 polypeptide variants having one or more amino acid deletions, substitutions or internal additions as compared to the MK61 polypeptide amino acid sequence set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16.

The term "MK61 polypeptide ortholog" refers to a polypeptide from another species that corresponds to an MK61 polypeptide amino acid sequence as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16. For example, mouse and human MK61 polypeptides are considered orthologs of each other.

The term "MK61 polypeptide splice variant" refers to a nucleic acid molecule, usually RNA, which is generated by alternative processing of intron sequences in an RNA primary transcript containing the non-contiguous coding region of the MK61 polypeptide amino acid sequence as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16.

The term "MK61 polypeptide variants" refers to MK61 polypeptides comprising amino acid sequences having one or more amino acid sequence substitutions, deletions (such as internal deletions and/or MK61 polypeptide fragments), and/or additions (such as internal additions and/or MK61 fusion polypeptides) as compared to the MK61 polypeptide amino acid sequences set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16 (with or without a leader sequence). Variants may be naturally occurring (e.g., MK61 polypeptide allelic variants, MK61 polypeptide orthologs and MK61 polypeptide splice variants) or may be artificially constructed. Such MK61 polypeptide variants may be prepared from the corresponding nucleic acid molecules having a DNA sequence that varies accordingly from the DNA sequence as set forth in SEQ ID NO:1, SEQ ID NO:3, SEQ ID NO:5, SEQ ID NO:7, SEQ ID NO:9, SEQ ID NO:11, SEQ ID NO:13, or SEQ ID NO:15. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

The term "antigen" refers to a molecule or a portion of a molecule capable of being bound by a selective binding agent, such as an antibody, and additionally capable of being used in an animal to produce antibodies capable of binding to an epitope of each antigen. An antigen may have one or more epitopes.

The term "biologically active MK61 polypeptides" refers to MK61 polypeptides having at least one activity characteristic of the polypeptide comprising the amino acid sequence of SEQ ID NO:2, SEQ ID NO:4, SEQ ID NO:6, SEQ ID NO:8, SEQ ID NO:10, SEQ ID NO:12, SEQ ID NO:14, or SEQ ID NO:16.

The terms "effective amount" and "therapeutically effective amount" each refer to the amount of a MK61 polypeptide or MK61 nucleic acid molecule used to support an observable level of one or more biological activities of the MK61 polypeptides as set forth herein.

The term "expression vector" refers to a vector which is suitable for use in a host cell and contains nucleic acid sequences which direct and/or control the expression of heterologous nucleic acid sequences. Expression includes, but is not limited to, processes such as transcription, translation, and RNA splicing, if introns are present.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "identity" as known in the art refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept but, in contrast to "identity", refers to a measure of similarity which includes both identical matches and conservative substitution matches. If two polypeptide sequences have, for example, 10/20 identical amino acids, and the remainder are all non-conservative substitutions, then the percent identity and similarity would both be 50%. If, in the same example, there are five more positions where there are conservative substitutions, then the percent identity remains 50%, but the percent similarity would be 75% (15/20). Therefore, in cases where there are conservative substitutions, the degree of percent similarity between two polypeptides will be higher than the percent identity between those two polypeptides.

The term "isolated nucleic acid molecule" refers to a nucleic acid molecule of the invention that (1) has been separated from at least about 50 percent of proteins, lipids, carbohydrates or other materials with which it is naturally found when total DNA is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "isolated polypeptide" refers to a polypeptide of the present invention that (1) has been separated from at least about 50 percent of polynucleotides, lipids, carbohydrates or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "mature MK61 polypeptide" refers to an MK61 polypeptide lacking a leader sequence. A mature MK61 polypeptide may also include other modifications such as proteolytic processing of the amino terminus (with or without a leader sequence) and/or the carboxy terminus, cleavage of a smaller polypeptide from a larger precursor, N-linked and/or O-linked glycosylation, and the like.

An exemplary mature MK61 polypeptide is depicted by amino acid residue 24 through amino acid residue 355 of SEQ ID NO:2; by amino acid residue 24 through amino acid residue 85 of SEQ ID NO:4; by amino acid residue 24 through amino acid residue 136 of SEQ ID NO:6; by amino acid residue 24 through amino acid residue 187 of SEQ ID NO:8; by amino acid residue 24 through amino acid residue 71 of SEQ ID NO:10; by amino acid residue 24 through amino acid residue 167 of SEQ ID NO:12; by amino acid residue 22 through amino acid residue 345 of SEQ ID NO:14; and by amino acid residue 22 through amino acid residue 404 of SEQ ID NO:16.

The terms "nucleic acid sequence" or "nucleic acid molecule" refer to a DNA or RNA sequence. The terms encompass molecules formed from any of the known base analogs of DNA and RNA such as, but not limited to 4-acetylcytosine, 8-hydroxy-N6-methyladenine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "naturally occurring" or "native" when used in connection with biological materials such as nucleic acid molecules, polypeptides, host cells, and the like, refer to materials which are found in nature and are not manipulated by man. Similarly, "non-naturally occurring" or "non-native" as used herein refers to a material that is not found in nature or that has been structurally modified or synthesized by man.

The term "operably linked" is used herein to refer to a method of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably linked" to the coding sequence.

The terms "pharmaceutically acceptable carrier" or "physiologically acceptable carrier" as used herein refer to one or more formulation materials suitable for accomplishing or enhancing the delivery of the MK61 polypeptide, MK61 nucleic acid molecule or MK61 selective binding agent as a pharmaceutical composition.

The term "selective binding agent" refers to a molecule or molecules having specificity for an MK61 polypeptide. As used herein the terms, "specific" and "specificity" refer to the ability of the selective binding agents to bind to human MK61 polypeptides and not to bind to human non-MK61 polypeptides. It will be appreciated, however, that the selective binding agents may also bind orthologs of the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, that is, interspecies versions thereof, such as mouse and rat polypeptides.

The term "transduction" is used to refer to the transfer of nucleic acids from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, for example, Graham et al., *Virology*, 52:456 (1973); Sambrook et al., *Molecular Cloning, a Laboratory Manual*, Cold Spring Harbor Laboratories, New York, (1989); Davis et al., *Basic Methods in Molecular Biology*, Elsevier, (1986); and Chu et al., *Gene*, 13:197 (1981). Such techniques can be used to introduce one or more exogenous DNA moieties into suitable host cells.

The term "transformation" as used herein refers to a change in a cells genetic characteristics, and a cell has been transformed when it has been modified to contain new DNA. For example, a cell is transformed where it is genetically modified from its native state. Following transfection or transduction, the transforming DNA may recombine with that of the cell by physically integrating into a chromosome of the cell, it may be maintained transiently as an episomal element without being replicated, or it may replicate independently as a plasmid. A cell is considered to have been stably transformed when the DNA is replicated with the division of the cell.

The term "vector" is used to refer to any molecule (e.g., nucleic acid, plasmid or virus) used to transfer coding information to a host cell.

Relatedness of Nucleic Acid Molecules and/or Polypeptides

It is understood that related nucleic acid molecules include allelic or splice variants of the nucleic acid molecule of SEQ ID NO:1, SEQ ID NO:3, SEQ ID NO:5, SEQ ID NO:7, SEQ ID NO:9, SEQ ID NO:11, SEQ ID NO:13, or SEQ ID NO:15, and include sequences which are complementary to any of the above nucleotide sequences. Related nucleic acid molecules also include a nucleotide sequence encoding a polypeptide comprising or consisting essentially of a substitution, modification, addition and/or deletion of one or more amino acid residues compared to the polypeptide in SEQ ID NO:2, SEQ ID NO:4, SEQ ID NO:6, SEQ ID NO:8, SEQ ID NO:10, SEQ ID NO:12, SEQ ID NO:14, or SEQ ID NO:16.

Fragments include molecules which encode a polypeptide of at least about 25 amino acid residues, or about 50, or about 75, or about 100, or greater than about 100, amino acid residues of the polypeptide of SEQ ID NO:2.

In addition, related MK61 nucleic acid molecules include those molecules which comprise nucleotide sequences which hybridize under moderately or highly stringent conditions as defined herein with the fully complementary sequence of the nucleic acid molecule of SEQ ID NO:1, SEQ ID NO:3, SEQ ID NO:5, SEQ ID NO:7, SEQ ID NO:9, SEQ ID NO:11, SEQ ID NO:13, or SEQ ID NO:15, or of a molecule encoding a polypeptide, which polypeptide comprises the amino acid sequence as shown in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, or of a nucleic acid fragment as defined herein, or of a nucleic acid fragment encoding a polypeptide as defined herein. Hybridization probes may be prepared using the MK61 sequences provided herein to screen cDNA, genomic or synthetic DNA libraries for related sequences. Regions of the DNA and/or amino acid sequence of MK61 polypeptide that exhibit significant identity to known sequences are readily determined using sequence alignment algorithms as described herein, and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength and the concentration of denaturing agents such as formamide. Examples of "highly stringent conditions" for hybridization and washing are 0.015M sodium chloride, 0.0015M sodium citrate at 65-68° C. or 0.015M sodium chloride, 0.0015M sodium citrate, and 50% formamide at 42° C. See Sambrook, Fritsch & Maniatis, Molecular Cloning: A Laboratory Manual, $2^{nd}$ Ed., Cold Spring Harbor Laboratory, Cold Spring Harbor, N.Y. (1989) and Anderson et al., Nucleic Acid Hybridization: a practical approach, Ch. 4, IRL Press Limited, Oxford, England (1985).

More stringent conditions (such as higher temperature, lower ionic strength, higher formamide, or other denaturing agent) may also be used; however, the degree of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate ($NaDodSO_4$ or SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., Nucleic Acid Hybridization: a Practical Approach, Ch. 4, IRL. Press Limited, Oxford, England (1985).

Factors affecting the stability of a DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(°C.)=81.5+16.6(\log [Na+])+0.41(\% G+C)-600/N-0.72(\% \text{ formamide})$$

where N is the length of the duplex formed in nucleotides, [Na+] is the molar concentration of the sodium ion in the hybridization or washing solution, and % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015M sodium chloride, 0.0015M sodium citrate at 50-65° C. or 0.015M sodium chloride, 0.0015M sodium citrate, and 20% formamide at 37-50° C. By way of example, a "moderately stringent" condition of 50° C. in 0.015 M sodium ion will allow about a 21% mismatch.

It will be appreciated by those skilled in the art that there is no absolute distinction between highly" and "moderately" stringent conditions. For example, at 0.015M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nucleotides is given by:

$$Tm=2° C. \text{ per A-T base pair}+4° C. \text{ per G-C base pair}$$

*The sodium ion concentration in 6×salt sodium citrate (SSC) is 1M. See Suggs et al., Developmental Biology Using Purified Genes, p. 683, Brown and Fox (eds.) (1981).

High stringency washing conditions for oligonucleotides are usually at a temperature of 0-5° C. below the Tm of the oligonucleotide in 6×SSC, 0.1% SDS for longer oligonucleotides.

In another embodiment, related nucleic acid molecules comprise or consist of a nucleotide sequence that is about 70 percent (70%) identical to the nucleotide sequence as shown in SEQ ID NO:1, SEQ ID NO:3, SEQ ID NO:5, SEQ ID NO:7, SEQ ID NO:9, SEQ ID NO:11, SEQ ID NO:13, or SEQ ID NO:15, or comprise or consist essentially of a nucleotide sequence encoding a polypeptide that is about 70 percent (70%) identical to the polypeptide as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16. In preferred embodiments, the nucleotide sequences are about 75 percent, or about 80 percent, or about 85 percent, or about 90 percent, or about 95, 96, 97, 98, or 99 percent identical to the nucleotide sequence as shown in SEQ ID NO:1, or the nucleotide sequences encode a polypeptide that is about 75 percent, or about 80 percent, or about 85 percent, or about 90 percent, or about 95, 96, 97, 98, or 99 percent identical to the polypeptide sequence as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16.

Differences in the nucleic acid sequence may result in conservative and/or non-conservative modifications of the amino acid sequence relative to the amino acid sequence of SEQ ID NO:2, SEQ ID NO:4, SEQ ID NO:6, SEQ ID NO:8, SEQ ID NO:10, SEQ ID NO:12, SEQ ID NO:14, or SEQ ID NO:16.

Conservative modifications to the amino acid sequence of SEQ ID NO:2, SEQ ID NO:4, SEQ ID NO:6, SEQ ID NO:8, SEQ ID NO:10, SEQ ID NO:12, SEQ ID NO:14, or SEQ ID NO:16 (and corresponding modifications to the encoding nucleotides) will produce MK61 polypeptides having functional and chemical characteristics similar to those of a naturally occurring MK61 polypeptide. In contrast, substantial modifications in the functional and/or chemical characteristics of MK61 polypeptides may be accomplished by selecting substitutions in the amino acid sequence of SEQ ID NO:2, SEQ ID NO:4, SEQ ID NO:6, SEQ ID NO:8, SEQ ID NO:10, SEQ ID NO:12, SEQ ID NO:14, or SEQ ID NO:16 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues which are typically incorporated by chemical peptide synthesis rather than by synthesis in biological systems. These include peptidomimetics and other reversed or inverted forms of amino acid moieties.

Naturally occurring residues may be divided into classes based on common side chain properties:

1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human MK61 polypeptide that are homologous, or similar, with non-human MK61 polypeptide orthologs, or into the non-homologous regions of the molecule.

In making such changes, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mcl. Biol.*, 157:105-131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functional equivalent protein or peptide thereby created is intended, in part, for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the MK61 polypeptide, or to increase or decrease the affinity of the MK61 polypeptides for their substrates, described herein.

Exemplary amino acid substitutions are set forth in Table I.

TABLE I

| Amino Acid Substitutions | | |
|---|---|---|
| Original Residues | Exemplary Substitutions | Preferred Substitutions |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diaminobutyric Acid, Gln, Asn | Arg |

TABLE I-continued

| Amino Acid Substitutions | | |
|---|---|---|
| Original Residues | Exemplary Substitutions | Preferred Substitutions |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in SEQ ID NO:2 using well-known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of an MK61 polypeptide to such similar polypeptides. With such a comparison, one can identify residues and portions of the molecules that are conserved among similar polypeptides. It will be appreciated that changes in areas of an MK61 polypeptide that are not conserved relative to such similar polypeptides would be less likely to adversely affect the biological activity and/or structure of the MK61 polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in an MK61 polypeptide that correspond to amino acid residues which are important for activity or structure in similar polypeptides. One skilled in the art may opt for chemically similar amino acid substitutions for such predicted important amino acid residues of MK61 polypeptides.

One skilled in the art can also analyze the three-dimensional structure and amino acid sequence in relation to that structure in similar polypeptides. In view of such information, one skilled in the art may predict the alignment of amino acid residues of an MK61 polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays know to those skilled in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

The MK61 polypeptide analogs of the invention can be determined by comparing the amino acid sequence of MK1 polypeptides with related family members. Exemplary MK61 polypeptide-related family members may include, but are not limited to TNF receptor family members such as Mrank (SEQ ID NO: 17), Fas ligand receptor family members such as Mfasr(SEQ ID NO: 18), and lymphotoxin-beta receptor family members such as TNFrc (SEQ ID NO: 19). This comparison can be accomplished by using a Pileup alignment (Wisconsin GCG Program Package, ver. 8.1; as shown in FIGS. 10, 11 and 12) or an equivalent (overlapping) comparison with multiple family members within conserved and non-conserved regions. As shown in FIGS. 10-12, the predicted amino acid sequence of a mMK61 polypeptide (SEQ ID NO: 14) is aligned with the known amino acid sequences of Mrank (SEQ ID NO: 17), Mfasr (SEQ ID NO: 18) and Tnfrc (SEQ ID NO: 19), respectively.

Other MK61 polypeptide analogs can be identified using these or other methods known to those of skill in the art. These overlapping sequences provide guidance for conservative and non-conservative amino acids substitutions resulting in additional MK61 analogs. It will be appreciated that these amino acid substitutions can consist of naturally occurring or non-naturally occurring amino acids. For example, the alignments depicted in FIGS. 10-12, indicate potential MK61 analogs may have the Cys residue at position 38, 39,or 51 of SEQ ID NOS: 2, 4, 6, 8, 10 and 12 substituted with a Ser or Ala residue; the Cys residue at position 60 or 76 of SEQ ID NOS: 2 and 6 substituted with a Ser or Ala residue; the Cys residue at position 41, 42, 54, 63 or 79 of SEQ ID NOS: 14 and 16 substituted with a Ser or Ala residue; the Leu residue at position 171 or 172 of SEQ ID NOS: 2 substituted with a norluecine, Ile, Val, Met, Ala or Phe; the Leu residue at position 178 or 180 of SEQ ID NOS: 14 and 16 substituted with a norluecine, Ile, Val, Met, Ala or Phe; and the Gly residue at position 141 or SEQ ID NO: 14 or 16 substituted with a Pro or Ala residue.

A number of scientific publications have been devoted to the prediction of secondary structure. See Moult J., *Curr. Op. in Biotech.*, 7(4):422-427 (1996), Chou et al., *Biochemistry*, 13(2):222-245 (1974); Chou et al., *Biochemistry*, 113(2):211-222 (1974); Chou et al., *Adv. Enzymol. Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., *Nucl. Acid. Res.*, 27(1):244-247 (1999). It has been suggested (Brenner et al., *Curr. Op. Struct. Biol.*, 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., *Curr. Opin. Struct. Biol.*, 7(3): 377-87 (1997); Sippl et al., *Structure*, 4(1) :15-19 (1996)), "profile analysis" (Bowie et al., *Science*, 253:164-170 (1991); Gribskov et al., *Meth. Enzym.*, 183:146-159 (1990); Gribskov et al., *Proc. Nat. Acad. Sci.*, 84(13):4355-4358 (1987)), and "evolutionary linkage" (See Holm, supra (1999), and Brenner, supra (1997)).

Preferred MK61 polypeptide variants include glycosylation variants wherein the number and/or type of glycosylation site has been altered compared to the amino acid sequence set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16. In one embodiment, MK61 polypeptide variants comprise a greater or a lesser number of N-linked glycosylation sites than the amino acid sequence set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred MK61 variants include cysteine variants wherein one or more cysteine residues are deleted from or substituted for another amino acid (e.g., serine) as compared to the amino acid sequence set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16. Cysteine variants are useful when MK61 polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

The invention further provides polypeptides that comprise an epitope-bearing portion of a protein as shown in SEQ ID NO:2, SEQ ID NO:4, SEQ ID NO:6, SEQ ID NO:8, SEQ ID NO:10, SEQ ID NO:12, SEQ ID NO:14, or SEQ ID NO:16. The term, "epitope" refers to a region of a protein to which an antibody can bind. See e.g., Geysen et al., *PNAS, USA* 81:3998-4002 (1984). Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., *Science* 219:660-666 (1983). Antibodies that recognize short, linear epitopes are particularly useful in analytic and diagnostic applications that employ denatured protein, such as Western blotting. See Tobin, *Proc. Natl. Acad. Sci. USA*, 76:4350-4356 (1979). Antibodies to short peptides may also recognize proteins in native conformation and will thus be useful for monitoring protein expression and protein isolation, and in detecting MK61 proteins in solution, such as by ELISA or in immunoprecipitation studies.

In addition, the polypeptide comprising the amino acid sequence of SEQ ID NO:2, SEQ ID NO:4, SEQ ID NO:6, SEQ ID NO:8, SEQ ID NO:10, SEQ ID NO:12, SEQ ID NO:14, or SEQ ID NO:16, or an MK61 polypeptide variant may be fused to a homologous polypeptide to form a homodimer or to a heterologous polypeptide to form a heterodimer. Heterologous peptides and polypeptides include, but are not limited to: an epitope to allow for the detection and/or isolation of an MK61 fusion polypeptide; a transmembrane receptor protein or a portion thereof, such as an extracellular domain, or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, or SEQ ID NO:16, or an MK61 polypeptide variant.

Fusions can be made either at the amino terminus or at the carboxy terminus of the polypeptides comprising the amino acid sequence set forth in SEQ ID NO:2, SEQ ID NO:4, SEQ ID NO:6, SEQ ID NO:8, SEQ ID NO:10, SEQ ID NO:12, or SEQ ID NO:14, or an MK61 polypeptide variant. Fusions may be direct with no linker or adapter molecule, or indirect using a linker or adapter molecule. A linker or adapter molecule may be one or more amino acid residues, typically from about 20 to about 50 amino acid residues. A linker or adapter molecule may also be designed with a cleavage site for a DNA restriction endonuclease in an encoding polynucleotide or for a protease to allow for the separation of the fused moieties. It will be appreciated that once constructed, the fusion polypeptides can be derivatized according to the methods described herein.

In a further embodiment of the invention, the polypeptide comprising the amino acid sequence of SEQ ID NO:2, SEQ ID NO:4, SEQ ID NO:6, SEQ ID NO:8, SEQ ID NO:10, SEQ ID NO:12, SEQ ID NO:14, or an MK61 polypeptide variant is fused to one or more domains of an Fc region of human IgG. Antibodies comprise two functionally independent parts, a variable domain known as "Fab", which binds antigens, and a constant domain known as "Fc", which is involved in effector functions such as complement activation and attack by phagocytic cells. An Fc has a long serum half-life, whereas an Fab is short-lived. Capon et al., *Nature*, 337:525-31 (1989). When constructed together with a therapeutic protein, an Fc domain can provide longer half-life or incorporate such functions as Fc receptor binding, protein A binding, complement fixation and perhaps even placental transfer. Id. Table II summarizes the use of certain Fc fusions known in the art.

TABLE II

| Fc Fusion with Therapeutic Proteins | | | |
|---|---|---|---|
| Form of Fc | Fusion partner | Therapeutic implications | Reference |
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al. (1995), J. Immunol., 154: 5590-5600 |

TABLE II-continued

| Fc Fusion with Therapeutic Proteins | | | |
|---|---|---|---|
| Form of Fc | Fusion partner | Therapeutic implications | Reference |
| IgG1 | TNF receptor | septic shock | Fisher et al. (1996), N. Engl. J. Med., 334: 1697-1702; Van Zee et al., (1996), J. Immunol., 156: 2221-2230 |
| IgG, IgA, IgM, or IgE (excluding the first domain) | TNF receptor | inflammation, autoimmune disorders | U.S. Pat. No. 5,808,029, issued Sep. 15, 1998 |
| IgG1 | CD4 receptor | AIDS | Capon et al. (1989), Nature 337: 525-531 |
| IgG1, IgG3 | N-terminus of IL-2 | anti-cancer, antiviral | Harvill et al. (1995), Immunotech., 1: 95-105 |
| IgG1 | C-terminus of OPG | osteoarthritis; bone density | WO 97/23614, published Jul. 3, 1997 |
| IgG1 | N-terminus of leptin | anti-obesity | PCT/US 97/23183, filed Dec. 11, 1997 |
| Human Ig Cγ1 | CTLA-4 | autoimmune disorders | Linsley (1991), J. Exp. Med., 174: 561-569 |

In one example, all or a portion of the human IgG hinge, $CH_2$ and $CH_3$ regions may be fused at either the N-terminus or C-terminus of the MK61 polypeptides using methods known to the skilled artisan. The resulting MK61 fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, reduce aggregation, etc.

Identity and similarity of related nucleic acid molecules and polypeptides can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., *SIAM J. Applied Math.*, 48:1073 (1988).

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., *Nucl. Acid. Res.*, 12:387 (1984); Genetics Computer Group, University of Wisconsin, Madison, Wis., BLASTP, BLASTN, and FASTA (Altschul et al., *J. Mol. Biol.*, 215:403-

410 (1990)). The BLASTX program is publicly available from the National Center for Biotechnology Information (NCBI) and other sources (*BLAST Manual*, Altschul et al. NCB/NLM/NIH Bethesda, Md. 20894; Altschul et al., supra (1990)). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in a preferred embodiment the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually ¹⁄₁₀ times the gap opening penalty), as well as a comparison matrix such as PAM 250 or BLOSUM 62 are used in conjunction with the algorithm. A standard comparison matrix (see Dayhoff et al., *Atlas of Protein Sequence and Structure*, 5(3)(1978) for the PAM 250 comparison matrix; Henikoff et al., *Proc. Natl. Acad. Sci USA*, 89:10915-10919 (1992) for the BLOSUM 62 comparison matrix) is also used by the algorithm.

Preferred parameters for a polypeptide sequence comparison include the following:
  Algorithm: Needleman et al., *J. Mol. Biol.*, 48:443-453 (1970);
  Comparison matrix: BLOSUM 62 from Henikoff et al., supra (1992);
  Gap Penalty: 12
  Gap Length Penalty: 4
  Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparisons include the following:
  Algorithm: Needleman et al., supra (1970);
  Comparison matrix: matches=+10, mismatch=0
  Gap Penalty: 50
  Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used by those of skill in the art, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Synthesis

It will be appreciated by those skilled in the art that the nucleic acid and polypeptide molecules described herein may be produced by recombinant and other means.

Nucleic Acid Molecules

The nucleic acid molecules encode a polypeptide comprising the amino acid sequence of an MK61 polypeptide and can readily be obtained in a variety of ways including, without limitation, chemical synthesis, cDNA or genomic library screening, expression library screening and/or PCR amplification of cDNA.

Recombinant DNA methods used herein are generally those set forth in Sambrook et al., *Molecular Cloning: A Laboratory Manual*, Cold Spring Harbor Laboratory Press, Cold Spring Harbor, N.Y. (1989), and/or Ausubel et al., eds., *Current Protocols in Molecular Biology*, Green Publishers Inc. and Wiley and Sons, NY (1994). The present invention provides for nucleic acid molecules as described herein and methods for obtaining such molecules.

Where a gene encoding the amino acid sequence of an MK61 polypeptide has been identified from one species, all or a portion of that gene may be used as a probe to identify orthologs or related genes from the same species. The probes or primers may be used to screen cDNA libraries from various tissue sources believed to express the MK61 polypeptide. In addition, part or all of a nucleic acid molecule having the sequence as set forth in SEQ ID NO:1, SEQ ID NO:3, SEQ ID NO:5, SEQ ID NO:7, SEQ ID NO:9, SEQ ID NO:11, SEQ ID NO:13, or SEQ ID NO:15 may be used to screen a genomic library to identify and isolate a gene encoding the amino acid sequence of an MK61 polypeptide. Typically, conditions of moderate or high stringency will be employed for screening to minimize the number of false positives obtained from the screening.

Nucleic acid molecules encoding the amino acid sequence of MK61 polypeptides may also be identified by expression cloning which employs the detection of positive clones based upon a property of the expressed protein. Typically, nucleic acid libraries are screened by the binding of an antibody or other binding partner (e.g., receptor or ligand) to cloned proteins which are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence which encodes the amino acid sequence of an MK61 polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of an MK61 polypeptide can be inserted into an expression vector. By introducing the expression vector into an appropriate host, the encoded MK61 polypeptide may be produced in large amounts.

Another method for obtaining a suitable nucleic acid sequence is the polymerase chain reaction (PCR). In this method, cDNA is prepared from poly(A)+ RNA or total RNA using the enzyme reverse transcriptase. Two oligonucleotide primers, typically complementary to two separate regions of cDNA (oligonucleotides) encoding the amino acid sequence of an MK61 polypeptide, are then added to the cDNA along with a polymerase such as Taq polymerase, and the polymerase amplifies the cDNA region between the two primers.

Another means of preparing a nucleic acid molecule encoding the amino acid sequence of an MK61 polypeptide is chemical synthesis using methods well known to the skilled artisan, such as those described by Engels et al., *Angew. Chem. Intl. Ed.*, 28:716-734 (1989). These methods include, inter alia, the phosphotriester, phosphoramidite and H-phosphonate methods for nucleic acid synthesis. A preferred method for such chemical synthesis is polymer-supported synthesis using standard phosphoramidite chemistry. Typically, the DNA encoding the amino acid sequence of an MK61 polypeptide will be several hundred nucleotides in length. Nucleic acids larger than about 100 nucleotides can be synthesized as several fragments using these methods. The fragments can then be ligated together to form the full-length nucleotide sequence of an MK61 polypeptide. Usually, the DNA fragment encoding the amino terminus of the polypeptide will have an ATG, which encodes a methionine residue. This methionine may or may not be present on the mature form of the MK61 polypeptide, depending on whether the polypeptide produced in the host cell is designed to be secreted from that cell. Other methods known to the skilled artisan may be used as well.

In certain embodiments, nucleic acid variants contain codons which have been altered for the optimal expression of an MK61 polypeptide in a given host cell. Particular codon alterations will depend upon the MK61 polypeptide(s) and host cell(s) selected for expression. Such "codon optimization" can be carried out by a variety of methods, for example, by selecting codons which are preferred for use in highly expressed genes in a given host cell. Computer algorithms which incorporate codon frequency tables such as "Ecohigh.cod" for codon preference of highly expressed bacterial genes may be used and are provided by the University of Wisconsin Package Version 9.0, Genetics Computer Group, Madison, Wis. Other useful codon frequency tables include "Celegans_high.cod", "Celegans_low.cod", "*Drosophila_*high.cod", "Human_high.cod", "Maize_high.cod", and "Yeast_high.cod".

Vectors and Host Cells

A nucleic acid molecule encoding the amino acid sequence of an MK61 polypeptide may be inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of an MK61 polypeptide may be amplified/expressed in prokaryotic, yeast, insect (baculovirus systems), and/or eukaryotic host cells. Selection of the host cell will depend in part on whether an MK61 polypeptide is to be post-translationally modified (e.g., glycosylated and/or phosphorylated). If so, yeast, insect, or mammalian host cells are preferable. For a review of expression vectors, see *Meth. Enz.*, vol. 185, D. V. Goeddel, ed., Academic Press Inc., San Diego, Calif. (1990).

Typically, expression vectors used in any of the host cells will contain sequences for plasmid maintenance and for cloning and expression of exogenous nucleotide sequences. Such sequences, collectively referred to as "flanking sequences" in certain embodiments, will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the MK61 polypeptide coding sequence; the oligonucleotide sequence encodes polyHis (such as hexaHis), or another "tag" such as FLAG, HA (hemaglutinin influenza virus) or myc for which commercially available antibodies exist. This tag is typically fused to the polypeptide upon expression of the polypeptide, and can serve as a means for affinity purification of the MK61 polypeptide from the host cell. Affinity purification can be accomplished, for example, by column chromatography using antibodies against the tag as an affinity matrix. Optionally, the tag can subsequently be removed from the purified MK61 polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source) or synthetic, or the flanking sequences may be native sequences which normally function to regulate MK61 polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

The flanking sequences useful in the vectors of this invention may be obtained by any of several methods well known in the art. Typically, flanking sequences useful herein other than the endogenous MK61 gene flanking sequences will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with suitable oligonucleotide and/or flanking sequence fragments from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of an MK61 polypeptide. If the vector of choice does not contain an origin of replication site, one may be chemically synthesized based on a known sequence, and ligated into the vector. For example, the origin of replication from the plasmid pBR322 (Product No. 303-3s, New England Biolabs, Beverly, Mass.) is suitable for most gram-negative bacteria, and various origins (e.g., SV40, polyoma, adenovirus, vesicular stomatitus virus (VSV) or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G–C rich fragment followed by a poly T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene which will be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure which only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes an MK61 polypeptide. As a result, increased quantities of MK61 polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of an MK61 polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct an MK61 polypeptide out of the host cell. Typically, a nucleotide sequence encoding the signal sequence is positioned in the coding region of an MK61 nucleic acid molecule, or directly at the 5' end of an MK61 polypeptide coding region. Many signal sequences have been identified, and any of those that are functional in the selected host cell may be used in conjunction with an MK61 nucleic acid molecule. Therefore, a signal sequence may be homologous (naturally occurring) or heterologous to an MK61 gene or cDNA. Additionally, a signal sequence may be chemically synthesized using methods described herein. In most cases, the secretion of an MK61 polypeptide from the host cell via the presence of a signal peptide will result in the removal of the signal peptide from the secreted MK61 polypeptide. The signal sequence may be a component of the vector, or it may be a part of an MK61 nucleic acid molecule that is inserted into the vector.

Included within the scope of this invention is the use of either a nucleotide sequence encoding a native MK61 polypeptide signal sequence joined to an MK61 polypeptide coding region or a nucleotide sequence encoding a heterologous signal sequence joined to an MK61 polypeptide coding region. The heterologous signal sequence selected should be one that is recognized and processed, i.e., cleaved by a signal peptidase, by the host cell. For prokaryotic host cells that do not recognize and process the native MK61 polypeptide signal sequence, the signal sequence is substituted by a prokaryotic signal sequence selected, for example, from the group of the alkaline phosphatase, penicillinase, or heat-stable enterotoxin II leaders. For yeast secretion, the native MK61 polypeptide signal sequence may be substituted by the yeast invertase, alpha factor, or acid phosphatase leaders. In mammalian cell expression the native signal sequence is satisfactory, although other mammalian signal sequences may be used.

In some cases, such as where glycosylation is desired in a eukaryotic host cell expression system, one may manipulate the various presequences to improve glycosylation or yield. For example, one may alter the peptidase cleavage site of a particular signal peptide, or add presequences, which also may affect glycosylation. The final protein product may have, in the −1 position (relative to the first amino acid of the mature protein), one or more additional amino acids incident to expression which may not have been totally removed. For example, the final protein product may have one or two amino acid residues found in the peptidase cleavage site, attached to the N-terminus. Alternatively, use of some enzyme cleavage sites may result in a slightly truncated form of the desired MK61 polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the MK61 gene, especially where the gene used is a full length genomic sequence or a fragment thereof. Where the intron is not naturally occurring within the gene (as for most cDNAs), the intron(s) may be obtained from another source. The position of the intron with respect to flanking sequences and the MK61 gene is generally important, as the intron must be transcribed to be effective. Thus, when an MK61 cDNA molecule is being transcribed, the preferred position for the intron is 3' to the transcription start site, and 5' to the polyA transcription termination sequence. Preferably, the intron or introns will be located on one side or the other (i.e., 5' or 3') of the cDNA such that it does not interrupt the coding sequence. Any intron from any source, including viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

The expression and cloning vectors of the present invention will each typically contain a promoter that is recognized by the host organism and operably linked to the molecule encoding an MK61 polypeptide. Promoters are untranscribed sequences typically located upstream (5') to the start codon of a structural gene (generally within about 100 to 1000 bp) that control the transcription of the structural gene. Promoters are conventionally grouped into one of two classes, inducible promoters and constitutive promoters. In this context, inducible promoters include repressible/depressible promoters and conventional inducible promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding an MK61 polypeptide by, e.g., removing the promoter from the source DNA by restriction enzyme digestion and inserting the desired promoter sequence into the vector. The native MK61 gene promoter sequence may be used to direct amplification and/or expression of an MK61 nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their sequences have been published, thereby enabling one skilled in the art to ligate them to the desired DNA sequence(s), using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowl pox virus, adenovirus (such as Adenovirus 2), bovine papilloma virus, avian sarcoma virus, cytomegalovirus (CMV), a retrovirus, hepatitis-B virus and most preferably Simian Virus 40 (SV40). Other suitable mammalian promoters include heterologous mammalian promoters, e.g., heat-shock promoters and the actin promoter.

Additional promoters which may be of interest in controlling MK61 gene transcription include, but are not limited to: the SV40 early promoter region (Bernoist and Chambon, *Nature,* 290:304-310, (1981)), the CMV promoter, the promoter contained in the 3' long terminal repeat of Rous sarcoma virus (Yamamoto et al., *Cell,* 22:787-797, (1980)); the herpes thymidine kinase promoter (Wagner et al., *Proc. Natl. Acad. Sci. USA,* 78:144-145, (1981)), the regulatory sequences of the metallothionine gene (Brinster et al., *Nature,* 296:39-42, (1982)), prokaryotic expression vectors such as the beta-lactamase promoter (Villa-Kamaroff, et al., *Proc. Natl. Acad. Sci. USA,* 75:3727-3731, (1978)), or the tac promoter (DeBoer, et al., *Proc. Natl. Acad. Sci. USA,* 80:21-25, (1983)). Also of interest are the following animal transcriptional control regions, which exhibit tissue specificity and have been utilized in transgenic animals: the elastase I gene control region which is active in pancreatic acinar cells [Swift et al., *Cell,* 38:639-646, (1984); Ornitz et al., *Cold Spring Harbor Symp. Quant. Biol.,* 50:399-409 (1986); MacDonald, *Hepatology,* 7:425-515, (1987)]; the insulin gene control region which is active in pancreatic beta cells (Hanahan, *Nature,* 315:115-122, (1985)); the immunoglobulin gene control region which is active in lymphoid cells (Grosschedl et al., *Cell,* 38:647-658 (1984)); Adames et al., *Nature,* 318: 533-538 (1985)); (Alexander et al., *Mol. Cell. Biol.,* 7:1436-1444, (1987)); the mouse mammary tumor virus control region which is active in testicular, breast, lymphoid and mast cells (Leder et al., *Cell,* 45:485-495, (1986) ); the albumin gene control region which is active in liver (Pinkert et al., *Genes and Devel.,* 1:268-276, (1987)); the alphafetoprotein gene control region which is active in liver (Krumlauf et al., *Mol. Cell. Biol.,* 5:1639-1648, (1985)); Hammer et al., *Science,* 235:53-58, (1987)); the alpha 1-antitrypsin gene control region which is active in the liver (Kelsey et al., *Genes and Devel.,* 1:161-171, (1987)); the beta-globin gene control region which is active in myeloid cells [Mogram et al., *Nature,* 315:338-340, (1985); Kollias et al., *Cell,* 46:89-94, (1986)]; the myelin basic protein gene control region which is active in oligodendrocyte cells in the brain (Readhead et al., *Cell,* 48:703-712, (1987)); the myosin light chain-2 gene control region which is active in skeletal muscle (Sani, *Nature,* 314:283-286, (1985)); and the gonadotropic releasing hormone gene control region which is active in the hypothalamus (Mason et al., *Science,* 234:1372-1378, (1986)).

An enhancer sequence may be inserted into the vector to increase the transcription of a DNA encoding an MK61 polypeptide of the present invention by higher eukaryotes. Enhancers are cis-acting elements of DNA, usually about 10-300 bp in length, that act on the promoter to increase its transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to an MK61 nucleic acid molecule, it is typically located at a site 5' from the promoter.

Expression vectors of the invention may be constructed from a starting vector such as a commercially available vector. Such vectors may or may not contain all of the desired flanking sequences. Where one or more of the desired flanking sequences are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen Company, Carlsbad, Calif.), pBSII (Stratagene Company, La Jolla, Calif.), pET15β (Novagen, Madison, Wis.), pGEX (Pharmacia Biotech, Piscataway, N.J.), pEGFP-N2 (Clontech, Palo Alto, Calif.), PETL (Blue-BacII; Invitrogen), pDSR-alpha (PCT Publication No. WO 90/14363) and pFastBacDual (Gibco/BRL, Grand Island, N.Y.

Additional suitable vectors include, but are not limited to, cosmids, plasmids or modified viruses, but it will be appreciated that the vector system must be compatible with the selected host cell. Such vectors include, but are not limited to, plasmids such as Bluescript® plasmid derivatives (a high copy number ColE1-based phagemid, Stratagene Cloning Systems Inc., La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast, or virus vectors such as a baculovirus expression system (pBacPAK plasmid derivatives, Clontech, Palo Alto, Calif.).

After the vector has been constructed and a nucleic acid molecule encoding an MK61 polypeptide has been inserted into the proper site of the vector, the completed vector may be inserted into a suitable host cell for amplification and/or polypeptide expression. The transformation of an expression vector for an MK61 polypeptide into a selected host cell may be accomplished by well-known methods such as transfection, infection, calcium chloride-mediated transformation, electroporation, microinjection, lipofection or the DEAE-dextran method or other known techniques. The method selected will in part be a function of the type of host cell to be used. These methods and other suitable methods are well known to the skilled artisan and are set forth, for example, in Sambrook et al., supra.

Host cells may be prokaryotic host cells (such as *E. coli*) or eukaryotic host cells (such as yeast, an insect or vertebrate cells). The host cell, when cultured under appropriate conditions, may synthesizes an MK61 polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation), and ease of folding into a biologically active molecule.

A number of suitable host cells are known in the art and many are available from the American Type Culture Collection (ATCC), 10801 University Boulevard, Manassas, Va. 20110-2209. Examples include, but are not limited to, mammalian cells, such as Chinese hamster ovary cells (CHO) (ATCC No. CCL61); CHO DHFR-cells (Urlaub et al., *Proc. Natl. Acad. Sci. USA*, 97:4216-4220 (1980)); human embryonic kidney (HEK) 293 or 293T cells (ATCC No. CRL1573); or 3T3 cells (ATCC No. CCL92). The selection of suitable mammalian host cells and methods for transformation, culture, amplification, screening, product production and purification are known in the art. Other suitable mammalian cell lines are the monkey COS-1 (ATCC No. CRL1650) and COS-7 (ATCC No. CRL1651) cell lines, and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominant acting selection gene. Other suitable mammalian cell lines include, but are not limited to, mouse neuroblastoma N2A cells, HeLa, mouse L-929 cells, 3T3 lines derived from Swiss, Balb-c or NIH mice, BHK or HaK hamster cell lines, which are also available from the ATCC. Each of these cell lines is known by and available to those skilled in the art of protein expression.

Similarly useful as host cells suitable for the present invention are bacterial cells. For example, the various strains of *E. coli* (e.g., HB101, (ATCC No. 33694) DH5α, DH10 and MC1061 (ATCC No. 53338)) are well known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for expression of the polypeptides of the present invention. Preferred yeast cells include, for example, *Saccharomyces cerivisae* and *Pichia pastoris*.

Additionally, where desired, insect cell systems may be utilized in the methods of the present invention. Such systems are described for example in Kitts et al., *Biotechniques*, 14:810-817 (1993); Lucklow, *Curr. Opin. Biotechnol.*, 4:564-572 (1993); and Lucklow et al., *J. Virol.*, 67:4566-4579 (1993). Preferred insect cells are Sf-9 and Hi5 (Invitrogen, Carlsbad, Calif.).

One may also use transgenic animals to express glycosylated MK61 polypeptides. For example, one may use a transgenic milk-producing animal (a cow or goat, for example) and obtain the present glycosylated polypeptide in the animal milk. One may also use plants to produce MK61 polypeptides; however, in general, the glycosylation occurring in plants is different from that produced in mammalian cells, and may result in a glycosylated product which is not suitable for human therapeutic use.

Polypeptide Production

Host cells comprising an MK61 polypeptide expression vector may be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as indicated by the particular cell line being cultured. A suitable medium for insect cultures is Grace's medium supplemented with yeastolate, lactalbumin hydrolysate and/or fetal calf serum, as necessary.

Typically, an antibiotic or other compound useful for selective growth of transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline and neomycin.

The amount of an MK61 polypeptide produced by a host cell can be evaluated using standard methods known in the art. Such methods include, without limitation, Western blot analysis, SDS-polyacrylamide gel electrophoresis, non-denaturing gel electrophoresis, chromatographic separation such as Hgh Performance Liquid Chromatography (HPLC), immunodetection such as immunoprecipitation, and/or activity assays such as DNA binding gel shift assays.

If an MK61 polypeptide has been designed to be secreted from the host cells, the majority of polypeptide may be found in the cell culture medium. If however, the MK61 polypeptide is not secreted from the host cells, it will be present in the cytoplasm and/or the nucleus (for eukaryotic host cells) or in the cytosol (for bacterial host cells).

For an MK61 polypeptide situated in the host cell cytoplasm and/or the nucleus (for eukaryotic host cells) or in the cytosol (for bacterial host cells), intracellular material (including inclusion bodies for gram-negative bacteria) can be extracted from the host cell using any standard technique known to the skilled artisan. For example, the host cells can be lysed to release the contents of the periplasm/cytoplasm by osmotic shock French press, homogenization, enzymatic disruption, exposure to detergents or chaotropes, and/or sonication followed by centrifugation.

If an MK61 polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The MK61 polypeptide in its now soluble form can then be analyzed using gel electrophoresis, immunoprecipitation or the like. If it is desired to isolate the MK61 polypeptide, isolation may be accomplished using standard methods such as those described herein and in Marston et al., *Meth. Enz.*, 182:264-275 (1990).

In some cases, an MK61 polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cuprous chloride, dithiothreitol(DTT)/dithiane DTT, and 2-2mercaptoethanol(bME)/dithio-b(ME). A cosolvent may be used to increase the efficiency of the refolding, and the more common reagents used for this purpose include glycerol, polyethylene glycol of various molecular weights, arginine and the like.

If inclusion bodies are not formed to a significant degree upon expression of an MK61 polypeptide, then the polypeptide will be found primarily in the supernatant after centrifugation of the cell homogenate. The polypeptide may be further isolated from the supernatant using methods such as those described herein or otherwise known in the art.

The purification of an MK61 polypeptide from solution can be accomplished using a variety of techniques. If the polypeptide has been synthesized such that it contains a tag such as Hexahistidine (MK61 polypeptide/hexaHis) or other small peptide such as FLAG (Eastman Kodak Co., New Haven, Conn.) or myc (Invitrogen, Carlsbad, Calif.) at either its carboxyl or amino terminus, it may be purified in a one-step process by passing the solution through an affinity column where the column matrix has a high affinity for the tag.

For example, polyhistidine binds with great affinity and specificity to nickel; thus an affinity column of nickel (such as the Qiagen® nickel columns) can be used for purification of MK61 polypeptide/polyHis. See for example, Ausubel et al., eds., *Current Protocols in Molecular Biology*, Section 10.11.8, John Wiley & Sons, New York (1993).

Additionally, the MK61 polypeptide may be purified through use of a monoclonal antibody which is capable of specifically recognizing and binding to the MK61 polypeptide.

Suitable procedures for purification thus include, without limitation, affinity chromatography, immunoaffinity chromatography, ion exchange chromatography, molecular sieve chromatography, High Performance Liquid Chromatography (HPLC), electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

MK61 polypeptides may also be prepared by chemical synthesis methods (such as solid phase peptide synthesis) using techniques known in the art, such as those set forth by Merrifield et al., *J. Am. Chem. Soc.*, 85:2149 (1963), Houghten et al., *Proc. Natl. Acad. Sci. USA*, 82:5132 (1985), and Stewart and Young, "Solid Phase Peptide Synthesis", Pierce Chemical Co., Rockford, Ill. (1984). Such polypeptides may be synthesized with or without a methionine on the amino terminus. Chemically synthesized MK61 polypeptides may be oxidized using methods set forth in these references to form disulfide bridges. Chemically synthesized MK61 polypeptides are expected to have comparable biological activity to the corresponding MK61 polypeptides produced recombinantly or purified from natural sources, and thus may be used interchangeably with a recombinant or natural MK61 polypeptide.

Another means of obtaining an MK61 polypeptide is via purification from biological samples such as source tissues and/or fluids in which the MK61 polypeptide is naturally found. Such purification can be conducted using methods for protein purification as described herein or as otherwise known in the art. The presence of the MK61 polypeptide during purification may be monitored, for example, using an antibody prepared against recombinantly produced MK61 polypeptide or peptide fragments thereof.

A number of additional methods for producing nucleic acids and polypeptides are known in the art, and the methods can be used to produce polypeptides having specificity for MK61. See for example, Roberts et al., *Proc. Natl. Acad. Sci. USA*, 94:12297-12303 (1997), which describes the production of fusion proteins between an mRNA and its encoded peptide. See also Roberts, R., *Curr. Opin. Chem. Biol.*, 3:268-273 (1999). Additionally, U.S. Pat. No. 5,824,469 describes methods of obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those which exhibit a predetermined biological function. From that subpopulation, oligonucleotides capable of carrying out the desired biological function are isolated.

U.S. Pat. Nos. 5,763,192, 5,814,476, 5,723,323 and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter randomly locates a break at the front 5' end of a gene, initiating transcription of the gene. This results in expression of the desired peptide or polypeptide.

It will be appreciated that these methods can also be used to create comprehensive IL-17 like protein expression libraries, which can subsequently be used for high throughput phenotypic screening in a variety of assays, such as biochemical assays, cellular assays, and whole organism assays (e.g., plant, mouse, etc.).

Chemical Derivatives

Chemically modified derivatives of the MK61 polypeptides may be prepared by one skilled in the art, given the disclosures set forth hereinbelow. MK61 polypeptide derivatives are modified in a manner that is different either in the type or location of the molecules naturally attached to the polypeptide. Derivatives may include molecules formed by the deletion of one or more naturally-attached chemical groups. The polypeptide comprising the amino acid sequence of SEQ ID NO:2, SEQ ID NO:4, SEQ ID NO:6, SEQ ID NO:8, SEQ ID NO:10, SEQ ID NO:12, SEQ ID NO:14, or SEQ ID NO:16, or an MK61 polypeptide variant, may be modified by the covalent attachment of one or more polymers. For example, the polymer selected is typically water soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water soluble polymer, some molecules will weigh more, some less, than the stated molecular weight). The average molecular weight of each polymer is preferably between about 5 kDa, about 50 kDa, more preferably between about 12 kDa to about 40 kDa and most preferably between about 20 kDa to about 35 kDa.

Suitable water soluble polymers or mixtures thereof include, but are not limited to, N-linked or O-linked carbohydrates; sugars; phosphates; polyethylene glycol (PEG) (including the forms of PEG that have been used to derivatize proteins, including mono-($C_1$-$C_{10}$) alkoxy- or aryloxy-polyethylene glycol); monomethoxy-polyethylene glycol; dextran (such as low molecular weight dextran of, for example, about 6 kDa);, cellulose; or other carbohydrate-based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. Also encompassed by the present invention are bifunctional crosslinking molecules which may be used to prepare covalently attached multimers of the polypeptide comprising the amino acid sequence of SEQ ID NO:2, SEQ ID NO:4, SEQ ID NO:6, SEQ ID NO:8, SEQ ID NO:10, SEQ ID NO:12, SEQ ID NO:14, or SEQ ID NO:16, or an MK61 polypeptide variant.

In general, chemical derivatization may be performed under any suitable condition used to react a protein with an activated polymer molecule. Methods for preparing chemical derivatives of polypeptides will generally comprise the steps of (a) reacting the polypeptide with the activated polymer molecule (such as a reactive ester or aldehyde derivative of the polymer molecule) under conditions whereby the polypeptide comprising the amino acid sequence of SEQ ID NO:2, SEQ ID NO:4, SEQ ID NO:6, SEQ ID NO:8, SEQ ID NO:10, SEQ ID NO:12, SEQ ID NO:14, or SEQ ID NO:16, or an MK61 polypeptide variant becomes attached to one or more polymer molecules, and (b) obtaining the reaction product(s). The optimal reaction conditions will be determined based on known parameters and the desired result. For example, the larger the ratio of polymer molecules:protein, the greater the percentage of attached polymer molecule. In one embodiment, the MK61 polypeptide derivative may have a single polymer molecule moiety at the amino terminus (see, for example, U.S. Pat. No. 5,234,784).

The pegylation of the polypeptide may be specifically carried out by any of the pegylation reactions known in the art, as described for example in the following references: Francis et al., *Focus on Growth Factors*, 3:4-10 (1992); EP 0154316; EP 0401384 and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, the polymer(s) selected should have a single reactive ester group. For reductive alkylation, the polymer(s) selected should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714).

In another embodiment, MK61 polypeptides may be chemically coupled to biotin, and the biotin/MK61 polypeptide molecules which are conjugated are then allowed to bind to avidin, resulting in tetravalent avidin/biotin/MK61 polypeptide molecules. MK61 polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions which may be alleviated or modulated by the administration of the present MK61 polypeptide derivatives include those described herein for MK61 polypeptides. However, the MK61 polypeptide derivatives disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, rabbits, or other rodents, rabbits, goats or sheep, or other farm animals, in which the gene (or genes) encoding the native MK61 polypeptide has (have) been disrupted ("knocked out") such that the level of expression of this gene or genes is significantly decreased or completely abolished. Such animals may be prepared using techniques and methods such as those described in U.S. Pat. No. 5,557,032.

The present invention further includes non-human animals such as mice, rats or other rodents, rabbits, goats, sheep, or other farm animals, in which either the native form of the MK61 gene(s) for that animal or a heterologous MK61 gene(s) is (are) over-expressed by the animal, thereby creating a "transgenic" animal. Such transgenic animals may be prepared using well-known methods such as those described in U.S. Pat. No. 5,489,743 and PCT Application No. WO94/28122.

The present invention further includes non-human animals in which the promoter for one or more of the MK61 polypeptides of the present invention is either activated or inactivated (e.g., by using homologous recombination methods) to alter the level of expression of one or more of the native MK61 polypeptides.

These non-human animals may be used for drug candidate screening. In such screening, the impact of a drug candidate on the animal may be measured; for example, drug candidates may decrease or increase the expression of the MK61 gene. In certain embodiments, the amount of MK61 polypeptide that is produced may be measured after the exposure of the animal to the drug candidate. Additionally, in certain embodiments, one may detect the actual impact of the drug candidate on the animal. For example, the overexpression of a particular gene may result in, or be associated with, a disease or pathological condition. In such cases, one may test a drug candidate's ability to decrease expression of the gene or its ability to prevent, inhibit, or eliminate a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent inhibit, or eliminate a pathological condition.

Microarray

It will be appreciated that DNA microarray technology can be utilized in accordance with the present invention. DNA microarrays are miniature, high density arrays of nucleic acids positioned on a solid support, such as glass. Each cell or element within the array has numerous copies of a single species of DNA which acts as a target for hybridization for its cognate mRNA. In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA which is specifically bound to each target DNA. In this way, the expression of thousands of genes can be quantitated in a high throughput, parallel manner from a single sample of biological material.

This high throughput expression profiling has a broad range of applications with respect to the MK61 molecules of the invention, including but not limited to: the identification and validation of MK61 disease-related genes as targets for therapeutics; molecular toxicology of MK61 molecules and inhibitors thereof; stratification of populations and generation of surrogate markers for clinical trials; and the enhancement of an MK61 related small molecule drug discovery by aiding in the identification of selective compounds in high throughput screens (HTS).

Selective Binding Agents

As used herein, the term "selective binding agent" refers to a molecule which has specificity for one or more MK61 polypeptides. Suitable selective binding agents include, but are not limited to, antibodies and derivatives thereof, polypeptides, and small molecules. Suitable selective binding agents may be prepared using methods known in the art. An exemplary MK61 polypeptide selective binding agent of the present invention is capable of binding a certain portion of the MK61 polypeptide thereby inhibiting the binding of the polypeptide to the MK61 polypeptide receptor(s).

Selective binding agents such as antibodies and antibody fragments that bind MK61 polypeptides are within the scope of the present invention. The antibodies may be polyclonal including monospecific polyclonal, monoclonal (MAbs), recombinant, chimeric, humanized such as CDR-grafted, human, single chain, and/or bispecific, as well as fragments, variants or derivatives thereof. Antibody fragments include those portions of the antibody which bind to an epitope on the MK61 polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward an MK61 polypeptide generally are produced in animals (e.g., rabbits or mice) by means of multiple subcutaneous, intramuscular or intraperitoneal injections of MK61 polypeptide and an adjuvant. It may be useful to conjugate an MK61 polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-MK61 polypeptide antibody titer.

Monoclonal antibodies directed toward an MK61 polypeptide are produced using any method which provides for the production of antibody molecules by continuous cell lines in culture. Examples of suitable methods for preparing monoclonal antibodies include the hybridoma methods of Kohler et al., *Nature*, 256:495-497 (1975) and the human B-cell hybridoma method, Kozbor, *J. Immunol.*, 133:3001 (1984) and Brodeur et al., Monoclonal Antibody Production Techniques and Applications, pp. 51-63 (Marcel Dekker, Inc., New York, 1987). Also provided by the invention are hybridoma cell lines which produce monoclonal antibodies reactive with MK61 polypeptides.

Monoclonal antibodies of the invention may be modified for use as therapeutics. One embodiment is a "chimeric" antibody in which a portion of the heavy and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See, U.S. Pat. No. 4,816,567 and Morrison et al., *Proc. Natl. Acad. Sci. USA*, 81:6851-6855 (1985).

In another embodiment, a monoclonal antibody of the invention is a "humanized" antibody. Methods for humanizing non-human antibodies are well known in the art (see U.S. Pat. Nos. 5,585,089, and 5,693,762). Generally, a humanized antibody has one or more amino acid residues introduced into it from a source which is non-human. Humanization can be performed, for example, using methods described in the art (Jones et al., *Nature* 321:522-525 (1986); Riechmann et al., *Nature*, 332:323-327 (1988); Verhoeyen et al., *Science* 239: 1534-1536 (1988)), by substituting at least a portion of a rodent complementarity-determining region (CDR) for the corresponding regions of a human antibody.

Also encompassed by the invention are human antibodies which bind MK61 polypeptides, fragments, variants, and/or derivatives. Using transgenic animals (e.g., mice) that are capable of producing a repertoire of human antibodies in the absence of endogenous immunoglobulin production, such antibodies are produced by immunization with an MK61 antigen (i.e., having at least 6 contiguous amino acids), optionally conjugated to a carrier. See, for example, Jakobovits et al., *Proc. Natl. Acad. Sci. USA*, 90:2551-2555 (1993); Jakobovits et al., *Nature*, 362:255-258 (1993) and Bruggermann et al., *Year in Immunol.*, 7:33 (1993). In one method, such transgenic animals are produced by incapacitating the endogenous loci encoding the heavy and light immunoglobulin chains therein, and inserting nucleic acids encoding human heavy and light chain proteins into the genome thereof. Partially modified animals, that is those having less than the full complement of modifications, are then cross-bred to obtain an animal having all of the desired immune system modifications. When administered an immunogen, these transgenic animals produce antibodies with human variable regions, including human(rather than, e.g., murine) amino acid sequences, including variable regions which are immunospecific for these antigens. See PCT application nos. PCT/US96/05928 and PCT/US93/06926. Additional methods are described in U.S. Pat. No. 5,545,807, PCT application nos. PCT/US91/245, PCT/GB89/01207, and in EP 546073B1 and EP 546073A1. Human antibodies may also be produced by the expression of recombinant DNA in host cells or by expression in hybridoma cells as described herein.

In an alternative embodiment, human antibodies can be produced from phage-display libraries (Hoogenboom et al., *J. Mol. Biol.* 227:381 (1991) and Marks et al., *J. Mol. Biol.* 222:581 (1991)). These processes mimic immune identification through the display of antibody repertoires on the surface of filamentous bacteriophage, and subsequent selection of phage by their binding to an antigen of choice. One such technique is described in PCT Application No. PCT/US98/17364, filed in the amen of Adams et al. which describes the isolation of high affinity and functionally agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein or known in the art. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-MK61 antibodies of the invention may be employed in any known assay method, such as competitive binding assays, direct and indirect sandwich assays, and immunoprecipitation assays (Sola, Monoclonal Antibodies: A Manual of Techniques, pp. 147-158 (CRC Press, Inc., 1987)) for the detection and quantitation of MK61 polypeptides. The antibodies will bind MK61 polypeptides with an affinity which is appropriate for the assay method being employed.

For diagnostic applications, in certain embodiments, anti-MK61 antibodies may be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$; a fluorescent or chemiluminescent compound, such as fluorescein isothiocyanate, rhodamine, or luciferin; or an enzyme, such as alkaline phosphatase, β-galactosidase, or horseradish peroxidase (Bayer et al., *Meth. Enz.*, 184:138-163 (1990)).

Competitive binding assays rely on the ability of a labeled standard (e.g., an MK61 polypeptide, or an immunologically reactive portion thereof) to compete with the test sample analyte (an MK61 polypeptide) for binding with a limited amount of anti-MK61 antibody. The amount of an MK61 polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-MK61 antibodies, are also useful for in vivo imaging. An antibody labeled with a detectable moiety may be administered to an animal, preferably into the bloodstream, and the presence and location of the labeled antibody in the host is assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists in that they either enhance or reduce, respectively, at least one of the biological activities of an MK61 polypeptide. In one embodiment, antagonist antibodies of the invention are antibodies or binding fragments thereof which are capable of specifically binding to an MK61 polypeptide and which are capable of inhibiting or eliminating the functional activity of an MK61 polypeptide in vivo or in vitro. In preferred embodiments, the selective binding agent, e.g., an antagonist antibody, will inhibit the functional activity of an MK61 polypeptide by at least about 50%, and preferably by at least about 80%. In another embodiment, the selective binding agent may be an antibody that is capable of interacting with an MK61 binding partner (a ligand or receptor) thereby inhibiting or eliminating MK61 activity in vitro or in viva. Selective binding agents, including agonist and antagonist anti-MK61 antibodies, are identified by screening assays which are well known in the art.

The invention also relates to a kit comprising MK61 selective binding agents (such as antibodies) and other reagents useful for detecting MK61 polypeptide levels in biological samples. Such reagents may include a detectable label, blocking serum, positive and negative control samples, and detection reagents.

MK61 polypeptides can be used to clone MK61 ligand(s) using an "expression cloning" strategy. Radiolabeled ($^{125}$Iodine) MK61 polypeptide or "affinity/activity-tagged" MK61 polypeptide (such as an Fc fusion or an alkaline phosphatase fusion) can be used in binding assays to identify a cell type or a cell line or tissue that expresses MK61 ligand(s). RNA isolated from such cells or tissues can then be converted to cDNA, cloned into a mammalian expression vector, and transfected into mammalian cells (for example, COS, or 293) to create an expression library. Radiolabeled or tagged MK61 polypeptide can then be used as an affinity reagent to identify and isolate the subset of cells in this library expressing MK61 ligand(s). DNA is then isolated from these cells and transfected into mammalian cells to create a secondary expression library in which the fraction of cells expressing MK61 ligand(s) would be many-fold higher than in the original library. This enrichment process can be repeated iteratively until a single recombinant clone containing an MK61 ligand is isolated. Isolation of MK61 ligand(s) is useful for identifying or developing novel agonists and antagonists of the MK61 signaling pathway. Such agonists and antagonists include MK61 ligand(s), anti-MK61 ligand antibodies, small molecules or antisense oligonucleotides. These may be used for treating, preventing, or diagnosing one or more diseases or disorders, including those described herein.

Assaying For Other Modulators of MK61 Polypeptide Activity

In some situations, it may be desirable to identify molecules that are modulators, i.e., agonists or antagonists, of the activity of MK61 polypeptide. Natural or synthetic molecules that modulate MK61 like polypeptide may be identified using one or more screening assays, such as those described herein. Such molecules may be administered either in an ex vivo manner, or in an in vivo manner by injection, or by oral delivery, implantation device or the like.

"Test molecule(s)" refers to the molecule(s) that is/are under evaluation for the ability to modulate (i.e., increase or decrease) the activity of an MK61 polypeptide. Most commonly, a test molecule will interact directly with an MK61 polypeptide. However, it is also contemplated that a test molecule may also modulate MK61 polypeptide activity indirectly, such as by affecting MK61 gene expression, or by binding to an MK61 binding partner (e.g., receptor or ligand). In one embodiment, a test molecule will bind to an MK61 polypeptide with an affinity constant of at least about $10^{-6}$ M, preferably about $10^{-8}$ M, more preferably about $10^{-9}$ M, and even more preferably about $10^{-10}$ M.

Methods for identifying compounds which interact with MK61 polypeptides are encompassed by the present invention. In certain embodiments, an MK61 polypeptide is incubated with a test molecule under conditions which permit the interaction of the test molecule with an MK61 polypeptide, and the extent of the interaction can be measured. The test molecule(s) can be screened in a substantially purified form or in a crude mixture.

In certain embodiments, an MK61 polypeptide agonist or antagonist may be a protein, peptide, carbohydrate, lipid, or small molecular weight molecule which interacts with MK61 polypeptide to regulate its activity. Molecules which regulate MK61 polypeptide expression include nucleic acids which are complementary to nucleic acids encoding an MK61 polypeptide, or are complementary to nucleic acid sequences which direct or control the expression of MK61 polypeptide, and which act as anti-sense regulators of expression.

Once a set of test molecules has been identified as interacting with an MK61 polypeptide, the molecules may be further evaluated for their ability to increase or decrease MK61 polypeptide activity. The measurement of the interaction of test molecules with MK61 polypeptides may be carried out in several formats, including cell-based binding assays, membrane binding assays, solution-phase assays and immunoassays. In general, test molecules are incubated with an MK61 polypeptide for a specified period of time, and MK61 polypeptide activity is determined by one or more assays for measuring biological activity.

The interaction of test molecules with MK61 polypeptides may also be assayed directly using polyclonal or monoclonal antibodies in an immunoassay. Alternatively, modified forms of MK61 polypeptides containing epitope tags as described herein may be used in immunoassays.

In the event that MK61 polypeptides display biological activity through an interaction with a binding partner (e.g., a receptor or a ligand) are assessed by a variety of in vitro assays may be used to measure the binding of an MK61 polypeptide to the corresponding binding partner (such as a selective binding agent, receptor or ligand). These assays are used to screen test molecules for their ability to increase or decrease the rate and/or the extent of binding of an MK61 polypeptide to its binding partner. In one assay, an MK61 polypeptide is immobilized in the wells of a microtiter plate. Radiolabeled MK61 binding partner (for example, iodinated MK61 binding partner) and the test molecule(s) are added either one at a time (in either order) or simultaneously to the wells. After incubation, the wells are washed and counted (using a scintillation counter) for radioactivity to determine the extent to which the binding partner bound to MK61 polypeptide. Typically, the molecules will be tested over a range of concentrations, and a series of control wells lacking one or more elements of the test assays can be used for accuracy in the evaluation of the results. An alternative to this method involves reversing the "positions" of the proteins, i.e., immobilizing MK61 binding partner to the microtiter plate wells, incubating with the test molecule and radiolabeled MK61 polypeptide, and determining the extent of MK61 polypeptide binding. See, for example, chapter 18, *Current Protocols in Molecular Biology*, Ausubel et al., eds., John Wiley & Sons, New York, N.Y. (1995).

As an alternative to radiolabeling, an MK61 polypeptide or its binding partner may be conjugated to biotin and the presence of biotinylated protein can then be detected using streptavidin linked to an enzyme, such as horseradish peroxidase (HRP) or alkaline phosphatase (AP), is detected colorometrically or by fluorescent tagging of streptavidin. An antibody directed to an MK61 polypeptide or to an MK61 binding partner and conjugated to biotin may also be used and can be detected after incubation with enzyme-linked streptavidin linked to AP or HRP.

An MK61 polypeptide or an MK61 binding partner can also be immobilized by attachment to agarose beads, acrylic beads or other types of such inert solid phase substrates. The substrate-protein complex can be placed in a solution containing the complementary protein and the test compound. After incubation the beads is precipitated by centrifugation, and the amount of binding between an MK61 polypeptide and its binding partner can be assessed using the methods described herein. Alternatively, the substrate-protein complex is immobilized in a column, and the test molecule and complementary protein are passed through the column. The formation of a complex between an MK61 polypeptide and its binding partner is assessed using any of the techniques set forth herein, i.e., radiolabeling, antibody binding or the like.

Another in vitro assay that is useful for identifying a test molecule that increases or decreases the formation of a complex between an MK61 polypeptide and an MK61 binding partner is a surface plasmon resonance detector system such as the BIAcore assay system (Pharmacia, Piscataway, N.J.). The BIAcore system may be carried out using the manufacturer's protocol. This assay essentially involves the covalent binding of either MK61 polypeptide or an MK61 binding partner to a dextran-coated sensor chip which is located in a detector. The test compound and the other complementary protein can then be injected, either simultaneously or sequentially, into the chamber containing the sensor chip. The amount of complementary protein that binds can be assessed based on the change in molecular mass which is physically associated with the dextran-coated side of the sensor chip. The change in molecular mass can be measured by the detector system.

In some cases, it may be desirable to evaluate two or more test compounds together for their ability to increase or decrease the formation of a complex between an MK61 polypeptide and an MK61 binding partner. In these cases, the assays set forth herein can be readily modified by adding such additional test compound(s) either simultaneous with, or subsequent to, the first test compound. The remainder of the steps in the assay are as set forth herein.

In vitro assays such as those described herein may be used advantageously to screen large numbers of compounds for effects on complex formation by an MK61 polypeptide and an MK61 binding partner. The assays may be automated to screen compounds generated in phage display, synthetic peptide and chemical synthesis libraries.

Compounds which increase or decrease the formation of a complex between an MK61 polypeptide and an MK61 binding partner may also be screened in cell culture using cells and cell lines expressing either MK61 polypeptide or MK61 binding partner. Cells and cell lines may be obtained from any mammal, but preferably will be from human or other primate, canine or rodent sources. The binding of an MK61 polypeptide to cells expressing MK61 binding partner at the surface is evaluated in the presence or absence of test molecules, and the extent of binding may be determined by, for example, flow cytometry using a biotinylated antibody to an MK61 binding partner. Cell culture assays can be used advantageously to further evaluate compounds that score positive in protein binding assays described herein.

Cell cultures can also be used to screen the impact of a drug candidate. For example, drug candidates may decrease or increase the expression of the MK61 gene. In certain embodiments, the amount of MK61 polypeptide that is produced may be measured after exposure of the cell culture to the drug candidate. In certain embodiments, one may detect the actual impact of the drug candidate on the cell culture. For example, the overexpression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide may result in, or be associated with, a disease or pathological condition. In such cases, one may test a drug candidate's ability to decrease the production of such a metabolic product in a cell culture.

A yeast two-hybrid system (Chien et al., *Proc. Natl. Acad. Sci. USA*, 88:9578-9583 (1991)) can be used to identify novel polypeptides that bind to, or interact with, MK61 polypeptides. As an example, hybrid constructs comprising DNA encoding a cytoplasmic domain of an MK61 polypeptide fused to a yeast GAL4-DNA binding domain may be used as a two-hybrid bait plasmid. Positive clones emerging from the screening may be characterized further to identify interacting proteins.

P38 Inhibitors

A new approach to intervention between the extracellular stimulus and the secretion of IL-1 and TNFα from the cell involves blocking signal transduction through inhibition of a kinase which lies on the signal pathway. One example is through inhibition of P-38 (also called "RK" or "SAPK-2", Lee et al., *Nature*, 372:739 (1994)), a known ser/thr kinase (clone reported in Han et al., *Biochimica Biophysica Acta*, 1265:224-227 (1995)). A linear relationship has been shown for effectiveness in a competitive binding assay to P-38, and the same inhibitor diminishing the levels of IL-1 secretion from monocytes following LPS stimulation. Following LPS stimulation of monocytes, the levels of messenger RNA for TNFα have been shown to increase 100 fold, but the protein levels of TNFα are increased 10,000 fold. Thus, a considerable amplification of the TNF signaling occurs at the translational level. Following LPS stimulation of monocytes in the presence of a P-38 inhibitor, the levels of mRNA are not affected, but the levels of final TNF protein are dramatically reduced (up to 80-90% depending on the effectiveness of the P-38 inhibitor). Thus, the above experiments lend strong support to the conclusion that inhibition of P-38 leads to diminished translational efficiency. Further evidence that TNFα is under translational control is found in the deletion experiments of Beutler et al. and Lee, wherein segments of 3' untranslated mRNA (3' UTR) are removed resulting in high translational efficiency for TNFα. More importantly, the P-38 inhibitors did not have an effect on the level of TNFα (i.e., translational efficiency) when the appropriate segments of TNFα mRNA are deleted. Thus, the correlative data between the level of binding of inhibitors to P-38 and the diminished IL-1 and TNFα levels following LPS stimulation with the same inhibitors, plus the above biochemical evidence regarding the effect of P-38 inhibitors on translational efficiency of both TNFα and IL-1 make a strong cause and effect relationship. The role of P-38 in the cell is still being delineated; so therefore, other beneficial effects regarding inflammatory diseases or other disease states obtained from its inhibition maybe forthcoming.

Elevated levels of TNFα and/or IL-1 may contribute to the onset, etiology, or exacerbate a number of disease states, including, but not limited to: rheumatoid arthritis; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; antiviral therapy including those viruses sensitive to TNFα inhibition—HIV-1, HIV-2, HIV-3, cytomegalovirus (CMV), influenza, adenovirus, and the herpes viruses including HSV-1, HSV-2, and herpes zoster; muscle degeneration; cachexia; Reiter's syndrome; type II diabetes; bone resorption diseases; graft vs. host reaction; ischemia reperfusion injury; atherosclerosis; brain trauma; Alzheimer's disease; multiple sclerosis; cerebral malaria; sepsis; septic shock; toxic shock syndrome; fever and myalgias due to infection.

Substituted imidazole, pyrrole, pyridine, pyrimidine and the like compounds have been described for use in the treatment of cytokine mediated diseases by inhibition of proinflammatory cytokines, such as IL-1, IL-6, IL-8, and TNF. Substituted imidazoles for use in the treatment of cytokine mediated diseases have been described in U.S. Pat. No. 5,593,992; WO93/14081; WO97/18626; WO96/21452; WO96/21654; WO96/40143; WO97/05878; and WO97/05878. Substituted imidazoles for use in the treatment of inflammation has been described in U.S. Pat. No. 3,929,807. Substituted pyrrole compounds for use in the treatment of cytokine mediated diseases have been described in WO97/05877; WO97/05878; WO97/16426; WO97/16441; and WO97/16442. Substituted aryl and heteroaryl fused pyrrole compounds for use in the treatment of cytokine mediated diseases have been described in WO98/22457. Substituted pyridine, pyrimidine, pyrimidinone, and pyridazine compounds for use in the treatment of cytokine mediated diseases have been described in WO98/24780; WO98/24782; WO99/24404; and WO99/32448.

Internalizing Proteins

The TAT protein sequence (from HIV) can be used to internalize proteins into a cell by targeting the lipid bi-layer component of the cell membrane. See e.g., Falwell et al., *Proc. Natl. Acad. Sci. USA*, 91:664-668 (1994). For example, an 11 amino acid sequence (YGRKKRRQRRR; SEQ id NO: X) of the HIV tat protein (termed the "protein transduction domain", or TAT PDT) has shown to mediate delivery of large bioactive proteins such as β-galactosidase and $^{p27}$Kip across the cytoplasmic membrane and the nuclear membrane of a cell. See Schwarze et al., *Science*, 285:1569-1572 (1999); and Nagahara et al., *Nature Medicine*, 4:1449-1452 (1998). Schwarze et al., supra, demonstrated that cultured cells acquired β-galactosidase activity when exposed to a fusion of the TAT-PDT and β-galactosidase. Injection of mice with TAT-β-gal fusion proteins resulted in β-gal expression in a number of tissues, including liver, kidney, lung, heart and brain tissue.

It will thus be appreciated that the TAT protein sequence may be used to internalize a desired protein or polypeptide into a cell. In the context of the present invention, the TAT protein sequence can be fused to another molecule such as a MK61 antagonist (i.e. anti-MK61 selective binding agent, small molecule, soluble receptor, or antisense oligonucleotide) can be administered intracellularly to inhibit the activity of an MK61 molecule. As used herein, the term "MK61 molecule" refers to both MK61 nucleic acid molecules and MK61 polypeptides as defined herein. Where desired, the MK61 protein itself or a peptide fragment or modified form of MI61, may be fused to such a protein transducer for administering to cells using the procedures described above.

Cell Source Identification Using MK61 Polypeptides

In accordance with certain embodiments of the invention, it may be useful to be able to determine the source of a certain cell type associated with an MK61 polypeptide. For example, it may be useful to determine the origin of a disease or pathological condition as an aid in selecting an appropriate therapy.

Therapeutic Uses

The polypeptides and agonists and antagonists of the invention are also useful in the diagnosis and treatment of a number of diseases and disorders, including those recited herein. These include, but are not limited to diseases and disorders involving leukocyte and/or osteoclast proliferation, differentiation, survival, and/or apoptosis. The polypeptides and agonists and antagonists of the invention are also useful in regulating growth, survival and/or apoptosis of lymphoma, leukemia, and other cancer cells.

hMK61T1 was identified from a PMA treated cancer cell line. Therefore, production of the hMK61T1 cell-surface receptor may be regulated by PMA and/or other growth signals at the RNA splicing level. A peptide corresponding to a part of the extracellular domain of hMK61T1 was identified in human urine and serum through proteomics analysis. Furthermore, selective expression of hMK61 was observed in spleen, lymph nodes, peripheral blood leukocytes, and fetal liver as determined by Northern blotting. The polypeptides and agonists and antagonists of the invention are thus also useful in the diagnosis and/or treatment of disorders of the immune system (as is described herein), as well as in the protection and regeneration of the liver.

Many diseases and medical conditions are associated with TNF and are often categorized as inflammatory conditions. TNF-associated diseases include, but are not limited to, spontaneous or experimental diseases or medical conditions if associated with elevated levels of TNF in bodily fluids or tissue, or if cells or tissues taken from the body produce elevated levels of TNF in culture. In many cases, TNF-associated diseases may also be recognized by: (1) pathological findings associated with the disease or medical condition can be mimicked experimentally in animals by the administration or upregulation of expression of TNF, or (2) a pathology induced in experimental animal models of the disease or medical condition can be inhibited or abolished by treatment with agents that inhibit the action of TNF. It will be understood, however, that the mechanism of action of the MK61 polypeptides is not necessarily the inhibition of TNF.

A non-exclusive list of acute and chronic TNF-associated diseases includes, but is not limited to, the following: cachexia/anorexia; cancer (e.g., leukemias); chronic fatigue syndrome; coronary conditions and indications, including congestive heart failure, coronary restenosis, myocardial infarction, and coronary artery bypass graft; depression; diabetes (e.g., juvenile onset Type 1 and diabetes mellitus); endometriosis, endometritis, and related conditions; fibromyalgia or analgesia; graft versus host rejection; hyperalgesia; inflammatory bowel diseases, including Crohn's disease and *Clostridium difficile*-associated diarrhea; ischemic, including cerebral ischemia (brain injury as a result of trauma, epilepsy, hemorrhage or stroke, each of which may lead to neurodegeneration); lung diseases (e.g., adult respiratory distress syndrome, asthma, and pulmonary fibrosis); multiple sclerosis; neuroinflammatory diseases; ocular diseases and conditions, including corneal transplant, ocular degeneration and uveitis; pain, including cancer-related pain; pancreatitis; periodontal diseases; prostatitis (bacterial or non-bacterial) and related conditions; psoriasis and related conditions; pulmonary fibrosis; reperfusion injury; rheumatic diseases (e.g., rheumatoid arthritis, osteoarthritis, juvenile (rheumatoid) arthritis, seronegative polyarthritis, ankylosing spondylitis, Reiter's syndrome and reactive arthritis, Still's disease, psoriatic arthritis, enteropathic arthritis, polymyositis, dermatomyositis, scleroderma, systemic sclerosis, vasculitis (e.g., Kawasaki's disease), cerebral vasculitis, Lyme disease, *staphylococcal*-induced ("septic") arthritis, Sjögren's syndrome, rheumatic fever, polychondritis and polymyalgia rheumatica and giant cell arteritis); septic shock; side effects from radiation therapy; systemic lupus erythematosus; temporal mandibular joint disease; thyroiditis; tissue transplantation or an inflammatory condition resulting from strain, sprain: cartilage damage, trauma, orthopedic surgery, infection (e.g., HIV, *Clostridium difficile* and related species) or other disease process.

TNFα inhibitors may act by downregulating or inhibiting TNF production, binding free TNF, interfering with TNF binding to its receptor, or interfering with modulation of TNF signaling after binding to its receptor. The term "TNFα inhibitor" thus includes solubilized TNF receptors, antibodies to TNF, antibodies to TNF receptor, inhibitors of TNFα converting enzyme (TACE), and other molecules that affect TNF activity.

TNFα inhibitors of various kinds are disclosed in the art, including the following references:

European patent applications 308 378; 422 339; 393 438; 398 327; 412 486; 418 014, 417 563, 433 900; 464 533; 512 528; 526 905; 568 928; 663 210; 542 795; 818 439; 664 128; 542 795; 741 707; 874 819; 882 714; 880 970; 648 783; 731 791; 895 988; 550 376; 882 714; 853 083; 550 376; 943 616;

U.S. Pat. Nos. 5,136,021; 5,929,117; 5,948,638; 5,807, 862; 5,695,953; 5,834,435; 5,817,822; 5,830,742; 5,834,435; 5,851,556; 5,853,977; 5,359,037; 5,512,544; 5,695,953; 5,811,261; 5,633,145; 5,863,926; 5,866,616; 5,641,673; 5,869,677; 5,869,511; 5,872,146; 5,854,003; 5,856,161; 5,877,222; 5,877,200; 5,877,151; 5,886,010; 5,869,660; 5,859,207; 5,891,883; 5,877,180; 5,955,480; 5,955,476; 5,955,435;

International (WO) patent applications 90/13575, 91/03553, 92/01002, 92/13095, 92/16221, 93/07863, 93/21946, 93/19777, 95/34326, 96/28546, 98/27298, 98/30541, 96/38150, 96/38150, 97/18207, 97/15561, 97/12902, 96/25861, 96/12735, 96/11209, 98/39326, 98/39316, 98/38859, 98/39315, 98/42659, 98/39329, 98/43959, 98/45268, 98/47863, 96/33172, 96/20926, 97/37974, 97/37973, 96/35711, 98/51665, 98/43946, 95/04045, 98/56377, 97/12244, 99/00364, 99/00363, 98/57936, 99/01449, 99/01139, 98/56788, 98/56756, 98/53842, 98/52948, 98/52937, 99/02510, 97/43250, 99/06410, 99/06042, 99/09022, 99/08688, 99/07679, 99/09965, 99/07704, 99/06041, 99/37818, 99/37625, 97/11668;

Japanese (JP) patent applications 10147531, 10231285, 10259140, and 10130149, 10316570, 11001481, and 127,800/1991; German (DE) application 19731521; British (GB) applications 2 218 101, 2 326 881, 2 246 569.

For purposes of this invention, the molecules disclosed in these references and the molecules disclosed in the references (see below) are collectively termed "TNFα inhibitors".

For example, EP 393,438 and EP 422,339 teach the amino acid and nucleic acid sequences of a soluble TNF receptor type I (also known as sTNFR-I or 30 kDa TNF inhibitor) and a soluble TNF receptor type II (also known as sTNFR-II or 40 kDa TNF inhibitor), collectively termed "sTNFRs", as well as modified forms thereof (e.g., fragments, functional derivatives and variants). EP 393,438 and EP 422,339 also disclose methods for isolating the genes responsible for coding the inhibitors, cloning the gene in suitable vectors and cell types, and expressing the gene to produce the inhibitors.

sTNFR-I and sTNFR-II are members of the nerve growth factor/TNF receptor superfamily of receptors which includes the nerve growth factor receptor (NGF), the B-cell antigen CD40, 4-1BB, the rat T-cell antigen MRC OX40, the fas antigen, and the CD27 and CD30 antigens (Smith et al., Science, 248:1019-1023 (1990)). The most conserved feature among this group of cell surface receptors is the cysteine-rich extracellular ligand binding domain, which can be divided into four repeating motifs of about forty amino acids and which contains 4-6 cysteine residues at positions which are well conserved (Smith et al. (1990), supra).

As contemplated by the present invention, an MK61 polypeptide may be administered as an adjunct to other therapy and also with other pharmaceutical formulations suitable for the indication being treated. A MK61 polypeptide and any of one or more additional therapies or pharmaceutical formulations may be administered separately, sequentially, or simultaneously.

In a specific embodiment, the present invention is directed to the use of a MK61 polypeptide in combination (pretreatment, post-treatment, or concurrent treatment) with any of one or more interleukin-1 (IL-1) inhibitors for the treatment of TNF-responsive disease. Classes of interleukin-1 inhibitors include interleukin-1 receptor antagonists (any compound capable of specifically preventing activation of cellular receptors to IL-1) such as IL-1ra, as described below; anti-IL-1 receptor monoclonal antibodies (e.g., EP 623,674); IL-1 binding proteins such as soluble IL-1 receptors (e.g., U.S. Pat. Nos. 5,492,888, 5,488,032, 5,464,937, 5,319,071 and 5,180,812); anti-IL-1 monoclonal antibodies (e.g., WO95/01997, WO94/02627, WO90/06371, U.S. Pat. No. 4,935,343, EP 364,778, EP 267,611 and EP 220,063); IL-1 receptor accessory proteins (e.g., WO96/23067), and other compounds and proteins which block in vivo synthesis or extracellular release of IL-1.

Interleukin-1 receptor antagonist (IL-1ra) is a human protein that acts as a natural inhibitor of interleukin-1. Interleukin-1 receptor antagonists, as well as the methods of making and methods of using thereof, are described in U.S. Pat. No. 5,075,222; WO91/08285; WO91/17184; AU9173636; WO92/16221; WO93/21946; WO94/06457; WO94/21275; FR2706772; WO94/21235; DE4219626; WO94/20517; WO96/22793 and WO97/28828, the disclosures of which are incorporated herein by reference. The proteins include glycosylated as well as non-glycosylated IL-1 receptor antagonists.

Specifically, three preferred forms of IL-1ra (IL-1raα, IL-1raβ and IL-1rax), each being encoded by the same DNA coding sequence and variants thereof, are disclosed and described in U.S. Pat. No. 5,075,222. Methods for producing IL-1 inhibitors, particularly IL-1ras, are also disclosed in the 5,075,222 patent.

An additional class of interleukin-1 inhibitors includes compounds capable of specifically preventing activation of cellular receptors to IL-1. Such compounds include IL-1 binding proteins, such as soluble receptors and monoclonal antibodies. Such compounds also include monoclonal antibodies to the receptors.

A further class of interleukin-1 inhibitors includes compounds and proteins which block in vivo synthesis and/or extracellular release of IL-1. Such compounds include agents which affect transcription of IL-1 genes or processing of IL-1 preproteins.

In a specific embodiment, the present invention is directed to the use of an MK61 polypeptide in combination (pretreatment, post-treatment or concurrent treatment) with secreted or soluble human fas antigen or recombinant versions thereof (WO96/20206 and Mountz et al., J. Immunology, 155:4829-4837; and EP 510,691, the disclosures of which are hereby incorporated by reference). WO96/20206 discloses secreted human fas antigen (native and recombinant, including an Ig fusion protein), methods for isolating the genes responsible for coding the soluble recombinant human fas antigen, methods for cloning the gene in suitable vectors and cell types, and methods for expressing the gene to produce the inhibitors. EP 510,691 teaches DNAs coding for human fas antigen, including soluble fas antigen, vectors expressing for said DNAs and transformants transfected with the vector. When administered parenterally, doses of a secreted or soluble fas antigen fusion protein each are generally from about 1 micrograms/kg to about 100 micrograms/kg.

Present treatment of TNF-responsive diseases, including acute and chronic inflammation such as rheumatic diseases, commonly includes the use of first line drugs for control of pain and inflammation; these drugs are classified as non-steroidal, anti-inflammatory drugs (NSAIDs). Secondary treatments include corticosteroids, slow acting antirheumatic drugs (SAARDs) or disease modifying (DM) drugs. Information regarding the following compounds can be found in The Merck Manual of Diagnosis and Therapy, Sixteenth Edition, Merck, Sharp & Dohme Research Laboratories, Merck & Co., Rahway, N.J. (1992) and in Pharmaprojects, PJB Publications Ltd.

In a specific embodiment, the present invention is directed to the use of an MK61 polypeptide and any of one or more NSAIDs for the treatment of TNF-responsive diseases, including acute and chronic inflammation such as rheumatic diseases; and graft versus host disease. NSAIDs owe their anti-inflammatory action, at least in part, to the inhibition of prostaglandin synthesis (Goodman and Gilman in "The Pharmacological Basis of Therapeutics," MacMillan 7th Edition (1985)). NSAIDs can be characterized into at least nine groups: (1) salicylic acid derivatives; (2) propionic acid derivatives; (3) acetic acid derivatives; (4) fenamic acid derivatives; (5) carboxylic acid derivatives; (6) butyric acid derivatives; (7) oxicams; (8) pyrazoles and (9) pyrazolones.

In a more specific embodiment, the present invention is directed to the use of a MK61 polypeptide in combination (pretreatment, post-treatment or concurrent treatment) with any of one or more salicylic acid derivatives, prodrug esters or pharmaceutically acceptable salts thereof. Such salicylic acid derivatives, prodrug esters and pharmaceutically acceptable salts thereof comprise: acetaminosalol, aloxiprin, aspirin, benorylate, bromosaligenin, calcium acetylsalicylate, choline magnesium trisalicylate, magnesium salicylate, choline salicylate, diflusinal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acetic acid, salsalate, sodium salicylate and sulfasalazine. Structurally related salicylic acid derivatives having similar analgesic and anti-inflammatory properties are also intended to be encompassed by this group.

In a more specific embodiment, the present invention is directed to the use of a MK61 polypeptide in combination (pretreatment, post-treatment or concurrent treatment) with any of one or more propionic acid derivatives, prodrug esters or pharmaceutically acceptable salts thereof. The propionic acid derivatives, prodrug esters and pharmaceutically acceptable salts thereof comprise: alminoprofen, benoxaprofen, bucloxic acid, carprofen, dexindoprofen, fenoprofen, flunoxaprofen, fluprofen, flurbiprofen, furcloprofen, ibuprofen, ibuprofen aluminum, ibuproxam, indoprofen, isoprofen, ketoprofen, loxoprofen, miroprofen, naproxen, naproxen sodium, oxaprozin, piketoprofen, pimeprofen, pirprofen, pranoprofen, protizinic acid, pyridoxiprofen, suprofen, tiaprofenic acid and tioxaprofen. Structurally related propionic acid derivatives having similar analgesic and anti-inflammatory properties are also intended to be encompassed by this group.

In a more specific embodiment, the present invention is directed to the use of a MK61 polypeptide in combination (pretreatment, post-treatment or concurrent treatment) with any of one or more acetic acid derivatives, prodrug esters or pharmaceutically acceptable salts thereof. The acetic acid derivatives, prodrug esters and pharmaceutically acceptable salts thereof comprise: acemetacin, alclofenac, amfenac, bufexamac, cinmetacin, clopirac, delmetacin, diclofenac potassium, diclofenac sodium, etodolac, felbinac, fenclofenac, fenclorac, fenclozic acid, fentiazac, furofenac, glucametacin, ibufenac, indomethacin, isofezolac, isoxepac, lonazolac, metiazinic acid, oxametacin, oxpinac, pimetacin, proglumetacin, sulindac, talmetacin, tiaramide, tiopinac, tolmetin, tolmetin sodium, zidometacin and zomepirac. Structurally related acetic acid derivatives having similar analgesic and anti-inflammatory properties are also intended to be encompassed by this group.

In a more specific embodiment, the present invention is directed to the use of a MK61 polypeptide in combination (pretreatment, post-treatment or concurrent treatment) with any of one or more fenamic acid derivatives, prodrug esters or pharmaceutically acceptable salts thereof. The fenamic acid derivatives, prodrug esters and pharmaceutically acceptable salts thereof comprise: enfenamic acid, etofenamate, flufenamic acid, isonixin, meclofenamic acid, meclofenamate sodium, medofenamic acid, mefenamic acid, niflumic acid, talniflumate, terofenamate, tolfenamic acid and ufenamate. Structurally related fenamic acid derivatives having similar analgesic and anti-inflammatory properties are also intended to be encompassed by this group.

In a more specific embodiment, the present invention is directed to the use of a MK61 polypeptide in combination (pretreatment, post-treatment or concurrent treatment) with any of one or more carboxylic acid derivatives, prodrug esters or pharmaceutically acceptable salts thereof. The carboxylic acid derivatives, prodrug esters and pharmaceutically acceptable salts thereof which can be used comprise: clidanac, diflunisal, flufenisal, inoridine, ketorolac and tinoridine. Structurally related carboxylic acid derivatives having similar analgesic and anti-inflammatory properties are also intended to be encompassed by this group.

In a more specific embodiment, the present invention is directed to the use of a MK61 polypeptide in combination (pretreatment, post-treatment or concurrent treatment) with any of one or more butyric acid derivatives, prodrug esters or pharmaceutically acceptable salts thereof. The butyric acid derivatives, prodrug esters and pharmaceutically acceptable salts thereof comprise: bumadizon, butibufen, fenbufen and xenbucin. Structurally related butyric acid derivatives having similar analgesic and anti-inflammatory properties are also intended to be encompassed by this group.

In a more specific embodiment, the present invention is directed to the use of a MK61 polypeptide in combination (pretreatment, post-treatment or concurrent treatment) with any of one or more oxicams, prodrug esters or pharmaceutically acceptable salts thereof. The oxicams, prodrug esters and pharmaceutically acceptable salts thereof comprise: droxicam, enolicam, isoxicam, piroxicam, sudoxicam, tenoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

In a more specific embodiment, the present invention is directed to the use of a MK61 polypeptide in combination (pretreatment, post-treatment, or concurrent treatment) with any of one or more pyrazoles, prodrug esters or pharmaceutically acceptable salts thereof. The pyrazoles, prodrug esters and pharmaceutically acceptable salts thereof which may be used comprise: difenamizole and epirizole. Structurally related pyrazoles having similar analgesic and anti-inflammatory properties are also intended to be encompassed by this group.

In a more specific embodiment, the present invention is directed to the use of a MK61 polypeptide in combination (pretreatment, post-treatment or concurrent treatment) with any of one or more pyrazolones, prodrug esters or pharmaceutically acceptable salts thereof. The pyrazolones, prodrug esters and pharmaceutically acceptable salts thereof which may be used comprise: apazone, azapropazone, benzpiperylon, feprazone, mofebutazone, morazone, oxyphenbutazone, phenylbutazone, pipebuzone, propylphenazone, ramifenazone, suxibuzone and thiazolinobutazone. Structurally related pyrazalones having similar analgesic and anti-inflammatory properties are also intended to be encompassed by this group.

In a more specific embodiment, the present invention is directed to the use of a MK61 polypeptide in combination (pretreatment, post-treatment or concurrent treatment) with any of one or more of the following NSAIDs: ε-acetamidocaproic acid, S-adenosylmethionine, 3-amino-4-hydroxybutyric acid, amixetrine, anitrazafen, antrafenine, bendazac, bendazac lysinate, benzydamine, beprozin, broperamole, bucolome, bufezolac, ciproquazone, cloximate, dazidamine, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isonixirn, lefetamine HCl, leflunomide, lofemizole, lotifazole, lysin clonixinate, meseclazone, nabumetone, nictindole, nimesulide, orgotein, orpanoxin, oxaceprol, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802, AFP860, AI77B, AP504, AU8001, BPPC, BW540C, CHINOIN 127, CN100, EB382, EL508, F1044, FK-506, GV3658, ITF182, KCNTEI6090, KME4, LA2851, MR714, MR897, MY309, ON03144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301 and WY41770. Structurally related NSAIDs having similar analgesic and anti-inflammatory properties to the NSAIDs are also intended to be encompassed by this group.

In a more specific embodiment, the present invention is directed to the use of a MK61 polypeptide in combination (pretreatment, post-treatment or concurrent treatment) with any of one or more corticosteroids, prodrug esters or pharmaceutically acceptable salts thereof for the treatment of TNF-responsive diseases, including acute and chronic inflammation such as rheumatic diseases, graft versus host disease and multiple sclerosis. Corticosteroids, prodrug esters and pharmaceutically acceptable salts thereof include hydrocortisone and compounds which are derived from hydrocortisone, such as 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flucinolone acetonide, flunisolide, fluocinonide, fluorocinolone acetonide, fluocortin butyl, fluocortolone, fluocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone, hydrocortisone acetate, hydrocortisone butyrate, hydrocortisone phosphate, hydrocortisone 21-sodium succinate, hydrocortisone tebutate, mazipredone, medrysone, meprednisone, methylprednisolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar analgesic and anti-inflammatory properties are also intended to be encompassed by this group.

In a more specific embodiment, the present invention is directed to the use of a MK61 polypeptide in combination (pretreatment, post-treatment or concurrent treatment) with any of one or more slow-acting antirheumatic drugs (SAARDs) or disease modifying antirheumatic drugs (DMARDS), prodrug esters or pharmaceutically acceptable salts thereof for the treatment of TNF-responsive diseases, including acute and chronic inflammation such as rheumatic diseases, graft versus host disease and multiple sclerosis. SAARDs or DMARDS, prodrug esters and pharmaceutically acceptable salts thereof comprise: allocupreide sodium, auranofin, aurothioglucose, aurothioglycanide, azathioprine, brequinar sodium, bucillamine, calcium 3-aurothio-2-propanol-1-sulfonate, chlorambucil, chloroquine, clobuzarit, cuproxoline, cyclophosphamide, cyclosporin, dapsone, 15-deoxyspergualin, diacerein, glucosamine, gold salts (e.g., cycloquine gold salt, gold sodium thiomalate, gold sodium thiosulfate), hydroxychloroquine, hydrbxychloroquine sulfate, hydroxyurea, kebuzone, levamisole, lobenzarit, melittin, 6-mercaptopurine, methotrexate, mizoribine, mycophenolate mofetil, myoral, nitrogen mustard, D-penicillamine, pyridinol imidazoles such as SKNF86002 and SB203580, rapamycin, thiols, thymopoietin and vincristine. Structurally related SAARDs or DMARDs having similar analgesic and anti-inflammatory properties are also intended to be encompassed by this group.

In a more specific embodiment, the present invention is directed to the use of a MK61 polypeptide in combination (pretreatment, post-treatment or concurrent treatment) with any of one or more COX2 inhibitors, prodrug esters or pharmaceutically acceptable salts thereof for the treatment of TNF-responsive diseases, including acute and chronic inflammation. Examples of COX2 inhibitors, prodrug esters or pharmaceutically acceptable salts thereof include, for example, celecoxib. Structurally related COX2 inhibitors having similar analgesic and anti-inflammatory properties are also intended to be encompassed by this group.

In a more specific embodiment, the present invention is directed to the use of a MK61 polypeptide in combination (pretreatment, post-treatment or concurrent treatment) with any of one or more antimicrobials, prodrug esters or pharmaceutically acceptable salts thereof for the treatment of TNF-responsive diseases, including acute and chronic inflammation. Antimicrobials include, for example, the broad classes of penicillins, cephalosporins and other beta-lactams, aminoglycosides, azoles, quinolones, macrolides, rifamycins, tetracyclines, sulfonamides, lincosamides and polymyxins. The penicillins include, but are not limited to penicillin G, penicillin V, methicillin, nafcillin, oxacillin, cloxacillin, dicloxacillin, floxacillin, ampicillin, ampicillin/sulbactam, amoxicillin, amoxicillin/clavulanate, hetacillin, cyclacillin, bacampicillin, carbenicillin, carbenicillin indanyl, ticarcillin, ticarcillin/clavulanate, azlocillin, mezlocillin, peperacillin, and mecillinam. The cephalosporins and other beta-lactams include, but are not limited to cephalothin, cephapirin, cephalexin, cephradine, cefazolin, cefadroxil, cefaclor, cefamandole, cefotetan, cefoxitin, ceruroxime, cefonicid, ceforadine, cefixime, cefotaxime, moxalactam, ceftizoxime, cetriaxone, cephoperazone, ceftazidime, imipenem and aztreonam. The aminoglycosides include, but are not limited to streptomycin, gentamicin, tobramycin, amikacin, netilmicin, kanamycin and neomycin. The azoles include, but are not limited to fluconazole. The quinolones include, but are not limited to nalidixic acid, norfloxacin, enoxacin, ciprofloxacin, ofloxacin, sparfloxacin and temafloxacin. The macrolides include, but are not limited to erythomycin, spiramycin and azithromycin. The rifamycins include, but are not limited to rifampin. The tetracyclines include, but are not limited to spicycline, chlortetracycline, clomocycline, demeclocycline, deoxycycline, guamecycline, lymecycline, meclocycline, methacycline, minocycline, oxytetracycline, penimepicycline, pipacycline, rolitetracycline, sancycline, senociclin and tetracycline. The sulfonamides include, but are not limited to sulfanilamide, sulfamethoxazole, sulfacetamide, sulfadiazine, sulfisoxazole and co-trimoxazole (trimethoprim/sulfamethoxazole). The lincosamides include, but are not limited to clindamycin and lincomycin. The polymyxins (polypeptides) include, but are not limited to polymyxin B and colistin.

MK61 Compositions and Administration

Therapeutic compositions within the scope of the present invention include MK61 pharmaceutical compositions that may comprise a therapeutically effective amount of an MK61 polypeptide or an MK61 nucleic acid molecule in admixture with a pharmaceutically or physiologically acceptable formulation agent selected for suitability with the mode of administration to a human or non-human animal such as a mammal. Pharmaceutical compositions may comprise a therapeutically effective amount of one or more MK61 selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (*Remington's Pharmaceutical Sciences*, 18$^{th}$ Edition, A. R. Gennaro, ed., Mack Publishing Company (1990).

The optimal pharmaceutical composition will be determined by one skilled in the art depending upon, for example, the intended route of administration, delivery format and desired dosage. See, for example, *Remington's Pharmaceutical Sciences*, supra. Such compositions may influence the physical state, stability, rate of in vivo release and rate of in vivo clearance of the MK61 molecule.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefor. In one embodiment of the present invention, MK61 polypeptide compositions may be prepared for storage by mixing the selected composition having the desired degree of purity with optional formulation agents (*Remington's Pharmaceutical Sciences*, supra) in the form of a lyophilized cake or an aqueous solution. Further, the MK61 polypeptide product may be formulated as a lyophilizate using appropriate excipients such as sucrose.

The MK61 pharmaceutical compositions can be selected for parenteral delivery. Alternatively, the compositions may be selected for inhalation or for delivery through the digestive tract, such as orally, or through other delivery routes known in the art. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired MK61 molecule in a pharmaceutically acceptable vehicle. A particularly suitable vehicle for parenteral injection is sterile distilled water in which an MK61 molecule is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, an MK61 molecule may be formulated as a dry powder for inhalation. MK61 polypeptide or MK61 nucleic acid molecule inhalation solutions may also be formulated with a propellant for aerosol delivery. In yet another embodiment, solutions may be nebulized. Pulmonary administration is further described in PCT application no. PCT/US94/001875, which describes pulmonary delivery of chemically modified proteins.

It is also contemplated that certain formulations may be administered orally. In one embodiment of the present invention, MK61 molecules which are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the MK61 molecule. Diluents, flavorings, low melting point waxes, vegetable oils, lubricants, suspending agents, tablet disintegrating agents, and binders may also be employed.

Another pharmaceutical composition may involve an effective quantity of MK61 molecules in a mixture with non-toxic excipients which are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional MK61 pharmaceutical compositions will be evident to those skilled in the art, including formulations involving MK61 polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919 and EP 058,481), copolymers of L-glutamic acid and gamma ethyl-L-glutamate (Sidman et al., *Biopolymers,* 22:547-556 (1983)), poly (2-hydroxyethyl-methacrylate) (Langer et al., *J. Biomed. Mater. Res.,* 15:167-277 (1981) and Langer, *Chem. Tech.,* 12:98-105 (1982)), ethylene vinyl acetate (Langer et al., supra) or poly-D(–)-3-hydroxybutyric acid (EP 133,988). Sustained release compositions may also include liposomes, which can be prepared by any of several methods known in the art. See e.g., Eppstein et al., *Proc. Natl. Acad. Sci. USA,* 82:3688-3692 (1985); EP 036,676; EP 088,046 and EP 143, 949.

The MK61 pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The effective amount of an MK61 pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the MK61 molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 μg/kg to up to about 100 mg/kg or more, depending on the factors mentioned above. In other embodiments, the dosage may range from 0.1 μg/kg up to about 100 mg/kg; or 1 μg/kg up to about 100 mg/kg; or 5 μg/kg up to about 100 mg/kg.

The frequency of dosing will depend upon the pharmacokinetic parameters of the MK61 molecule in the formulation used. Typically, a clinician will administer the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data which is routinely obtained.

The route of administration of the pharmaceutical composition is in accord with known methods, e.g. orally, through injection by intravenous, intraperitoneal, intracerebral (intraparenchymal), intracerebroventricular, intramuscular, intra-ocular, intraarterial, intraportal, or intralesional routes; by sustained release systems or by implantation devices. Where desired, the compositions may be administered by bolus injection or continuously by infusion, or by implantation device.

Alternatively or additionally, the composition may be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use MK61 pharmaceutical compositions in an ex vivo manner. In such instances, cells, tissues or organs that have been removed from the patient are exposed to MK61 pharmaceutical compositions after which the cells, tissues and/or organs are subsequently implanted back into the patient.

In other cases, an MK61 polypeptide can be delivered by implanting certain cells that have been genetically engineered, using methods such as those described herein, to express and secrete the polypeptide. Such cells may be animal or human cells, and may be autologous, heterologous, or xenogeneic. optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally-silent MK61 gene, or an underexpressed gene, and thereby produce a cell which expresses therapeutically efficacious amounts of MK61 polypeptides.

Homologous recombination is a technique originally developed for targeting genes to induce or correct mutations in transcriptionally active genes (Kucherlapati, *Prog. in Nucl. Acid Res. & Mol. Biol.,* 36:301, (1989)). The basic technique was developed as a method for introducing specific mutations into specific regions of the mammalian genome (Thomas et al., *Cell,* 44:419-428 (1986); Thomas and Capecchi, *Cell,* 51:503-512 (1987); Doetschman et al., *Proc. Natl. Acad. Sci.,* 85:8583-8587 (1988)) or to correct specific mutations within defective genes (Doetschman et al., *Nature,* 330:576-578 (1987)). Exemplary homologous recombination techniques are described in U.S. Pat. No. 5,272,071 (EP 9193051, EP Publication No. 505500 and PCT/US90/07642, International Publication No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA which may interact with or control the expression of an MK61 polypeptide, e.g., flanking sequences. For example, a promoter/enhancer element, a suppressor or an exogenous transcription modulatory element is inserted in the genome of the intended host cell in proximity and orientation sufficient to influence the transcription of DNA encoding the desired MK61 polypeptide. The control element controls a portion of the DNA present in the host cell genome. Thus, the expression of the desired MK61 polypeptide may be achieved not by transfection of DNA that encodes the MK61 gene itself, but rather by the use of targeting DNA (containing regions of homology with the endogenous gene of interest), coupled with DNA regulatory segments that provide the endogenous gene sequence with recognizable signals for transcription of an MK61 gene.

In an exemplary method, the expression of a desired targeted gene in a cell (i.e., a desired endogenous cellular gene) is altered via homologous recombination into the cellular genome at a preselected site by the introduction of DNA which includes at least a regulatory sequence, an exon and a splice donor site. These components are introduced into the chromosomal (genomic) DNA in such a manner that this, in effect, results in the production of a new transcription unit (in which the regulatory sequence, the exon and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, MK61 polypeptide production from a cell's endogenous MK61 gene involves first using homologous recombination to place a recombination sequence from a site-specific recombination system (e.g., Cre/loxP, FLP/FRT) (see, Sauer, *Current Opinion In Biotechnology,* 5:521-527 (1994) and Sauer, *Methods In Enzymology,* 225:890-900 (1993)) upstream (that is, 5' to) of the cell's endogenous genomic MK61 polypeptide coding region. A plasmid containing a recombination site homologous to the site that was placed just upstream of the genomic MK61 polypeptide coding region is introduced into the modified cell line along with the appropriate recombinase enzyme. This recombinase enzyme causes the plasmid to integrate, via the plasmid's recombination site, into the recombination site located just upstream of the genomic MK61 polypeptide coding region in the cell line (Baubonis and Sauer, *Nucleic Acids Res.,* 21:2025-2029, 1993 and O'Gorman et al., *Science,* 251: 1351-1355 (1991)). Any flanking sequences known to increase transcription (e.g., enhancer/promoter, intron or translational enhancer), if properly positioned in this plasmid, would integrate in such a manner as to create a new or modified transcriptional unit resulting in de novo or increased MK61 polypeptide production from the cell's endogenous MK61 gene.

A further method to use the cell line in which the site-specific recombination sequence has been placed just upstream of the cell's endogenous genomic MK61 polypeptide coding region is to use homologous recombination to introduce a second recombination site elsewhere in the cell line's genome. The appropriate recombinase enzyme is then introduced into the two-recombination-site cell line, causing a recombination event (deletion, inversion, or translocation) (Sauer, *Current Opinion In Biotechnology,* supra (1994) and Sauer, *Methods In Enzymology,* supra, (1993)) that would create a new or modified transcriptional unit resulting in de novo or increased MK61 polypeptide production from the cell's endogenous MK61 gene.

An additional approach for increasing, or causing, the expression of MK61 polypeptide from a cell's endogenous MK61 gene involves increasing, or causing, the expression of a gene or genes (e.g., transcription factors) and/or decreasing the expression of a gene or genes (e.g., transcriptional repressors) in a manner which results in de novo or increased MK61 polypeptide production from the cell's endogenous MK61 gene. This method includes the introduction of a non-naturally occurring polypeptide (e.g., a polypeptide comprising a site-specific DNA binding domain fused to a transcriptional factor domain) into the cell such that de novo or increased MK61 polypeptide production from the cell's endogenous MK61 gene results.

The present invention further relates to DNA constructs useful in the method of altering expression of a target gene. In certain embodiments, the exemplary DNA constructs comprise: (a) one or more targeting sequences; (b) a regulatory sequence; (c) an exon and (d) an unpaired splice-donor site. The targeting sequence in the DNA construct directs the integration of elements (a)-(d).into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of MK61 polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence(s) upon insertion into the cell in that it will hybridize to its homologous region within the genome. It is conventionally believed that if this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding a MK61 polypeptide, which nucleotides may be used as targeting sequences.

MK61 polypeptide cell therapy, e.g., the implantation of cells producing MK61 polypeptides, is also contemplated. This embodiment involves implanting cells capable of synthesizing and secreting a biologically active form of MK61 polypeptide. Such MK61 polypeptide-producing cells can be cells that are natural producers of MK61 polypeptides or may be recombinant cells whose ability to produce MK61 polypeptides has been augmented by transformation with a gene encoding the desired MK61 polypeptide or with a gene augmenting the expression of MK61 polypeptide. Such a modification may be accomplished by means of a vector suitable for delivering the gene as well as promoting its expression and secretion. In order to minimize a potential immunological reaction in patients being administered an MK61 polypeptide, as may occur with the administration of a polypeptide of a foreign species, it is preferred that the natural cells producing MK61 polypeptide be of human origin and produce human MK61 polypeptide. Likewise, it is preferred that the recombinant cells producing MK61 polypeptide be transformed with an expression vector containing a gene encoding a human MK61 polypeptide.

Implanted cells may be encapsulated to avoid the infiltration of surrounding tissue. Human or non-human animal cells may be implanted in patients in biocompatible, semipermeable polymeric enclosures or in membranes that allow the release of MK61 polypeptide but prevent the destruction of the cells by the patient's immune system or by other detrimental factors from the surrounding tissue. Alternatively, the patient's own cells, transformed to produce MK61 polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (WO 95/05452 and PCT/US94/C9299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down-regulation in vivo upon implantation into a mammalian host. The devices provide for delivery of the molecules from living cells to specific sites within a recipient. In addition, see U.S. Pat. Nos. 4,892,538, 5,011,472 and 5,106,627. A system for encapsulating living cells is described in PCT Application no. PCT/US91/00157 of Aebischer et al. See also, PCT Application no. PCT/US91/00155 of Aebischer et al.; Winn et al., *Exper. Neurol.*, 113:322-329 (1991), Aebischer et al., *Exper. Neurol.*, 111:269-275 (1991); and Tresco et al., ASAIO, 38:17-23 (1992).

In vivo and in vitro gene therapy delivery of MK61 polypeptides is also envisioned. One example of a gene therapy technique is to use the MK61 gene (either genomic DNA, cDNA and/or synthetic DNA) encoding an MK61 polypeptide which may be operably linked to a constitutive or inducible promoter to form a "gene therapy DNA construct".

The promoter may be homologous or heterologous to the endogenous MK61 gene, provided that it is active in the cell or tissue type into which the construct will be inserted. Other components of the gene therapy DNA construct may optionally include, DNA molecules designed for site-specific integration (e.g., endogenous sequences useful for homologous recombination); tissue-specific promoter, enhancer(s) or silencer(s); DNA molecules capable of providing a selective advantage over the parent cell; DNA molecules useful as labels to identify transformed cells; negative selection systems; cell-specific binding agents (as, for example, for cell targeting); cell-specific internalization factors; and transcription factors to enhance expression by a vector, as well as factors to enable vector manufacture.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain unintegrated.

In yet other embodiments, regulatory elements can be included for the controlled expression of the MK61 gene in the target cell. Such elements are turned on in response to an appropriate effector. In this way, a therapeutic polypeptide can be expressed when desired. One conventional control means involves the use of small molecule dimerizers or rapalogs (as described in WO9641865 (PCT/US96/099486); WO9731898 (PCT/US97/03137) and WO9731899 (PCT/US95/03157)) used to dimerize chimeric proteins which contain a small molecule-binding domain and a domain capable of initiating biological process, such as a DNA-binding protein or a transcriptional activation protein. The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain which results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See, *Science* 287:816-817 and 826-830 (2000).

Other suitable control means or gene switches include, but are not limited to, the following systems. Mifepristone (RU486) is used as a progesterone antagonist. The binding of a modified progesterone receptor ligand-binding domain to the progesterone antagonist activates transcription by forming a dimer of two transcription factors which then pass into the nucleus to bind DNA. The ligand-binding domain is modified to eliminate the ability of the receptor to bind to the natural ligand. The modified steroid hormone receptor system is further described in U.S. Pat. No. 5,364,791; WO9640911 and WO9710337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain/DNA-binding domain/ligand-binding domain to initiate transcription. The ecdysone system is further described in U.S. Pat. No. 5,514, 578; WO9738117; WO9637609; and WO9303162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758; 5,650,298, and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding an MK61 polypeptide into cells via local injection of an MK61 nucleic acid molecule or by other appropriate viral or non-viral delivery vectors (Hefti, *Neurobiology*, 25:1418-1435 (1994)). For example, a nucleic acid molecule encoding an MK61 polypeptide may be contained in an adeno-associated virus (AAV) vector for delivery to the targeted cells (e.g., Johnson, International Publication No. WO95/34670 and International Application No. PCT/US95/07178). The recombinant AAV genome typically contains AAV inverted terminal repeats flanking a DNA sequence encoding an MK61 polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399, 346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 involving adenoviral vectors; U.S. Pat. No. 5,672,510 involving retroviral vectors; and U.S. Pat. No. 5,635,399 involving retroviral vectors expressing cytokines.

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include the use of inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 involving electroporation techniques; WO96/40958 involving nuclear ligands; U.S. Pat. No. 5,679,559 describing a lipoprotein-containing system for gene delivery; U.S. Pat. No. 5,676,954 involving liposome carriers; U.S. Pat. No. 5,593,875 concerning methods for calcium phosphate transfection; and U.S. Pat. No. 4,945,050 wherein biologically active particles are propelled at cells at a speed whereby the particles penetrate the surface of the cells and become incorporated into the interior of the cells.

It is also contemplated that MK61 gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous MK61 polypeptide expression in a cell via gene therapy is to insert one or more enhancer element(s) into the MK61 polypeptide promoter, where the enhancer element(s) can serve to increase transcriptional activity of the MK61 gene. The enhancer element(s) used will be selected based on the tissue in which one desires to activate the gene(s); enhancer element(s) known to confer promoter activation in that tissue will be selected. For example, if a gene encoding an MK61 polypeptide is to be "turned on" in T-cells, the lck promoter enhancer element may be used. Here, the functional portion of the transcriptional element to be added may be inserted into a fragment of DNA containing the MK61 polypeptide promoter (and optionally, inserted into a vector and/or 5' and/or 3' flanking sequence(s), etc.) using standard cloning techniques. This construct, known as a "homologous recombination construct", can then be introduced into the desired cells either ex vivo or in vivo.

Gene therapy also can be used to decrease MK61 polypeptide expression by modifying the nucleotide sequence of the endogenous promoter(s). Such modification is typically accomplished via homologous recombination methods. For example, a DNA molecule containing all or a portion of the promoter of the MK61 gene(s) selected for inactivation can be engineered to remove and/or replace pieces of the promoter that regulate transcription. For example the TATA box and/or the binding site of a transcriptional activator of the promoter may be deleted using standard molecular biology techniques; such deletion can inhibit promoter activity thereby repressing the transcription of the corresponding MK61 gene. The deletion of the TATA box or the transcription activator binding site in the promoter may be accomplished by generating a DNA construct comprising all or the relevant portion of the MK61 polypeptide promoter(s) (from the same or a related species as the MK61 gene(s) to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. The construct will typically contain at least about 500 bases of DNA that correspond to the native. (endogenous) 5' and 3' DNA sequences adjacent to the promoter segment that has been modified. The construct may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Additional Uses of MK61 Nucleic Acids and Polypeptides

Nucleic acid molecules of the present invention (including those that do not themselves encode biologically active polypeptides) may be used to map the locations of the MK61 gene and related genes on chromosomes. Mapping may be done by techniques known in the art, such as PCR amplification and in situ hybridization.

MK61 nucleic acid molecules (including those that do not themselves encode biologically active polypeptides), may be useful as hybridization probes in diagnostic assays to test, either qualitatively or quantitatively, for the presence of an MK61 DNA or corresponding RNA in mammalian tissue or bodily fluid samples.

The present invention thus provides reagents for use in diagnostic applications. The human MK61 gene has been localized to chromosome band 19q13. More specifically, the gene locates to a region within, or close to, 19q13.1. Several other genes of interest have been localized to this region of chromosome 19, including the human leukocyte receptor cluster (LRC) which has been demonstrated to contain 19 genes encoding leukocyte-expressed receptors of the immunoglobulin (Ig) superfamily, the human Kir2.4 inwardly rectifying potassium channel gene (KCNJ14), the human killer cell inhibitory receptor gene KIR103, the ribosomal protein S19 gene, prostase, and Protease Serine-Like 1. MK61 is a candidate for the diseases and disorders recited herein including Cystinuria, Congenital nephrotic syndrome, Familial nephrotic syndrome, Familial focal segmental glomerulosclerosis, familial Wilms tumor FWT2, B-cell lymphoma-associated hemophagocytic syndrome, Camurati-Engelmann disease, progressive diaphyseal dysplasia, hereditary spastic paraplegia, asthma, heart defects, eye development, systemic lupus erythematosus (hSLE1), primary microcephaly (MCPH2), autosomal recessive spondylocostal dysostosis, cystic fibrosis modifier locus for meconium ileus, acute myelogenous leukemia, B-cell lymphoma associated with haemophagocytic syndrome, multiple myeloma, testicular germ cell tumors, malignant glioma, familial benign hypercalcemithus, the MK61 gene, a probe comprising MK61 DNA or RNA can be used to determine if the MK61 gene is present on chromosome 19, or if a mutation has occurred. Detectable chromosomal aberrations at the MK61 gene locus include, but are not limited to, aneuploidy, gene copy number changes, insertions, deletions, restriction site changes and rearrangements. These aberrations can occur within the coding sequence, within introns, or within flanking sequences, including upstream promoter and regulatory regions, and may be manifested as physical alterations within a coding sequence or changes in gene expression level. Analytical probes will generally be at least 20 nucleotides in length, although somewhat shorter probes (14-17 nucleotides) can be used. PCR primers are at least 5 nucleotides in length, preferably 15 or more nucleotides, more preferably 20-30 nucleotides in length. Short polynucleotides can be used when a small region of the gene is targeted for analysis. For gross analysis of genes, a polynucleotide probe may comprise an entire exon or more. Probes will generally comprise a polynucleotide linked to a signal-generating moiety such as a radionucleotide. In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (c) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, SEQ ID NO:3, SEQ ID NO:5, SEQ ID NO:7, SEQ ID NO:9, SEQ ID NO:11, SEQ ID NO:13, or SEQ ID NO:15, the complement of SEQ ID NO:1, SEQ ID NO:3, SEQ ID NO:5, SEQ ID NO:7, SEQ ID NO:9, SEQ ID NO:11, SEQ ID NO:13, or SEQ ID NO:15, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5-16 (1991)), ribonuclease protection assays, and other genetic linkage analysis techniques known in the art. See Sambrook et al., Id.; Ausubel et. al., Id., and A. J. Marian, *Chest* 108:255-65 (1995). Ribonuclease protection assays (Ausubel et al., Id., ch. 4) comprise the hybridization of an RNA probe to a patient RNA sample, after which the reaction product (RNA-RNA) hybrid) is exposed to RNase. Hybridized regions of the RNA are protected from digestion. Within PCR assays, a patient genetic sample is incubated with a pair of oligonucleotide primers, and the region between the primers is amplified and recovered. Changes in size, amount, or sequence of recovered product are indicative of mutations in the patient. Another PCR-based technique that can be employed is single strand conformational polymorphism (SSCP) analysis. See Hayashi, *PCR Methods and Applications* 1:34-38 (1991).

Assays for MK61 protein in serum may be used to detect the diseases and disorders recited herein. Those skilled in the art will recognize that conditions related to MK61 underexpression or overexpression may be amenable to treatment by therapeutic manipulation of MK61 protein levels.

The MK61 polypeptides may be used (simultaneously or sequentially) in combination with one or more cytokines, growth factors, antibiotics, anti-inflammatories and/or chemotherapeutic agents as is appropriate for the indication being treated.

Other methods may also be employed where it is desirable to inhibit the activity of one or more MK61 polypeptides. Such inhibition may be effected by nucleic acid molecules which are complementary to and which hybridize to expression control sequences (triple helix formation) or to MK61 mRNA. For example, antisense DNA or RNA molecules, which have a sequence that is complementary to at least a portion of the selected MK61 gene(s) can be introduced into the cell. Anti-sense probes may be designed by available techniques using the sequence of MK61 polypeptide disclosed herein. Typically, each such antisense molecule will be complementary to the start site (5' end) of each selected MK61 gene. When the antisense molecule then hybridizes to the corresponding MK61 mRNA, translation of this mRNA is prevented or reduced. Anti-sense inhibitors provide information relating to the decrease or absence of an MK61 polypeptide in a cell or organism.

Alternatively, gene therapy may be employed to create a dominant-negative inhibitor of one or more MK61 polypeptides. In this situation, the DNA encoding a mutant polypeptide of each selected MK61 polypeptide can be prepared and introduced into the cells of a patient using either viral or non-viral methods as described herein. Each such mutant is typically designed to compete with endogenous polypeptide in its biological role.

In addition, an MK61 polypeptide, whether biologically active or not, may be used as an immunogen, that is the polypeptide contains at least one epitope to which antibodies may be raised. Selective binding agents that bind to an MK61 polypeptide (as described herein) may be used for in vivo and in vitro diagnostic purposes, including but not limited to, use in labeled form to detect the presence of MK61 polypeptide in a body fluid or cell sample. The antibodies may also be used to prevent, treat or diagnose a number of diseases and disorders, including those recited herein. The antibodies may bind to an MK61 polypeptide so as to diminish or block at least one activity characteristic of an MK61 polypeptide, or may bind to a polypeptide to increase at least one activity characteristic of an MK61 polypeptide (including by increasing the pharmacokinetics of the MK61 polypeptide).

The following examples are intended for illustration purposes only and should not be construed as limiting the scope of the invention in any way.

EXAMPLE 1

Isolation of Human MK61 cDNA Clones

A TNF receptor family profile search of the Amgen EST database was performed. One human EST sequence (G-0042-B7) was identified as a possible member of the TNF receptor family name as MK61. The full-length human clone was subsequently PCR amplified from a human lymphnode library using the following primers: human MK61 sense primer (5'-GGTGACCACCTCGTGGGCAACGTCT-3'; SEQ ID NO: 21), antisense primer (5'-GCCCAATTAGGAT-TGTACAAGAAG-3; SEQ ID NO: 22) under standard conditions known in the art. Poly (A)+ RNA from the human lymph node was reverse-transcribed, and the cDNAs were synthesized using the Smart RACE cDNA amplification Kit (Clontech, Palo Alto, Calif.) according to the manufacturer's instructions. The full-length cDNA of the human MK61 gene was cloned into the pcDNA3 vector for mammalian cell expression (Invitrogen, Carlsbad, Calif.) and sequenced using standard methods. The name of the clone is pcdna3huMK61#5 and it contains the human MK61 T1 isoform cDNA.

The human MK61 cDNA sequence is 1668 nucleotides (SEQ ID NO: 1) and encodes a 355 amino acid polypeptide (SEQ ID NO: 2). The polypeptide (denoted herein as hMK61T1; see FIG. 1) contains a signal peptide spanning residues 1-23, a cysteine rich domain spanning residues 26-60 that matches the TNFR superfamily cysteine-rich region signature (Madry et al. INTERNATIONAL IMMUNOLOGY. 10:1693-1702, 1998, and references therein), a transmembrane domain spanning residues 157-185, and a long intracellular domain. Careful alignment of all available human MK61 matching cDNA and genomic sequences available in public databases, Amgen internal databases, and the Celera database, identified five additional full length human MK61 isoforms (denoted herein as human MK61T2, MK61T3, MK61T4, MK61T5, and MK61T6).

hMK61T2 polynucleotide sequence is 1525 nucleotides (SEQ ID NO: 3) and encodes a polypeptide of 85 amino acids (SEQ ID NO: 4) containing a signal peptide(residues 1-23) but not a predicted transmembrane domain, suggesting that this isoform may encode a secreted polypeptide (FIG. 2). hMK61T2 contains cysteine rich domain spanning residues 26-51 that exhibit an imperfect match (5 out of 6 cysteine match) to the TNFR superfamily cysteine-rich region signature. hMK61T3 polynucleotide sequence is 1289 nucleotides (SEQ ID NO: 5) and encodes a 136 amino acid residue polypeptide (SEQ ID NO: 6) containing a signal peptide (residues 1-23) but not contain a predicted transmembrane domain, suggesting that this isoform may encode a secreted polypeptide (FIG. 3). hMK61T3 contains a cysteine rich domain spanning residues 26-60 that matches the TNFR superfamily cysteine-rich region signature. hMK61T4 polynucleotide sequence is 1164 nucleotides (SEQ ID NO:7) and encodes a 187 amino acid residues polypeptide (SEQ ID NO: 8) containing a signal peptide (residues 1-23) but not a predicted transmembrane domain, suggesting that this isoform may encode a secreted polypeptide (FIG. 4). hMK61T4 contains cysteine rich domain spanning residues 26-51 that exhibit an imperfect match (5 out of 6 cysteine match) to the TNFR superfamily cysteine-rich region signature. hMK61T5 polynucleotide sequence is 1483 nucleotides (SEQ ID NO: 9) and encodes encodes an 71 amino acid residues polypeptide (SEQ ID NO: 10) with a signal peptide (residues 1-23) but not a predicted transmembrane domain, suggesting that this isoform may encode a secreted polypeptide (FIG. 5). hMK61T5 contains a cysteine rich domain spanning residues 26-57 that matches the TNFR superfamily cysteine-rich region signature but varies slightly from that of hMK61T1. hMK61T6 polynucleotide sequence is 1104 nucleotides (SEQ ID NO: 11) and encodes a 167 amino acid residues polypeptide (SEQ ID NO: 12) containing a signal peptide (residues 1-23) but not a predicted transmembrane domain, suggesting that this isoform may encode a secreted polypeptide (FIG. 6). hMK61T6 contains cysteine rich domain spanning residues 26-51 that exhibit an imperfect match (5 out of 6 cysteine match) to the TNFR superfamily cysteine-rich region signature.

Interestingly all the human MK61 isoforms contain a complete or partial TNFR-type cysteine rich domain which may constitute part of the ligand-binding domain. Hence, while hMK61T1 appears to encode a bona fide novel TNFR family member cell-surface receptor, human isoforms MK61T2-T6 appear to encode secreted receptors. Secreted receptors may function as decoy-receptors which prevent the unknown MK61 ligand from interacting with its receptor as it was previously demonstrated for Osteoprotegerin (OPG).

Osteoprotegerin ligand is a cytokine that regulates osteoclast differentiation and activation. (Lacey et al. *Cell:*93: 165-176, 1998). In addition, the MK61T1-T6 isoforms may bind and regulate reverse signaling through the unknown MK61 ligand.

EXAMPLE 2

Isolation of Murine MK61 cDNA Clone

A TNF receptor family profile search of the Amgen EST database was performed as described above in Example 1. One human EST sequence (G-0042-B7) was identified as a possible member of the TNF receptor family name as MK61. The full-length murine MK61 clone was PCR amplified from a mouse A20 cell library using the following primers: mouse sense primer (5'CGGACGCGTGGGCGGACGCGTGGG-3' SEQ ID NO: 23) antisense primer (5'-AGCAAACTCT-GACTCAGCCAAGTT-3'; SEQ ID NO: 24) under standard conditions known in the art. Poly (A)+ RNA from the mouse B lymphoma cell line A20 was reverse-transcribed, and the cDNA was synthesized using the Smart RACE cDNA amplification Kit (Clontech, Palo Alto, Calif.) according to the manufacturer's instructions. The full-length cDNA of the mouse gene was cloned into the pcDNA3 vector for mammalian cell expression (Invitrogen, Carlsbad, Calif.) and sequenced using standard methods.

The murine MK61 polynucleotide sequence is 1202 nucleotides (SEQ ID NO: 13) and encodes a 345 amino acid polypeptide(SEQ ID NO:14). The murine MK61T1 polypeptide is a cell surface receptor which has a signal sequence spanning residues 1 to 21 and a transmembrane domain (FIG. 7).

EXAMPLE 3

Tissue Distribution of hMK61 mRNA

MK61 mRNA distribution was determined by Northern blot analysis and quantitative PCR. Human peripheral blood T cells, B cells and monocytes were purified by Rosette Sep enrichment cocktail (Stem Cell Technologies) according to the manufacturer's instructuions. Human Burkitt's Lymphoma cells, Raji cells, T lymphoma cells, Jukat cells, K562 cells and U937 cells were obtained from the ATCC (Rockville, Md.). Total RNA was isolated from these cells by the Rneasy Kit (Qiangen, Valencia, Calif.) according to the manufacturer's instructions.

Northern blots analysis was performed using standard conditions known in the art. Multiple tissue Northern blot and multiple tissue cDNAs were purchased from Clontech (Palo Alto, Calif.). The Northern blots were hybridized with random primed human and mouse MK61 radioactive probes for 3 hours at 55° C., and then washed with several changes of 2×SSC/0.1% SDS followed by 0.1×SSC/0.1% SDS for 30 minutes.

Figure 13:
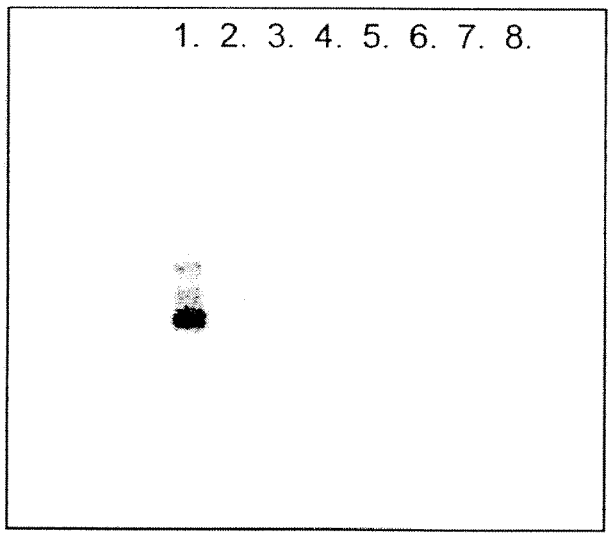
FIGS. 13 and 14 depict multiple tissue Northern blots which were probed with a random primed human MK61 radioactive probe. These blots demonstrate that human MK61 mRNA is expressed in human lymphoid tissues.
Figure 14:
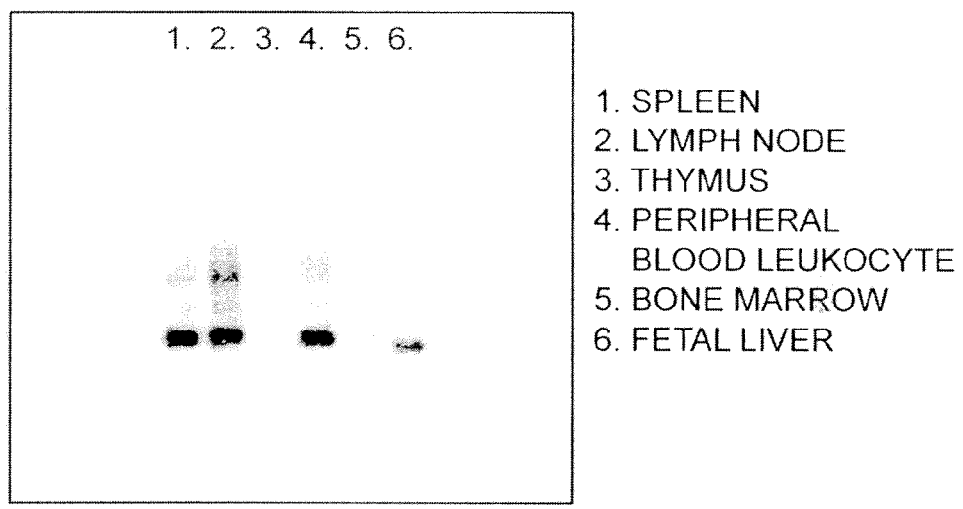

The Northern blot analysis demonstrated that hMK61 was predominantly expressed in peripheral lymphoid organs, spleen, lymph nodes, thymus, bone marrow, in peripheral blood leukocytes, as well as in fetal liver. (See FIGS. 13 and 14) Several different MK61 isoforms were expressed in those organs but the major transcript was 1.6 kbp.

Figure 15:
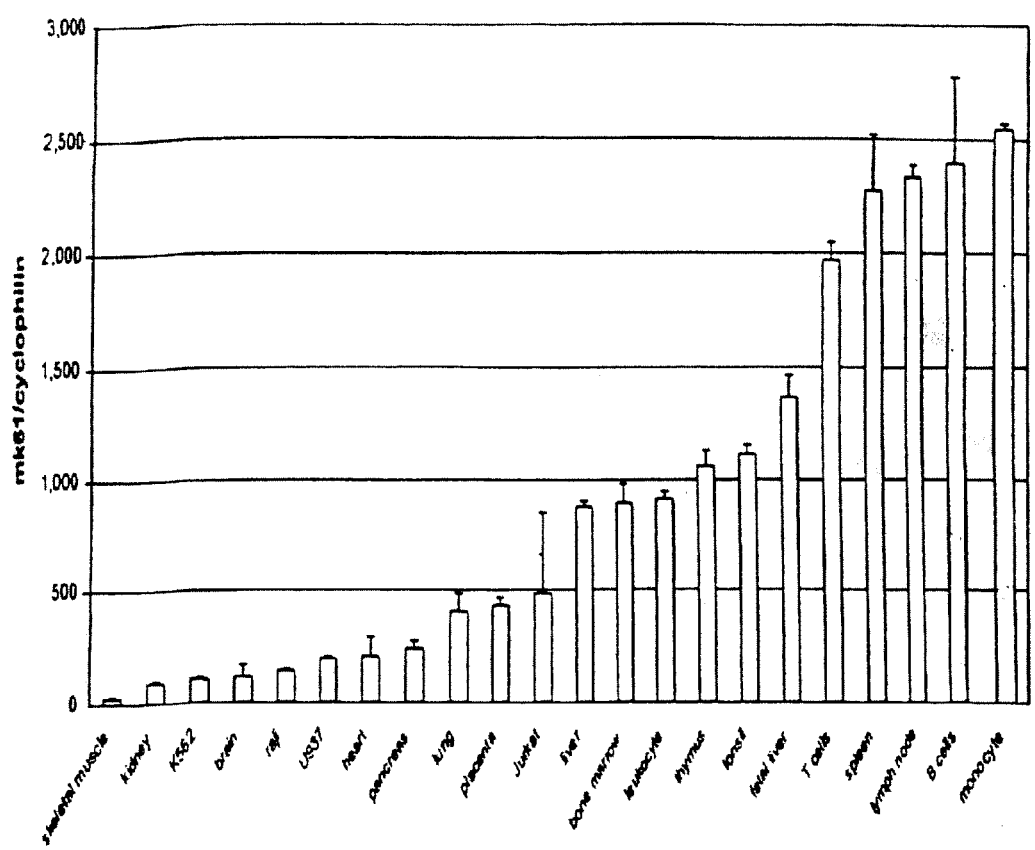
FIG. 15 depicts a histogram comparing human MK61 mRNA expression in various human tissues and cell lines as measured by quantitative PCR.
Figure 16A:
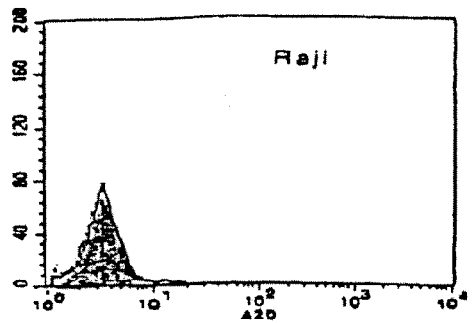
FIG. 16 depicts histograms quantitating the binding of the MK61-Fc fusion protein on the surface of human cells as measured by FACS analysis. The histograms indicate that MK61-Fc fusion protein binds to the cell surface of U937 and Jurkat cells.
Figure 16D:
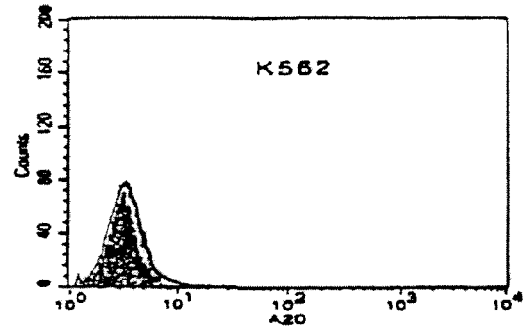
Figure 16B:
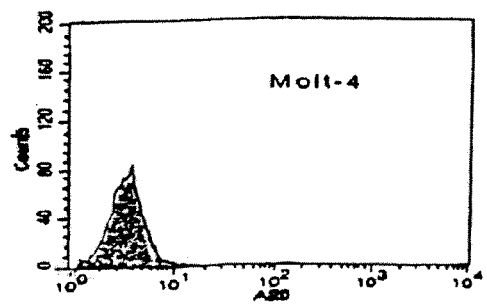
Figure 16E:
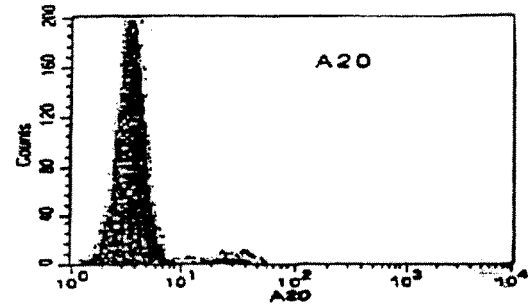
Figure 16C:
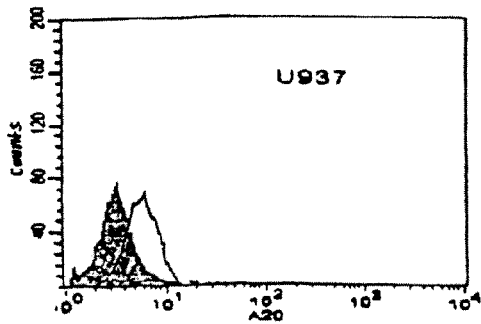
Figure 16F:
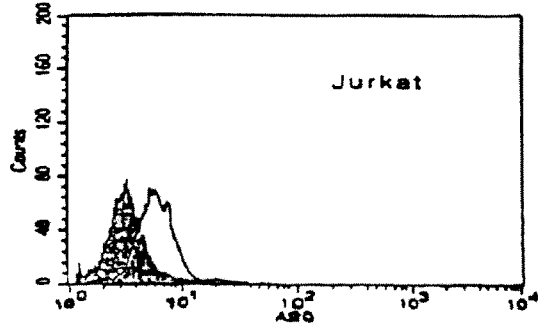

Real-time quantitative PCR was carried out on various human tissues and cell lines. This assay uses a fluorogenic probe and PCR primers to enable the detection of a specific PCR product. The PCR primers and the probe were designed using PE Biosystems' Primer Express software and were synthesized by Amgen Boulder as requested. Oligonucleotide primers specific and probes for human MK61 (Probe #2288-23 ETT CCC AGT TTT TCA TCT GCA CTG CCA X (SEQ ID NO: 40);5' primer #2288-22 TGC TGG ACC CAA CAC AAA TG (SEQ ID NO: 41); 3' primer #2288-24 TGC CAT CCA ACC ACT CAG TC (SEQ ID NO: 42))and human cyclophilin (Probe #2661-92 ECT GCC TGC TGC CTG GTC CAC CTX (SEQ ID NO: 43), 5' primer #2661-90 ACA CCT GGC CGC AAG ATA TG (SEQ ID NO: 44); 3' primer: #2661-91 GAC TCG GCC TCA GCG AAT AG (SEQ ID NO: 45)) were used as primers for Taqman Following the PE Biosystems' standard protocol, the Taqman PCR reactions were performed on ABI PRISM 7700 instrument and the data were analyzed by PE Biosystems's Sequence Detection System software (See FIG. 15)

Human MK61 mRNA expression was the greatest in monozytic cells, B cells, lymph nodes, spleen and T cells. Intermediate levels of human MK61 mRNA expression were detected in liver, bone marrow, thymus, tonsil, and fetal liver. Low levels of human MK61 mRNA were detected in lung, placenta and Jurkat cells. Interestingly, the expression of human MK61 mRNA was higher in primary B cells, T cells and monozytic cells than in the corresponding tumor cells lines Raji, K562 and U937. This expression pattern would be consistent with the notion that MK61 expression is lymphoid-specific and may be downregulated in tumor cells.

EXAMPLE 4

Preparation of the mMK61-Fc Fusion Construct

The predicted 175 amino acid extracellular portion of Smil2-00051-f3 was subcloned into the PEFBOS vector (pEF-BOS; a powerful mammalian expression vector; Mizushima et al. Nuc. Acids Res. 18: 5322, 1990), and an Fc portion was attached at the end of the gene. The nucleotide sequence encoding the mMK61-Fc is set out as SEQ ID NO: 15. Transfection was performed using Bio-Rad Cytofectene as a transfection reagent. The condition medium was collected 48 hours after the transfection, and CM was 10× concentrated by Centricon 10 columns (Millipore Corp., Bedford, Mass.). The samples loaded in lanes 6, 7, and 8 were the concentrated conditioned media (See FIG. 9).

The mMK61 Fc fusion protein (SEQ ID NO: 16) was detected by an anti-human IgG(Fc) (Pierce), at a dilution of 1:3000, and then visualized by enhanced chemical luminescence (ECL). The exposure time was 15 seconds. 2933 cell lysate was used as a positive control and was prepared as follows: 293 cells (available under ATCC Accession Number CRL-1573) were suspended in 200 μl 2×SDS loading buffer, and were heated. The cell lysates (5 μl) was then loaded into each lane. The Western blot (FIG. 9) indicates that the MK61-Fc fusion protein was secreted and is detectable in the cellular conditioned media.

EXAMPLE 5

Production and Purification of Recombinant MK61-Fc Fusion Proteins

A. Cloning and Bacterial Expression of Human MK61-Fc protein:

PCR amplification employing the primer pairs and templates described below were used to generate various forms of human MK61 proteins. One primer of each pair introduced a stop codon (TAA). and a unique XhoI site following the carboxy terminus of the gene. The other primer of each pair introduced a unique NdeI site, an N-terminal methionine, and optimized codons for the amino terminal portion of the gene. PCR and thermocycling were performed using standard recombinant DNA methodology. The PCR products were purified, restriction digested, and inserted into the unique NdeI and XhoI sites of vector pAMG21 (ATCC accession no. 98113). Subsequently, prototrophic E. coli strains 393 or 2596 were transformed with the vector. Other commonly used E. coli expression vectors and host cells are also suitable for expression. After transformation, the clones were selected, plasmid DNA was isolated and the sequence of the MK61 protein insert were confirmed.

1. pAMG21-Human MK61 21-160 His:

The pAMG21-h MK61 21-160 His construct was engineered to be 147 amino acids in length and have the following N-terminal and C-terminal residues: $NH_2$-Met-Glu-Ala-Ser-Gln - - - Gln-Ala-Trp-Pro-Asn-His-His-His-His-His-His-COOH (SEQ ID NO: 25). The following oligonucleotides primer pair (#2609-87 and #2609-88) was used for PCR and cloning this gene construct (2609-87: 5'-GAG GAA TAA CAT ATG GAA GCC TCT CAG TAT TGC GGC CGC-3' (SEQ ID NO: 26); 2609-88: 5'-CGG CCG ATC CTC GAG

TTA ATG ATG ATG ATG ATG ATT CGG CCA GGC CTG CTG-3'(SEQ ID NO: 27)).

2. pAMG21-Human MK61 21-160 Fc (Human IgG1)

The pAMG21-human MK61 21-160 Fc construct was engineered to be 373 amino acids in length and have the following N-terminal and C-terminal residues: $NH_2$-Met-Glu-Ala-Ser-Gln - - - Ser-Pro-Gly-Lys-COOH (SEQ ID NO: 28). A linker composed of five glycine residues was inserted between the C-terminus of the MK61 protein and the N-terminus of human IgG1 Fc. The sequence of the MK61-Fc junction was as follows: Gln-Ala-Trp-Pro-Asn-Gly-Gly-Gly-Gly-Gly-Asp-Lys-Thr-His (SEQ ID NO: 29). PCR amplification of this construct was performed in two steps. In the fist step, the MK61 and Fc portions of the gene were amplified. Oligos #2609-87 (5'-GAG GAA TAA CAT ATG GAA GCC TCT CAG TAT TGC GGC CGC-3' SEQ ID NO: 30); and #2609-97 (5'-ACA TGT GTG AGT TTT GTC ACC ACC ACC ACC ACC ATT CGG CCA GGC CTG CTG-3'SEQ ID NO: 31) were used to amplify the MK61 portion. Oligos #2609-98 (5'-CAG CAG GCC TGG CCG AAT GGT GGT GGT GGT GGT GAC AAA ACT CAC ACA TGT-3' SEQ IS NO: 32) and #2293-10 (5'-CCG CGG ATC CTC GAG TTA TTT ACC CGG AGA CAG GGA GAG-3' SEQ ID NO: 33) were used to amplify the human IgG1 fc portion. In the second step, the reaction products from the first amplification were gel purified and used as templates to create the final MK61::fc construct. Oligos #2609-87 (SEQ ID NO: 30) and #2293-10 (SEQ ID NO: 33) were used for PCR amplification of this construct.

After confirmation of the DNA sequence, the transformed *E. coli* were grown at 37° C. to mid-log phase and treated with homoserine lactone (HSL) at a final concentration of 250 ng/ml to induce expression of MK61-Fc fusion protein. Following induction, the cells were grown at 37° C. for several hours and subsequently harvested by centrifugation and frozen at –80° C. Growth of the transfected *E. coli*, induction of MK61-Fc protein expression and isolation of inclusion bodies containing MK61-Fc was carried out according to procedures described in U.S. patent application Ser. No. 08/577, 788 filed Dec. 22, 1995 incorporated herein by reference.

Purification and refolding of the MK61-Fc fusion protein expressed in *E. coli* was accomplished using the following methods. To solubilize the MK61-Fc fusion protein, the bacterial cells were broken in a microfluidizer and centrifuged at 12,000 g for 1 hour. The resulting inclusion bodies were washed with water and centrifuged at 12,000 g for 1 hour. The pellet was then solubilized for 1 hour in 50 mM Tris, 8 M GuHCl and 7 mM DTT (pH 8.5) and centrifuged at 12,000 g for 1 hour.

To refold the MK61-Fc fusion protein, the supernanant was diluted 1:20 with 50 mM Tris, 2 M Urea, 0.2 M arginine (pH 8.5) and incubated at 4° C. until the Elman test was negative for free thiol (approximately 4 days). The supernatant was then concentrated 20 fold and diafiltered with 4 volumes of 50 mM Tris (pH 8.5). The diluted supernatant was acid precipitated by diluting the solution 10 fold with 25 mM Tris (pH 8.5) and lowering the pH to 5.0. The diluted solution was then stirred for 5 minutes and centrifuged at 12,000 g for 30 minutes.

For purification, the supernatant was loaded onto a SP high performance column and run on a 0-600 mM NaCL gradient in the presence of NaOAc (pH 5.0) over 60 column volumes. The fusion protein eluted at around 500 mM NaCl. Pooled fractions were titrated to pH 7.0, brought up to a concentration of 1M in ammonium sulfate (AS) and centrifuged at 12,000 g for 30 minutes. The supernatant was then loaded onto a butyl high performance column and run on a gradient of 1M AS to 0M AS in the presence of 10 mM NaPi (pH 7.0) over 50 column volumes. The fusion protein eluted approximately at 30 mM AS. The pooled fractions were diafiltered into PBS.

B. Cloning, Expression and Purification of MK61-Fc in Mammalian Cell Culture:

A cDNA fragment encoding human MK61-Fc amino acids 1 to 153 was amplified by PCR using the pcdna3huMK61#5 as a template and the primers #2623-81 (CAG CCC AAG CTT TAG ACC ACC ATG GGG CCT GGA CGA TGC; SEQ ID NO: 34) and 2623-83 (CAG GTC GAC AGG CTC AGG GGT CCT; SEQ ID NO: 35). These primers inserted HindIII and Sal1 sites at the 5' and 3' end of the gene respectively. PCR product were purified, digested with HindIII and Sal1 and ligated into huOPG194 Fc delta C vector, 9described in WO 01/18203 and in EP1127117), digested with HindIII and Sal1 and dephosphorylated. The products of the ligation were transformed into DH5α competent cells (Invitrogen, Carlsbad, Calif.) and plated onto LB+ ampicillin plates.

Eight colonies of the transformed DHα competent cells were grown to isolate DNA using the mini-prep technique (Qiagen) The isolated DNA was screened by digestion with Not1 and Pvu1. Five of the clones generated a 1512 base pair fragment as expected. Clones 1 and 7 of the positive clones were amplified in 500 ml preparations, the DNA isolated and sequenced using standard methods.

The DNA isolated from clone 7 was the correct sequence. The amino acid sequence of MK61-Fc is shown in FIG. 24 as SEQ ID NO: 36. Clone 7 DNA (15 μg) was linearized with Pvu1 and transfected into AM-1/D cells. AM-1/D are Chinese Hamster Ovary cells devoid of DHFR (Urlaub and Chasin 1980 PNAS vol 77 4216-4220) adapted to serum free conditions (described in U.S. Pat. NO. 6,210,924). Stable clones were generated based on the selection marker DHFR (dihydrofolate reductase). Nine stable clones were expanded for expression analysis. Expression of MK61-Fc was determined by Western-blotting, using anti-human IgG1 Fc antibodies (Pierce). A high-expressing clone was selected and expanded by growing the cells in roller bottles using standard methods.

To purify human MK61-Fc fusion protein, conditioned CHO-MK61-Fc media was loaded onto a protein G column equilibrated in PBS. The column was washed with 20 column volumes of PBS and the fusion protein was eluted with 100 mM Glycine (pH 2.6), and the pooled fractions were neutralized with 1 M Tris (pH 8.5) and diafiltered into PBS.

C. Production of Murine Mk61/Fc Delta C Fusion Protein:

The murine MK61 cDNA encoding the extracellular domain of the protein was amplifed from the full-length muMK61 cDNA (SEQ ID NO: 13) using primers #2664-83 (CAG CCC AAG CTT TAG ACC ACC ATG GGG CCC AGC TGG CTT; SEQ ID NO: 37) and #2664-84 (CAG GTC GAC CTC ATT CTT GGT TGT; SEQ ID NO: 38). These primers inserted HindIII and Sal1 sites at the 5' and 3' end of the gene respectively. The PCR product was purified, digested with HindIII and Sal1 and ligated into huOPG194 Fc delta C vector digested with HindIII and Sal1 and dephosphorylated. The ligation product was transformed into DH5α competent cells and plated onto LB+ ampicillian plates.

Sixteen colonies of transformed DHα competent cells were grown to isolate their DNA by the mini-prep technique. The isolated DNA was screened by digestion with MSC1 (unique enzyme for MK61) and Pvu1 (unique enzyme for pDSRα vectors). Fifteen of the clones generated a 1523 base pair fragment as expected. Clones 2 and 4 of these positive clones were amplified in 500 ml preps; DNA isolated and sequenced using standard methods.

The DNA isolated from both clones 2 and 4 had the correct sequence for expression of MK61-Fc fusion protein (FIG. 25; SEQ ID NO: 39). Clone 2 DNA (15 µg) was linearized with Pvul and transfected in to AM-1/D cells which are derived from the Chinese Hamster Ovary (CHO) cell-line. Stable clones were generated based on the selection marker DHFR. Nine clones were expanded for expression analysis. Expression of MK61-Fc was determined by Western-blotting, using anti-human Fc antibodies.

EXAMPLE 6

MK61-Fc Binding as Determined by FACS Analysis

Binding of the MK61-Fc proteins was detected on human cells by florescent activated cell sorting (FACS). Raji, Molt-4, U937, K562, A20 and Jurkat cells were obtained from the ATCC. The cells were collected and incubated at room temperature with 1 µg/ml of human MK61-Fc in binding buffer (DMEM medium containing 10 mM HEPES buffer, 2% goat serum, 5% rabbit serum, 1 µg/ml anti-mouse CD16/CD32 monclonal antibody (PharMingen, San Diego, Calif.)) for 30 minutes followed by 3 washes with PBS containing 2% FBS. Binding of the MK61-Fc fusion proteins to the cell surface was assessed by immunofluorescent staining using FITC conjugated anti-human IgG Fc secondary antibody (PharMingen, San Diego, Calif.). Fluorescence was detected using a FACStar (Becton and Dickinson, Mountain View, Calif.).

Figure 17A:
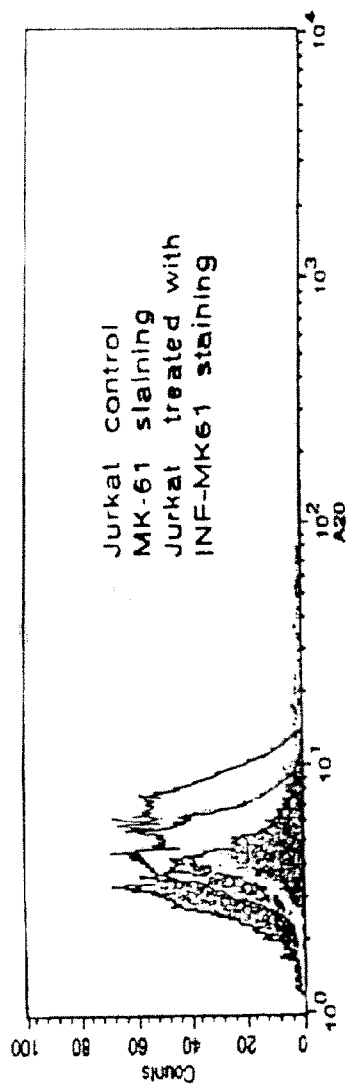
FIG. 17 displays histograms demonstrating enhanced binding of the MK61-Fc fusion protein on the cell surface of Jurkat and U937 cells after treatment with interferon gamma.
Figure 17B:
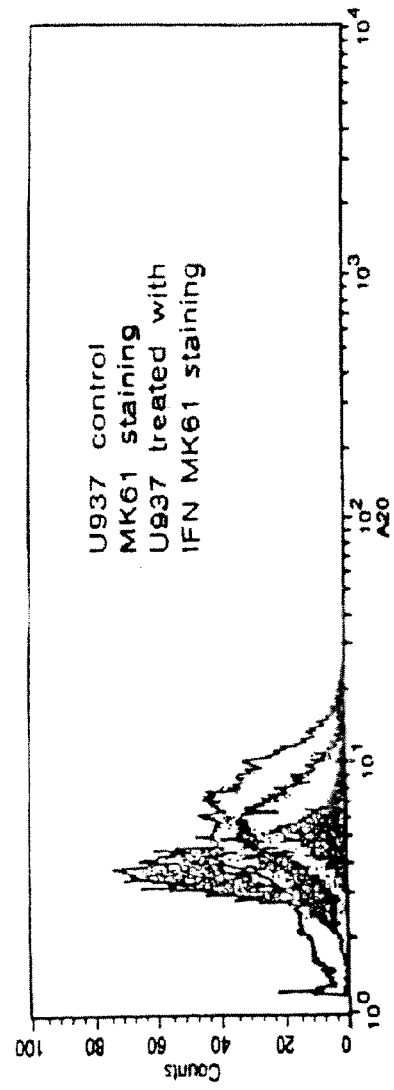

MK61-Fc binding was detected on U937 and Jurkat cells. (See FIG. 16) To enhance the MK61-Fc binding, U937 and Jurkat cells were treated with human interferon gamma (10 ng/ml) for 24 hours prior to analysis. The pre-treatment with interferon gamma enhanced MK61-Fc binding. (See FIG. 17) The binding of MK61-Fc fusion protein to these cells indicates that the MK61 ligand exists on the cell surface of monozytic (U937) and T cells (Jurkat).

The existence of the unknown MK61 ligand on the surface of immune cells suggests that ligand binding soluble forms of MK61 (such as MK61-Fc fusion protein) may act as "positive reagents" which activate the MK61 receptor signaling pathway. This may be accomplished by the positive reagents binding to the yet unknown MK61 ligand(s) located on the surface of the immune cells and thereby triggering reverse signaling through the ligand. Such signaling would be the immune system regulating event resulting in lymphocyte expansion and immunoglobulin production

EXAMPLE 7

MK61-Fc Inhibited Immunoglobulin Production in Primary Splenocytes

Total spleen cells were isolated from mice spleens using lymphocyte separation medium (ICN, Aurora, Ohio) centrifugation. Splenocytes were cultured in vitro with 150 ng/ml lipo-poly-saccraride (LPS) for 72-96 hours in the presence of mouse or human delta C MK61-Fc delta fusion protein. Subsequently, the culture supernatants from the treated cells were removed after 4 days to analyze the production of various Ig isotypes. (PharMingen, Ca).

Figure 18A:
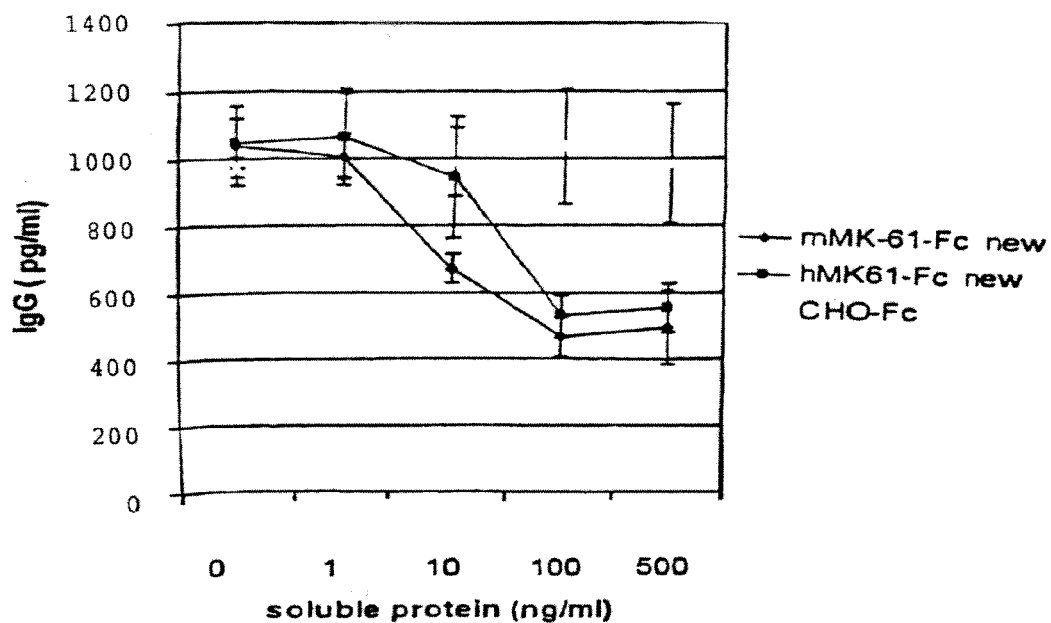
FIG. 18 depicts histograms quantitating the production of IgG (top panel) and IgA (bottom panel) in mouse splenocyte cultures after treatment with MK61-Fc fusion protein.
Figure 18B:
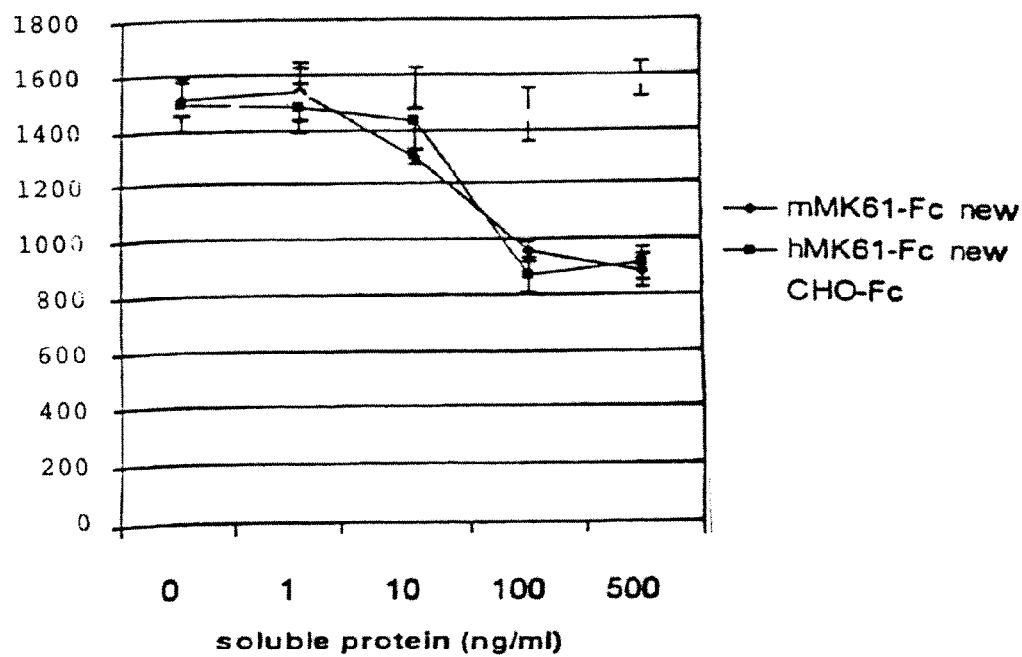

Treatment with both murine and human MK61-Fc fusion proteins caused a dose-dependent decrease in IgA and IgG production in the mouse spleenocyte cultures (See FIG. 18). Maximum inhibition was achieved when MK61-Fc was used at a concentration of 100 ng/ml. This data indicates that MK61-Fc fusion protein is a potent inhibitor of the immune system. This data also suggests that the MK61 receptor activates the immune system signaling pathway that may be antagonized by "negatives regulators" such as the soluble MK61-Fc fusion protein.

To determine if the MK61-Fc fusion protein-induced inhibition of immunoglobulin production was due to inhibition of B cell proliferation, the effect of MK61-Fc on B cell proliferation was measured. Mouse B cells were purified by negative selection from spleens of C57Bl/6 mice using a mouse B cell recovery column (Cedarlane, Hornby, Ontario, Canada). The cells isolated by this method were more than 90% positive for B220 staining as determined by FACS analysis. 1×10$^6$/ml were seeded in 96 well flat bottom tissue culture plates in medium (RPMI-1640, 5% FBS, 5×10$^{-5}$M 2ME, 2 µg/ml of affinity-purified goat F (ab')$_2$ anti-mouse IgM). The B cells were then incubated with 100 ng/ml human or mouse MK61-Fc protein in the presence or absence of increasing amounts of CD40L, APRIL or TALL-1 for 72 hours. DNA synthesis was quantitated by measuring the incorporation of [$^3$H ]thymidine. 0.5 µCi of [$^3$H ]thymidine was added 18 hours prior to harvesting the cells and counting the incorporation of [$^3$H] thymidine. Treatment with MK61-Fc fusion proteins did not effect B cell proliferation in this assay.

EXAMPLE 8

Effect of MK61-Fc Fusion Protein Treatment on B Cell Responses In Vivo

To characterize the functional significance of the MK61 polypeptide, the fusion protein MK61-Fc delta C used to treat mice.

Initially, Balb/c mice (females of 8-12 weeks of age, Charles River Laboratories) were treated interperitoneally with 5 mg/Kg of MK61-Fc once a day for seven consecutive days starting on day 0. Control mice were treated with 5 mg/Kg of IgG1 Fc or saline as above. Mice were sacrificed one day following the last injection of MK61-Fc, i.e., on day 7. The spleens were dissected for histological examination, FACS analysis and for serum Ig measurements.

Figure 19A:
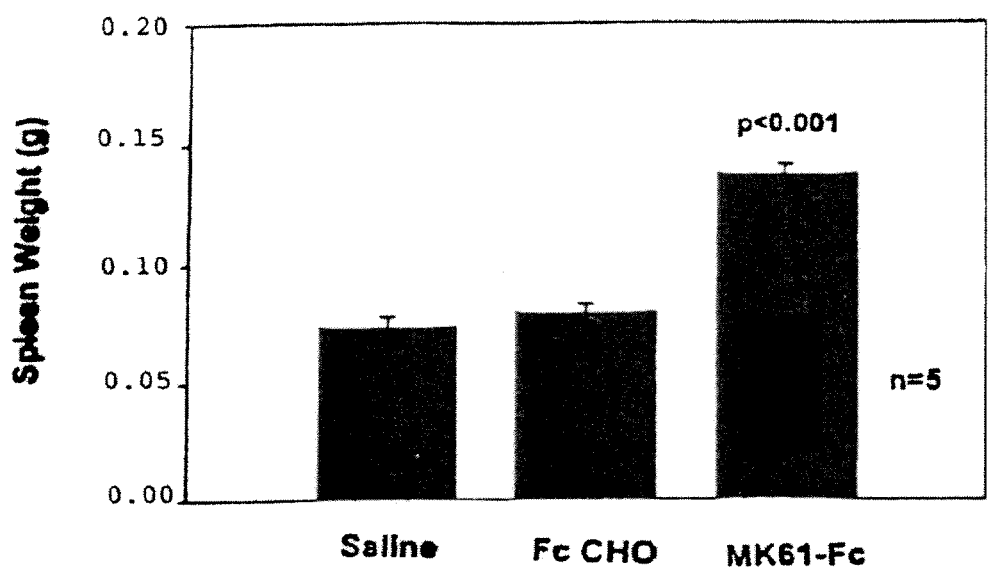
FIG. 19 depicts histograms quantitating the effect of MK61-Fc fusion protein on spleen weights in mice (top panel) and spleen lymphocytes (bottom panel). These histograms demonstrate that treatment with the MK61-Fc fusion protein increased the spleen weight and the number of spleen lyphocytes.
Figure 19B:
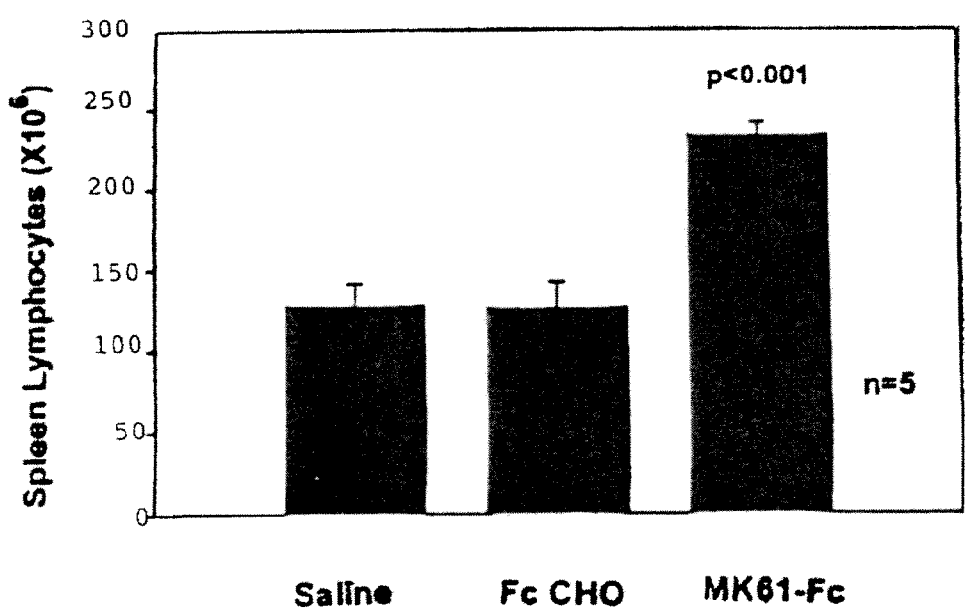

A. Histological Analysis:

For histological examination, spleens were fixed in formalin, embedded in paraffin following standard procedures, and stained with hematoxylin and eosin. Treatment with MK61-Fc fusion protein increased spleen weight by 75% compared to control Fc protein or saline (FIG. 19, top panel). The spleen weight increase reflects a comparable increase in the number of spleen lymphocytes (FIG. 19, bottom panel). The total number of lymphocytes was determined using a Technicon H.I.E. Counter (Bayer Co. Diagnostic Division, Northwood, Md.) following the standard procedure recommended by the manufacturer. The histological examination of the spleens from the MK61-Fc-treated mice indicated the presence of lymphoid hyperplasia, characterized by (1) increased numbers of moderately- to well-developed follicular germinal centers as well as (2) increased numbers of plasma cells that were usually located in focal accumulations at the interface between the white and red pulp (See FIG. 20). Lymphoid hyperplasia was not observed in Fc-protein or saline-treated control mice.

B. FACS Analysis

Figure 21A:
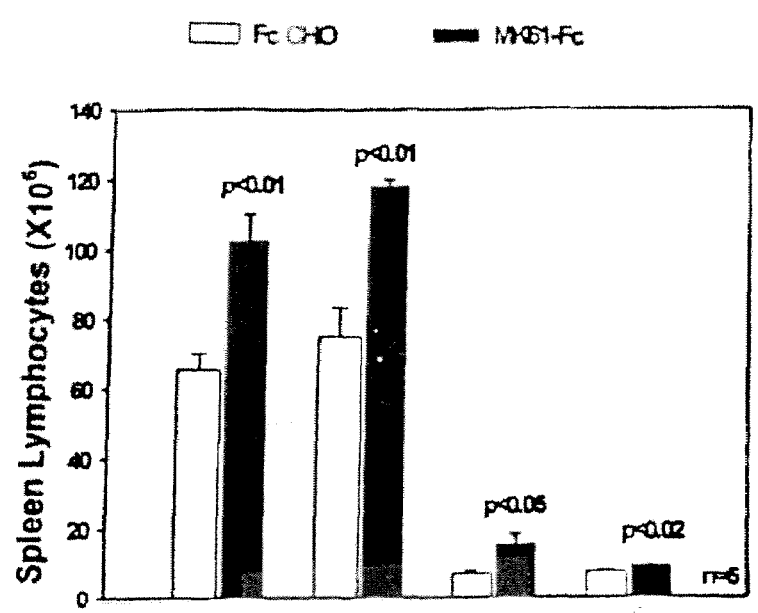
FIG. 21 depicts histograms quantitating the numbers of spleen B and T cells in mice treated with MK61-Fc fusion protein.
Figure 21B:
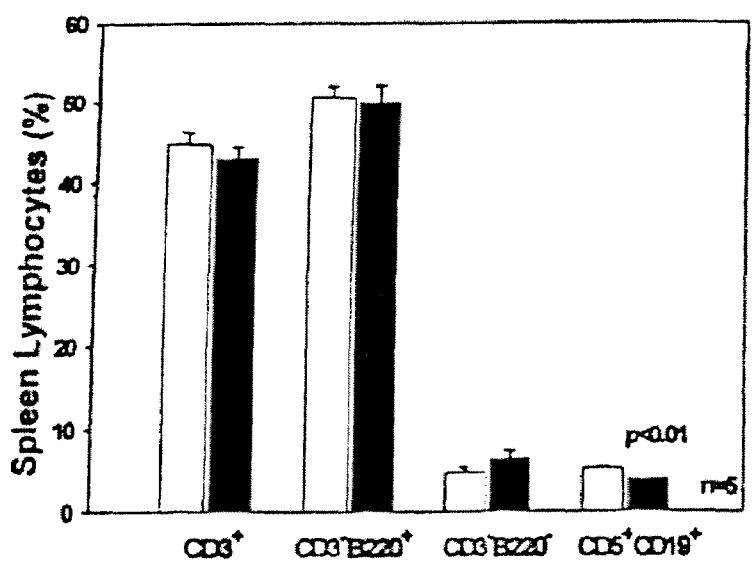

For FACS analysis, spleens were collected in saline and homogenized to yield a cell suspension. The total lymphocyte number was obtained with a cell counter, while lymphocyte subset percentages were derived by immunofluorescence double staining and flow cytometry. MK61-Fc fusion protein increased the total number of spleen lymphocytes compared to control Fc or saline by 90% (FIG. 21 top panel). MK61-Fc proportionally increased T, B, and non-T non-B cells. In fact, MK-61-Fc increased the absolute numbers of CD3+ (T cells), CD3−/B220+ (B cells), and CD3−/B220− (non-T and non-B cells) cells but did not significantly affect the percentages of these cells (FIG. 21 bottom panel). MK61-Fc modified the proportions of B cell subsets. In fact, MK61-Fc decreased the percentage of CD19+/CD5+ (B) cells but still increased their absolute number (FIG. 21).

Figure 22:
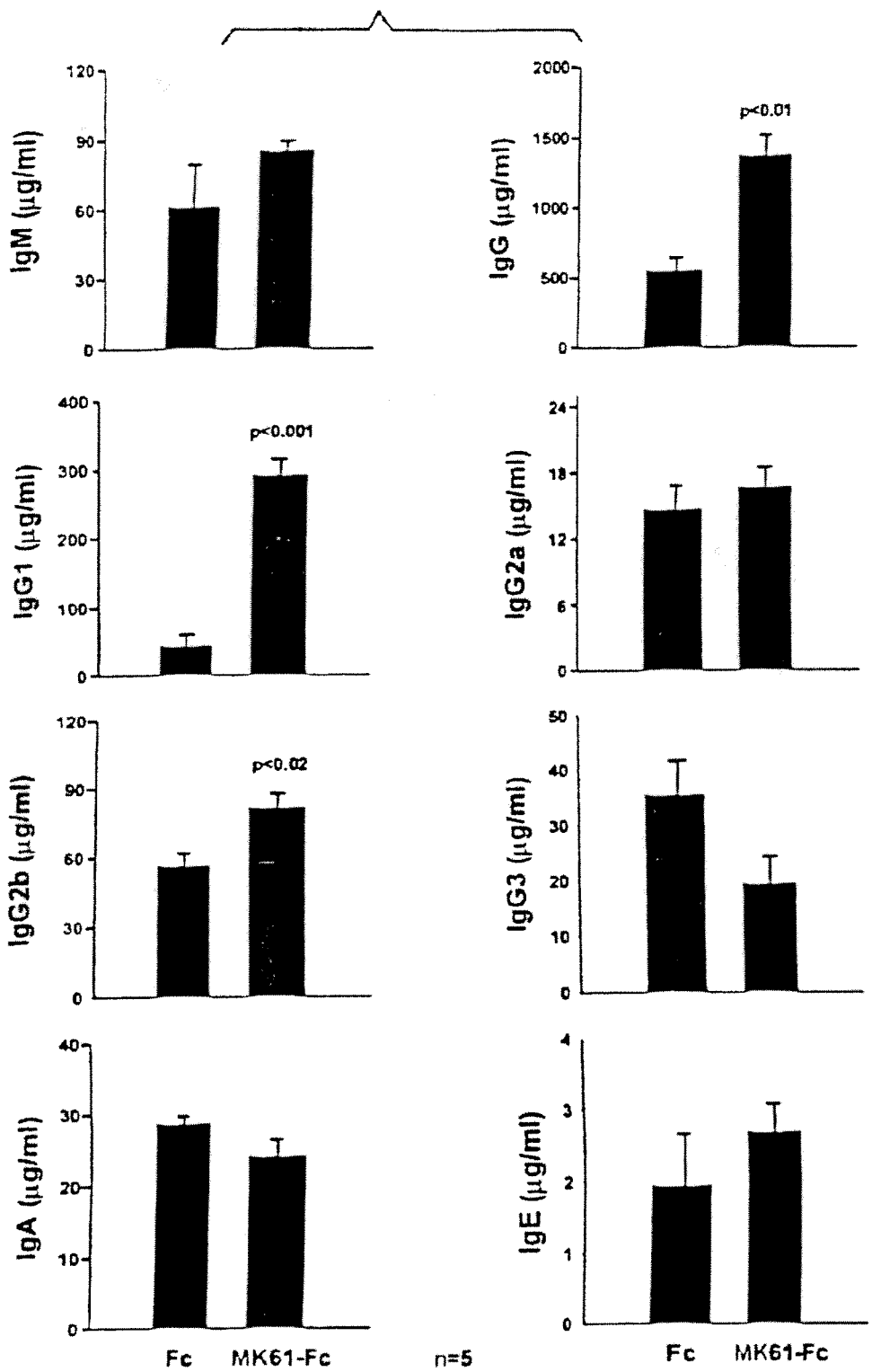
FIG. 22 depicts histograms quantitating plasma immunoglobulin levels in mice treated with MK61-Fc fusion protein.

C. Serum Immunoglobin Measurements:

Serum immunoglobins were measured by sandwich ELISA as previously described (Guo et al. J. Immunol. 166: 5578-84, 2001). Compared to control Fc, MK61-Fc increased the serum concentrations of total IgG, IgG1, and IgG2b but did not significantly modify the concentrations of other Ig types and subtypes (FIG. 22). The increase in IgG1 was the most pronounced if all IgG subtypes (by about 6 fold).

EXAMPLE 9

Additional Effects of MK61-Fc Fusion Protein Treatment on T Cell Response In Vivo In another in vivo experiment, mice were immunized on day 0, prior to the first injection of murine MK61-Fc fusion protein or FC-protein control, with the T cell independent antigen Pneumovax (115 µg, Merck, West Point, Pa.) or the T cell dependent antigen keyhole limpet hemocyanin (KLH, Pierce, Rockford, Ill.) in complete Freund's adjuvant (CFA). Following the pre-treatment, the animals were treated as described above in Example 7. The mice were bled on days 7 and 14 to obtain serum to measure antigen-specific antibodies.

Figure 23:
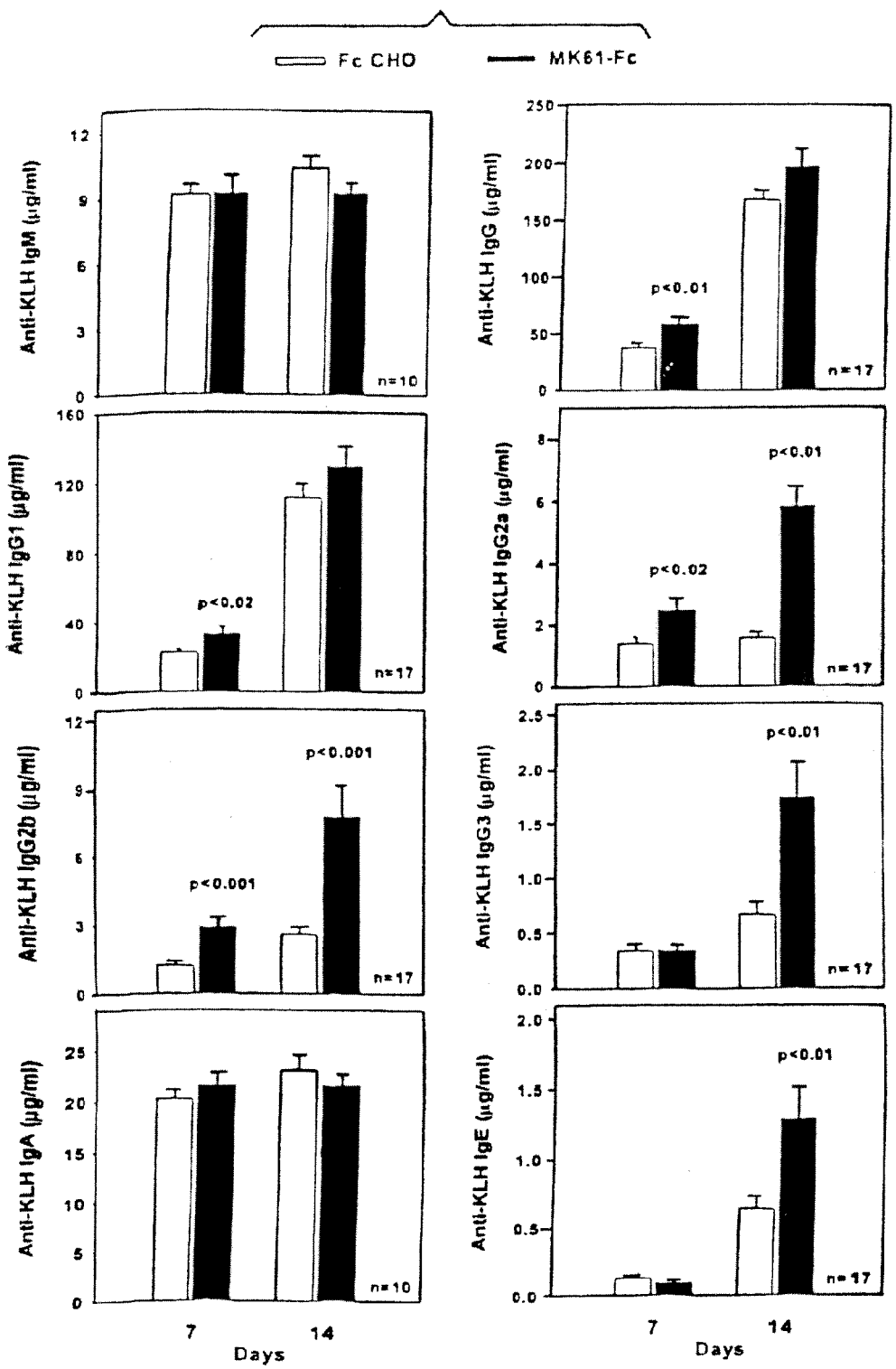
FIG. 23 depicts histograms quantitating the generation of anti-KLH specific antibodies in mice treated with MK61-Fc fusion protein.

Anti-KLH and anti-Pneumovax IgG and IgM were measured in serum by ELISA as previously described (Yu et al. Nature Immunol. 1: 252-256, 2000) Briefly, for the measurement of anti-KLH, plates were coated with KLH in PBS, blocked, and various dilutions of standard and test samples were added. Captured anti-KLH IgG or IgM were revealed using anti-IgG or anti-IgM biotinylated antibodies and neutravidin-conjugated HRP (horse-radish peroxidase). For the measurement of anti-Pneumovax IgM, plates were coated with Pneumovax using poly-L-lysine, blocked, and various dilutions of standard and test samples were added. Captured anti-Pneumovax IgM were revealed using an anti-IgM biotinylated antibody and neutravidin-conjugated HRP Compared to control Fc-protein, MK61-Fc fusion protein did not change the serum concentration of anti-Pneumovax antibodies (IgM; data not shown); but changed that of anti-KLH antibodies of certain Ig classes and subclasses (See FIG. 23). On days 7 and/or 14 of immunization, MK61-Fc fusion protein increased the serum concentrations of anti-KLH IgG, total and of all subclasses, and anti-IgE (FIG. 23).

The in vivo studies in Example 8 and 9 show that MK61 polypeptide regulates immunity, with particular reference to adaptive immunity. The disruption of the interaction between MK61 and its as yet unknown ligand(s) using a putatively ligand binding soluble form of the molecule (MK61-Fc fusion protein) results in lymphocyte expansion and Ig production. This indicates that disrupting this interaction using "negative reagents" (such as MK61-Fc fusion protein, similar MK61-derived molecules or antagonistic antibodies directed against MK61 or its ligand(s)) may lead to immunostimulation. While, artificially creating this interaction using "positive reagents" (such as MK61 binding soluble forms of MK61 ligand(s), agonistic antibodies to MK61 or other molecules which activate the MK61 receptor) may lead to immunosuppression.

What is claimed is:

1. An antibody or fragment thereof that specifically binds an MK61 polypeptide produced by immunizing an animal with a polypeptide comprising the amino acid sequence selected from the group consisting of SEQ ID NO: 2, SEQ ID NO: 8, and SEQ ID NO: 12.

2. An antibody or fragment thereof that specifically binds to a polypeptide comprising the amino acid sequence selected from the group consisting of SEQ ID NO: 2, SEQ ID NO: 8, and SEQ ID NO: 12, wherein the antibody or fragment thereof binds to said amino acid sequence.

3. An antibody or fragment thereof that specifically binds to a polypeptide encoded by a nucleic acid sequence selected from the group consisting of:
   (a) a nucleotide sequence set forth in SEQ ID NO: 1; and
   (b) a nucleotide sequence encoding the polypeptide as set forth in SEQ ID NO: 2.

4. The antibody of any one of claims 1-3 that is a human antibody or a fragment thereof.

5. The antibody of any one of claims 1-3 that is a humanized antibody or a fragment thereof.

6. The antibody of any one of claims 1-3 that is a polyclonal antibody or a fragment thereof.

7. The antibody of any one of claims 1-3 that is a monoclonal antibody or a fragment thereof.

8. A hybridoma that produces the monoclonal antibody or the fragment thereof of claim 7.

9. The antibody of any one of claims 1-3 which is a chemically modified deriative.

10. The derivative of claim 9 which is covalently modified with a water-soluble polymer.

11. The derivative of claim 10 wherein the water-soluble polymer is selected from the group consisting of polyethylene glycol, monomethoxy-polyethylene glycol, dextran, cellulose, poly-(N-vinyl pyrrolidone) polyethylene glycol, propylene glycol homopolymers, polypropylene oxide/ethylene oxide co-polymers, polyoxyethylated polyols, and polyvinyl alcohol.

12. The antibody of any one of claims 1-3, which is a Fab antibody.

13. The antibody of any one of claims 1-3, which is a Fab' antibody.

14. The antibody of any one of claims 1-3 comprising a detectable label.

15. A composition comprising the antibody of any one of claims 1-3 and a pharmaceutically acceptable formulation agent.

* * * * *

UNITED STATES PATENT AND TRADEMARK OFFICE
CERTIFICATE OF CORRECTION

PATENT NO. : 7,569,387 B2
APPLICATION NO. : 11/436207
DATED : August 4, 2009
INVENTOR(S) : Theill et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 277 days.

Signed and Sealed this

Seventh Day of September, 2010

David J. Kappos
*Director of the United States Patent and Trademark Office*

SEQUENCE LISTING

<160> NUMBER OF SEQ ID NOS: 45

<210> SEQ ID NO 1
<211> LENGTH: 1668
<212> TYPE: DNA
<213> ORGANISM: Homo sapiens

<400> SEQUENCE: 1

```
gtaaagatgg ggtttcattt tgttgtccag gctgatctct cgaactcctg ggctcaagtg      60
atcctcctgt cttggcctcc caaagtgttg ggattacagg catgagccac cacacccagc     120
ccctgcttta cttctaatga cggttctaat tctccacaat aaccctatga gacaggtgct     180
atcattgtct tattttaggg atggaaaagg gagggtgggg gggtgaggac acggcagagg     240
tgggatatgc attcttgcaa tctagatccg cagccctgtt agtccctag tggccttgtg      300 ggcttctctg ataaccggct cagttggggg atgagggctc gggggtagat tcccggcttc     360
cgaagaggcg tgagaattct gttcccccac atcaccgcgt cctttcttct gcccgatttc     420
cccggaaagt gtagcagagg cgctgtgttt ggaagtcccg ctatcacggc ccccagatg      480 gggcctggac gatgcctcct gacggccttg ttgcttctgg ccctggcgcc accgccggaa     540
gcctcccagt actgcggccg ccttgaatac tggaacccag acaacaagtg ctgcagcagc     600
tgcctgcaac gcttcgggcc gccccctgc ccggactatg agttccggga aaactgcgga     660
```

```
ctcaatgacc acggcgattt cgtaacgccc ccgttccgaa agtgttcttc tgggcagtgc      720
aaccccgacg gcgcggagct atgtagcccc tgcggcggcg gagccgtgac ccctactccc      780
gccgcgggcg ggggcagaac cccgtggcgc tgcagagaga ggccggtccc tgccaagggg      840
cactgccccc tcacacctgg aaacccaggc gccctagct cccaggagcg cagctcacca       900
gcaagttcca ttgcctggag gacccctgag cctgtccctc agcaggcctg gccgaatttc      960
cttccgctcg tggtgctggt cctgctcctg accttggcgg tgatagcgat cctcctgttt     1020
attctgctct ggcatctctg ctggcccaag gagaaagccg acccctatcc ctatcctggc     1080
ttggtctgcg gagtccccaa cacccacacc ccttcctcct cgcatctgtc ctccccaggc     1140
gccctggaga caggggacac atggaaggag gcctcactac ttccactcct gagcagggaa     1200
ctgtccagtc tggcgtcaca accctgtct cgcctcctgg atgagctgga ggtgctggaa      1260
gagctgattg tactgctgga ccctgagcct gggccaggtg ggggtatggc ccatggcact     1320
actcgacacc tggccgcaag atatgggctg cctgctgcct ggtccacctt tgcctattcg     1380
ctgaggccga gtcgctcgcc gctgcgggct ctgattgaga tggtggtggc aagggagccc     1440
tctgcctccc tgggccagct tggcacacac ctcgcccagc tagggcgggc agatgcattg     1500
cgggtgctgt ccaagcttgg ctcatctggg gtttgctggg cttaacaccc aataaagaac     1560
tttgctgact actaagccca gtatacaatt agcactgaag tacttcttga agtacaatcc     1620
taattgggca agacccaac agatagcctc actgctcttc gccctaga                   1668

<210> SEQ ID NO 2
<211> LENGTH: 355
<212> TYPE: PRT
<213> ORGANISM: Homo sapiens

<400> SEQUENCE: 2

Met Gly Pro Gly Arg Cys Leu Leu Thr Ala Leu Leu Leu Ala Leu
1               5                   10                  15

Ala Pro Pro Pro Glu Ala Ser Gln Tyr Cys Gly Arg Leu Glu Tyr Trp
                20                  25                  30

Asn Pro Asp Asn Lys Cys Cys Ser Cys Leu Gln Arg Phe Gly Pro
            35                  40                  45

Pro Pro Cys Pro Asp Tyr Glu Phe Arg Glu Asn Cys Gly Leu Asn Asp
        50                  55                  60

His Gly Asp Phe Val Thr Pro Pro Phe Arg Lys Cys Ser Ser Gly Gln
65                  70                  75                  80

Cys Asn Pro Asp Gly Ala Glu Leu Cys Ser Pro Cys Gly Gly Gly Ala
                85                  90                  95

Val Thr Pro Thr Pro Ala Ala Gly Gly Arg Thr Pro Trp Arg Cys
                100                 105                 110

Arg Glu Arg Pro Val Pro Ala Lys Gly His Cys Pro Leu Thr Pro Gly
            115                 120                 125

Asn Pro Gly Ala Pro Ser Ser Gln Glu Arg Ser Ser Pro Ala Ser Ser
        130                 135                 140

Ile Ala Trp Arg Thr Pro Glu Pro Val Pro Gln Gln Ala Trp Pro Asn
145                 150                 155                 160

Phe Leu Pro Leu Val Val Leu Val Leu Leu Thr Leu Ala Val Ile
                165                 170                 175

Ala Ile Leu Leu Phe Ile Leu Leu Trp His Leu Cys Trp Pro Lys Glu
            180                 185                 190

Lys Ala Asp Pro Tyr Pro Tyr Pro Gly Leu Val Cys Gly Val Pro Asn
```

```
                195                 200                 205
Thr His Thr Pro Ser Ser His Leu Ser Ser Pro Gly Ala Leu Glu
    210                 215                 220

Thr Gly Asp Thr Trp Lys Glu Ala Ser Leu Leu Pro Leu Leu Ser Arg
225                 230                 235                 240

Glu Leu Ser Ser Leu Ala Ser Gln Pro Leu Ser Arg Leu Leu Asp Glu
                245                 250                 255

Leu Glu Val Leu Glu Glu Leu Ile Val Leu Leu Asp Pro Glu Pro Gly
            260                 265                 270

Pro Gly Gly Gly Met Ala His Gly Thr Thr Arg His Leu Ala Ala Arg
        275                 280                 285

Tyr Gly Leu Pro Ala Ala Trp Ser Thr Phe Ala Tyr Ser Leu Arg Pro
    290                 295                 300

Ser Arg Ser Pro Leu Arg Ala Leu Ile Glu Met Val Val Ala Arg Glu
305                 310                 315                 320

Pro Ser Ala Ser Leu Gly Gln Leu Gly Thr His Leu Ala Gln Leu Gly
                325                 330                 335

Arg Ala Asp Ala Leu Arg Val Leu Ser Lys Leu Gly Ser Ser Gly Val
            340                 345                 350

Cys Trp Ala
        355

<210> SEQ ID NO 3
<211> LENGTH: 1525
<212> TYPE: DNA
<213> ORGANISM: Homo sapiens

<400> SEQUENCE: 3
gtaaagatgg ggtttcattt tgttgtccag gctgatctct cgaactcctg ggctcaagtg      60
atcctcctgt cttggcctcc caaagtgttg ggattacagg catgagccac cacacccagc     120
ccctgcttta cttctaatga cggttctaat tctccacaat aaccctatga cacaggtgct     180
atcattgtct tattttaggg atggaaaagg gagggtgggt gggtgaggac acggcagagg     240
tgggatatgc attcttgcaa tctagatccg cagccctgtt agtcccctag tggccttgtg     300
ggcttctctg ataaccggct cagttggggg atgagggctc gggggtagat tcccggcttc     360
cgaagaggcg tgagaattct gttcccccac atcaccgcgt cctttcttct gcccgatttc     420
cccggaaagt gtagcagagg cgctgtgttt ggaagtcccg ctatcacggc ccccagatg      480
gggcctggac gatgcctcct gacggccttg ttgcttctgg ccctggcgcc accgccggaa     540
gcctcccagt actgcggccg ccttgaatac tggaacccag acaacaagtg ctgcagcagc     600
tgcctgcaac gcttcgggcc gccccctgc ccgggtgaga atccgagacc gagccttgct     660
tgggcggagc ttgcagaggc cggtccctgc caagggcac tgccccctca cctggaaa       720
cccaggcgcc cctagctccc aggagcgcag ctcaccagca gttccattg cctggaggac      780
ccctgagcct gtccctcagc aggcctggcc gaatttcctt ccgctcgtgg tgctggtcct     840
gctcctgacc ttggcggtga tagcgatcct cctgtttatt ctgctctggc atctctgctg     900
gcccaaggag aaagccgacc ctatccccta tcctggcttg gtctgcggag tccccaacac     960
ccacaccccct tcctcctcgc atctgtcctc cccaggcgcc ctggagacag ggacacatg   1020
gaaggaggcc tcactacttc cactcctgag cagggaactg tccagtctgg cgtcacaacc   1080
cctgtctcgc ctcctggatg agctggaggt gctggaagag ctgattgtac tgctggaccc   1140
tgagcctggg ccaggtgggg gtatggccca tggcactact cgacacctgg ccgcaagata   1200
```

```
tgggctgcct gctgcctggt ccacctttgc ctattcgctg aggccgagtc gctcgccgct    1260
gcgggctctg attgagatgg tggtggcaag ggagccctct gcctccctgg gccagcttgg    1320
cacacacctc gcccagctag ggcgggcaga tgcattgcgg gtgctgtcca agcttggctc    1380
atctggggtt tgctgggctt aacacccaat aaagaacttt gctgactact aagcccagta    1440
tacaattagc actgaagtac ttcttgaagt acaatcctaa ttgggcaaag acccaacaga    1500
tagcctcact gctcttcgcc ctaga                                          1525

<210> SEQ ID NO 4
<211> LENGTH: 85
<212> TYPE: PRT
<213> ORGANISM: Homo sapiens

<400> SEQUENCE: 4

Met Gly Pro Gly Arg Cys Leu Leu Thr Ala Leu Leu Leu Ala Leu
1               5                   10                  15

Ala Pro Pro Glu Ala Ser Gln Tyr Cys Gly Arg Leu Glu Tyr Trp
            20                  25                  30

Asn Pro Asp Asn Lys Cys Cys Ser Ser Cys Leu Gln Arg Phe Gly Pro
        35                  40                  45

Pro Pro Cys Pro Gly Glu Asn Pro Arg Pro Ser Leu Ala Trp Ala Glu
    50                  55                  60

Leu Ala Glu Ala Gly Pro Cys Gln Gly Ala Leu Pro Pro His Thr Trp
65                  70                  75                  80

Lys Pro Arg Arg Pro
                85

<210> SEQ ID NO 5
<211> LENGTH: 1289
<212> TYPE: DNA
<213> ORGANISM: Homo sapiens

<400> SEQUENCE: 5
gtaaagatgg ggtttcattt tgttgtccag gctgatctct cgaactcctg ggctcaagtg      60
atcctcctgt cttggcctcc caaagtgttg ggattacagg catgagccac cacacccagc     120
ccctgcttta cttctaatga cggttctaat tctccacaat aaccctatga gacaggtgct     180
atcattgtct tattttaggg atggaaaagg gagggtgggt gggtgaggac acggcagagg     240
tgggatatgc attcttgcaa tctagatccg cagccctgtt agtcccctag tggccttgtg     300
ggcttctctg ataaccggct cagttggggg atgagggctc gggggtagat tcccggcttc     360
cgaagaggcg tgagaattct gttcccccac atcaccgcgt cctttcttct gcccgatttc     420
cccggaaagt gtagcagagg cgctgtgttt ggaagtcccg ctatcacggc ccccagatg      480 gggcctggac gatgcctcct gacggccttg ttgcttctgg ccctggcgcc accgccggaa     540
gcctcccagt actgcggccg ccttgaatac tggaacccag acaacaagtg ctgcagcagc     600
tgcctgcaac gttcgggcc gccccctgc ccggactatg agttccggga aaactgcgga     660
ctcaatgacc acggcgattt cgtaacgccc ccgttccgaa agtgttcttc tgggcagtgc     720
aaccccgacg cgcgcgagct atgtagcccc tgcggcggcg agccgtgac ccctactccc     780 gccgcgggcg ggggcagaac cccgtggcgc tgcagagaga actgtccagt ctggcgtcac     840 aaccctgtc tcgcctcctg gatgagctgg aggtgctgga agagctgatt gtactgctgg     900
accctgagcc tgggccaggt gggggtatgg cccatggcac tactcgacac ctggccgcaa     960
```

-continued

```
gatatgggct gcctgctgcc tggtccacct ttgcctattc gctgaggccg agtcgctcgc    1020
cgctgcgggc tctgattgag atggtggtgg caagggagcc ctctgcctcc ctgggccagc    1080
ttggcacaca cctcgcccag ctagggcggg cagatgcatt gcgggtgctg tccaagcttg    1140
gctcatctgg ggtttgctgg gcttaacacc caataaagaa ctttgctgac tactaagccc    1200
agtatacaat tagcactgaa gtacttcttg aagtacaatc ctaattgggc aaagacccaa    1260
cagatagcct cactgctctt cgccctaga                                      1289
```

<210> SEQ ID NO 6
<211> LENGTH: 136
<212> TYPE: PRT
<213> ORGANISM: Homo sapiens

<400> SEQUENCE: 6

```
Met Gly Pro Gly Arg Cys Leu Leu Thr Ala Leu Leu Leu Ala Leu
1               5                  10                  15

Ala Pro Pro Pro Glu Ala Ser Gln Tyr Cys Gly Arg Leu Glu Tyr Trp
                20                  25                  30

Asn Pro Asp Asn Lys Cys Cys Ser Ser Cys Leu Gln Arg Phe Gly Pro
            35                  40                  45

Pro Pro Cys Pro Asp Tyr Glu Phe Arg Glu Asn Cys Gly Leu Asn Asp
        50                  55                  60

His Gly Asp Phe Val Thr Pro Pro Phe Arg Lys Cys Ser Ser Gly Gln
65                  70                  75                  80

Cys Asn Pro Asp Gly Ala Glu Leu Cys Ser Pro Cys Gly Gly Gly Ala
                85                  90                  95

Val Thr Pro Thr Pro Ala Ala Gly Gly Gly Arg Thr Pro Trp Arg Cys
                100                 105                 110

Arg Glu Asn Cys Pro Val Trp Arg His Asn Pro Cys Leu Ala Ser Trp
            115                 120                 125

Met Ser Trp Arg Cys Trp Lys Ser
        130                 135
```

<210> SEQ ID NO 7
<211> LENGTH: 1164
<212> TYPE: DNA
<213> ORGANISM: Homo sapiens

<400> SEQUENCE: 7

```
gtaaagatgg ggtttcattt tgttgtccag gctgatctct cgaactcctg ggctcaagtg     60
atcctcctgt cttggcctcc caaagtgttg ggattacagg catgagccac cacacccagc    120
ccctgcttta cttctaatga cggttctaat tctccacaat aaccctatga dacaggtgct    180
atcattgtct tattttaggg atggaaaagg gagggtgggt gggtgaggac acggcagagg    240
tgggatatgc attcttgcaa tctagatccg cagccctgtt agtcccctag tggccttgtg    300
ggcttctctg ataaccggct cagttggggg atgagggctc gggggtagat tcccggcttc    360
cgaagaggcg tgagaattct gttcccccac atcaccgcgt cctttcttct gcccgatttc    420
cccggaaagt gtagcagagg cgctgtgttt ggaagtcccg ctatcacggc cccccagatg    480
gggcctggac gatgcctcct gacgccttg ttgcttctgg ccctggcgcc accgccggaa    540
gcctcccagt actgcggccg ccttgaatac tggaacccag acaacaagtg ctgcagcagc    600
tgcctgcaac gcttcgggcc gccccctgc ccggcgccc tggagacagg gacacatgg    660 aaggaggcct cactacttcc actcctgagc agggaactgt ccagtctggc gtcacaaccc    720
```

```
ctgtctcgcc tcctggatga gctggaggtg ctggaagagc tgattgtact gctggaccct      780
gagcctgggc caggtggggg tatggcccat ggcactactc gacacctggc cgcaagatat      840
gggctgcctg ctgcctggtc cacctttgcc tattcgctga ggccgagtcg ctcgccgctg      900
cgggctctga ttgagatggt ggtggcaagg gagccctctg cctccctggg ccagcttggc      960
acacacctcg cccagctagg gcgggcagat gcattgcggg tgctgtccaa gcttggctca     1020
tctggggttt gctgggctta acacccaata aagaactttg ctgactacta agcccagtat     1080
acaattagca ctgaagtact tcttgaagta caatcctaat tgggcaaaga cccaacagat     1140
agcctcactg ctcttcgccc taga                                            1164
```

<210> SEQ ID NO 8
<211> LENGTH: 187
<212> TYPE: PRT
<213> ORGANISM: Homo sapiens

<400> SEQUENCE: 8

```
Met Gly Pro Gly Arg Cys Leu Leu Thr Ala Leu Leu Leu Leu Ala Leu
1               5                   10                  15

Ala Pro Pro Pro Glu Ala Ser Gln Tyr Cys Gly Arg Leu Glu Tyr Trp
            20                  25                  30

Asn Pro Asp Asn Lys Cys Cys Ser Ser Cys Leu Gln Arg Phe Gly Pro
        35                  40                  45

Pro Pro Cys Pro Gly Ala Leu Glu Thr Gly Asp Thr Trp Lys Glu Ala
    50                  55                  60

Ser Leu Leu Pro Leu Leu Ser Arg Glu Leu Ser Ser Leu Ala Ser Gln
65                  70                  75                  80

Pro Leu Ser Arg Leu Leu Asp Glu Leu Glu Val Leu Glu Glu Leu Ile
                85                  90                  95

Val Leu Leu Asp Pro Glu Pro Gly Pro Gly Gly Met Ala His Gly
            100                 105                 110

Thr Thr Arg His Leu Ala Ala Arg Tyr Gly Leu Pro Ala Ala Trp Ser
        115                 120                 125

Thr Phe Ala Tyr Ser Leu Arg Pro Ser Arg Ser Pro Leu Arg Ala Leu
    130                 135                 140

Ile Glu Met Val Val Ala Arg Glu Pro Ser Ala Ser Leu Gly Gln Leu
145                 150                 155                 160

Gly Thr His Leu Ala Gln Leu Gly Arg Ala Asp Ala Leu Arg Val Leu
                165                 170                 175

Ser Lys Leu Gly Ser Ser Gly Val Cys Trp Ala
            180                 185
```

<210> SEQ ID NO 9
<211> LENGTH: 1483
<212> TYPE: DNA
<213> ORGANISM: Homo sapiens

<400> SEQUENCE: 9

```
gtaaagatgg ggtttcattt tgttgtccag gctgatctct cgaactcctg ggctcaagtg       60
atcctcctgt cttggcctcc caaagtgttg ggattacagg catgagccac cacacccagc      120
ccctgcttta cttctaatga cggttctaat tctccacaat aacccctatga gacaggtgct      180 atcattgtct tattttaggg atggaaaagg gagggtgggt gggtgaggac acggcagagg      240
tgggatatgc attcttgcaa tctagatccg cagccctgtt agtcccctag tggccttgtg      300
ggcttctctg ataaccggct cagttggggg atgagggctc gggggtagat tcccggcttc      360
```

```
cgaagaggcg tgagaattct gttcccccac atcaccgcgt cctttcttct gcccgatttc    420
cccggaaagt gtagcagagg cgctgtgttt ggaagtcccg ctatcacggc ccccagatg     480 gggcctggac gatgcctcct gacgccttg ttgcttctgg ccctggcgcc accgccggaa    540
gcctcccagt actgcggccg ccttgaatac tggaacccag acaacaagtg ctgcagcagc    600
tgcctgcaac gcttcgggcc gccccctgc cggaggccg gtccctgcca agggcactg      660 ccccctcaca cctggaaacc caggcgcccc tagctcccag gagcgcagct caccagcaag    720
ttccattgcc tggaggaccc ctgagcctgt ccctcagcag gctggccga atttccttcc    780 gctcgtggtg ctggtcctgc tcctgacctt ggcggtgata gcgatcctcc tgtttattct    840
gctctggcat ctctgctggc caaggagaa agccgacccc tatccctatc ctggcttggt    900
ctgcggagtc cccaacaccc acacccctc ctcctcgcat ctgtcctccc caggcgccct     960
ggagacaggg gacacatgga aggaggcctc actacttcca ctcctgagca ggaactgtc    1020 cagtctggcg tcacaacccc tgtctcgcct cctggatgag ctggaggtgc tggaagagct   1080
gattgtactg ctggaccctg agcctgggcc aggtggggt atggcccatg cactactcg    1140 acacctggcc gcaagatatg ggctgcctgc tgcctggtcc acctttgcct attcgctgag   1200
gccgagtcgc tcgccgctgc gggctctgat tgagatggtg gtggcaaggg agccctctgc   1260
ctccctgggc cagcttggca cacacctcgc ccagctaggg cgggcagatg cattgcgggt   1320
gctgtccaag cttggctcat ctggggtttg ctgggcttaa cacccaataa agaactttgc   1380
tgactactaa gcccagtata caattagcac tgaagtactc cttgaagtac aatcctaatt   1440
gggcaaagac ccaacagata gcctcactgc tcttcgccct aga                    1483

<210> SEQ ID NO 10
<211> LENGTH: 71
<212> TYPE: PRT
<213> ORGANISM: Homo sapiens

<400> SEQUENCE: 10

Met Gly Pro Gly Arg Cys Leu Leu Thr Ala Leu Leu Leu Ala Leu
1               5                   10                  15

Ala Pro Pro Pro Glu Ala Ser Gln Tyr Cys Gly Arg Leu Glu Tyr Trp
                20                  25                  30

Asn Pro Asp Asn Lys Cys Cys Ser Ser Cys Leu Gln Arg Phe Gly Pro
            35                  40                  45

Pro Pro Cys Pro Glu Ala Gly Pro Cys Gln Gly Ala Leu Pro Pro His
        50                  55                  60

Thr Trp Lys Pro Arg Arg Pro
65                  70

<210> SEQ ID NO 11
<211> LENGTH: 1104
<212> TYPE: DNA
<213> ORGANISM: Homo sapiens

<400> SEQUENCE: 11
gtaaagatgg ggtttcattt tgttgtccag gctgatctct cgaactcctg ggctcaagtg    60
atcctcctgt cttggcctcc caaagtgttg ggattacagg catgagccac cacacccagc   120
ccctgcttta cttctaatga cggttctaat tctccacaat aacccatga gacaggtgct     180 atcattgtct tatttagggg atggaaaagg gagggtgggt gggtgaggac acggcagagg   240
tgggatatgc attcttgcaa tctagatccg cagccctgtt agtcccctag tggccttgtg   300
```

```
ggcttctctg ataaccggct cagttggggg atgagggctc gggggtagat tcccggcttc      360
cgaagaggcg tgagaattct gttccccac atcaccgcgt cctttcttct gcccgatttc       420
cccggaaagt gtagcagagg cgctgtgttt ggaagtcccg ctatcacggc cccccagatg      480
gggcctggac gatgcctcct gacggccttg ttgcttctgg ccctggcgcc accgccggaa      540
gcctcccagt actgcggccg ccttgaatac tggaacccag acaacaagtg ctgcagcagc      600
tgcctgcaac gcttcgggcc gccccctgc ccggaactgt ccagtctggc gtcacaaccc       660
ctgtctcgcc tcctggatga gctggaggtg ctggaagagc tgattgtact gctggaccct     720
gagcctgggc caggtggggg tatggcccat ggcactactc gacacctggc cgcaagatat      780
gggctgcctg ctgcctggtc cacctttgcc tattcgctga gccgagtcg ctcgccgctg       840 cgggctctga ttgagatggt ggtggcaagg gagccctctg cctccctggg ccagcttggc      900
acacacctcg cccagctagg gcgggcagat gcattgcggg tgctgtccaa gcttggctca      960 tctgggggttt gctgggctta acacccaata aagaactttg ctgactacta agcccagtat    1020
acaattagca ctgaagtact tcttgaagta caatcctaat tgggcaaaga cccaacagat     1080
agcctcactg ctcttcgccc taga                                             1104
```

<210> SEQ ID NO 12
<211> LENGTH: 167
<212> TYPE: PRT
<213> ORGANISM: Homo sapiens

<400> SEQUENCE: 12

```
Met Gly Pro Gly Arg Cys Leu Leu Thr Ala Leu Leu Leu Ala Leu
1               5                   10                  15

Ala Pro Pro Pro Glu Ala Ser Gln Tyr Cys Gly Arg Leu Glu Tyr Trp
                20                  25                  30

Asn Pro Asp Asn Lys Cys Cys Ser Ser Cys Leu Gln Arg Phe Gly Pro
            35                  40                  45

Pro Pro Cys Pro Glu Leu Ser Ser Leu Ala Ser Gln Pro Leu Ser Arg
        50                  55                  60

Leu Leu Asp Glu Leu Glu Val Leu Glu Glu Leu Ile Val Leu Leu Asp
65                  70                  75                  80

Pro Glu Pro Gly Pro Gly Gly Gly Met Ala His Gly Thr Thr Arg His
                85                  90                  95

Leu Ala Ala Arg Tyr Gly Leu Pro Ala Ala Trp Ser Thr Phe Ala Tyr
                100                 105                 110

Ser Leu Arg Pro Ser Arg Ser Pro Leu Arg Ala Leu Ile Glu Met Val
            115                 120                 125

Val Ala Arg Glu Pro Ser Ala Ser Leu Gly Gln Leu Gly Thr His Leu
        130                 135                 140

Ala Gln Leu Gly Arg Ala Asp Ala Leu Arg Val Leu Ser Lys Leu Gly
145                 150                 155                 160

Ser Ser Gly Val Cys Trp Ala
                165
```

<210> SEQ ID NO 13
<211> LENGTH: 1202
<212> TYPE: DNA
<213> ORGANISM: Mus musculus

<400> SEQUENCE: 13

```
cggacgcgtg ggcggacgcg tgggtgggtc tgcactgaaa cagtgtgggt ggaagtggtc       60
```

```
acagccctca agctgcaggc tctgctgaga tggggcccag ctggcttctc tggacagtgg      120
cggtggcagt gctgctcctg acccgggctg cgtcaatgga agcctctagc ttctgtggcc      180
accttgagta ctggaactct gacaagaggt gctgcagccg ctgcctgcaa cgctttgggc      240
ctcctgcatg tcctgatcac gagttcacgg aaaactgcgg gctcaatgac ttcggcgata      300
ctgtagcaca tcctttcaaa aagtgttccc ctgggtattg caaccccaat ggcacagagc      360
tgtgtagcca gtgtagcagc ggagccgccg cagccccagc tcacgtggag agccctggta      420
gaacccacaa gcagtgtaga agaagcccg tccctcccaa ggatgtctgt cctcttaaac      480
ctgaagacgc aggtgcctct agctcacctg ggaggtggag ccttgggcag acaaccaaga      540
atgaggtctc cagccgacca ggttttgtct cagcctcagt gctgcctctg cagtgttgc       600 cactgttgct ggtgctgctt ctgatattgg cagtggtctt gctctctttg ttcaagagaa      660
aagtccgttc ccgtcctggt tccagctcag cttttggaga tcccagcacc tctctacatt      720
actggccctg cccaggtacc ctggaggtat tggaaagtag aaacagaggg aaagctaatc      780
tgctgcagct ctcaagctgg gagcttcagg gtctggcctc tcagccctc tccctcctgc       840 tggatgagct ggaagttctg gaggagctga ttatgctatt ggaccctgag cctgggccga      900 gcggagcac ggcttatggt accacacgac acctggctgc aagatacggg ctgcctgcca       960
cctggtctac cttcgcctac tcacttcggc ccagtcgctc accctgcgg gccctgattg       1020 agatggttgt ggcaagggag ccttctgcta ctctgggtca attcggcaca tatttggctc      1080
agctaggtcg cacagatgct ctgcaggtgc tatctaaact tggctgagtc agagtttgct      1140
ggggcttact actccatcaa taaagtttcc cttgaagcca aaaaaaaaaa aaaaaaaaa       1200 aa                                                                     1202
```

<210> SEQ ID NO 14
<211> LENGTH: 345
<212> TYPE: PRT
<213> ORGANISM: Mus musculus

<400> SEQUENCE: 14

```
Met Gly Pro Ser Trp Leu Leu Trp Thr Val Ala Val Ala Val Leu Leu
1               5                   10                  15

Leu Thr Arg Ala Ala Ser Met Glu Ala Ser Ser Phe Cys Gly His Leu
            20                  25                  30

Glu Tyr Trp Asn Ser Asp Lys Arg Cys Cys Ser Arg Cys Leu Gln Arg
        35                  40                  45

Phe Gly Pro Pro Ala Cys Pro Asp His Glu Phe Thr Glu Asn Cys Gly
    50                  55                  60

Leu Asn Asp Phe Gly Asp Thr Val Ala His Pro Phe Lys Lys Cys Ser
65                  70                  75                  80

Pro Gly Tyr Cys Asn Pro Asn Gly Thr Glu Leu Cys Ser Gln Cys Ser
                85                  90                  95

Ser Gly Ala Ala Ala Ala Pro Ala His Val Glu Ser Pro Gly Arg Thr
            100                 105                 110

His Lys Gln Cys Arg Lys Lys Pro Val Pro Pro Lys Asp Val Cys Pro
        115                 120                 125

Leu Lys Pro Glu Asp Ala Gly Ala Ser Ser Ser Pro Gly Arg Trp Ser
    130                 135                 140

Leu Gly Gln Thr Thr Lys Asn Glu Val Ser Ser Arg Pro Gly Phe Val
145                 150                 155                 160
```

```
Ser Ala Ser Val Leu Pro Leu Ala Val Leu Pro Leu Leu Val Leu
            165                 170                 175
Leu Leu Ile Leu Ala Val Val Leu Leu Ser Leu Phe Lys Arg Lys Val
        180                 185                 190
Arg Ser Arg Pro Gly Ser Ser Ala Phe Gly Asp Pro Ser Thr Ser
        195                 200                 205
Leu His Tyr Trp Pro Cys Pro Gly Thr Leu Glu Val Leu Glu Ser Arg
210                 215                 220
Asn Arg Gly Lys Ala Asn Leu Leu Gln Leu Ser Ser Trp Glu Leu Gln
225                 230                 235                 240
Gly Leu Ala Ser Gln Pro Leu Ser Leu Leu Leu Asp Glu Leu Glu Val
                245                 250                 255
Leu Glu Glu Leu Ile Met Leu Leu Asp Pro Glu Pro Gly Pro Ser Gly
            260                 265                 270
Ser Thr Ala Tyr Gly Thr Thr Arg His Leu Ala Ala Arg Tyr Gly Leu
        275                 280                 285
Pro Ala Thr Trp Ser Thr Phe Ala Tyr Ser Leu Arg Pro Ser Arg Ser
    290                 295                 300
Pro Leu Arg Ala Leu Ile Glu Met Val Val Ala Arg Glu Pro Ser Ala
305                 310                 315                 320
Thr Leu Gly Gln Phe Gly Thr Tyr Leu Ala Gln Leu Gly Arg Thr Asp
                325                 330                 335
Ala Leu Gln Val Leu Ser Lys Leu Gly
            340                 345

<210> SEQ ID NO 15
<211> LENGTH: 1229
<212> TYPE: DNA
<213> ORGANISM: Mus musculus

<400> SEQUENCE: 15
ccaccatggg gcccagctgg cttctctgga cagtggcggt ggcagtgctg ctcctgaccc     60
gggctgcgtc aatggaagcc tctagcttct gtggccacct tgagtactgg aactctgaca    120
agaggtgctg cagccgctgc ctgcaacgct ttgggcctcc tgcatgtcct gatcacgagt    180
tcacggaaaa ctgcgggctc aatgacttcg gcgatactgt agcacatcct ttcaaaaagt    240
gttcccctgg gtattgcaac cccaatggca cagagctgtg tagccagtgt agcagcggag    300
ccgccgcagc cccagctcac gtggagagcc ctggtagaac ccacaagcag tgtagaaaga    360
agcccgtccc tcccaaggat gtctgtcctc ttaaacctga agacgcaggt gcctctagct    420
cacctgggag gtggagcctt gggcagacaa ccaagaatga ggtcgcggcc gctcgtcgtg    480
catcagtaga gcccaaatct tgtgacaaaa ctcacacatg cccaccgtgc ccagcacctg    540
aactcctggg gggaccgtca gtcttcctct tccccccaaa acccaaggac accctcatga    600
tctcccggac ccctgaggtc acatgcgtgg tggtggacgt gagccacgaa gaccctgagg    660
tcaagttcaa ctggtacgtg gacggcgtgg aggtgcataa tgccaagaca agccgcggg    720
aggagcagta caacagcacg taccgtgtgg tcagcgtcct caccgtcctg caccaggact    780
ggctgaatgg caaggagtac aagtgcaagg tctccaacaa agccctccca gcccccatcg    840
agaaaaccat ctccaaagcc aaagggcagc ccgagaacc acaggtgtac accctgcccc    900
catcccggga tgagctgacc aagaaccagg tcagcctgac ctgcctggtc aaaggcttct    960
atccagcga catcgccgtg gagtgggaga gcaatgggca gccggagaac aactacaaga   1020
ccacgcctcc cgtgctggac tccgacggct ccttcttcct ctacagcaag ctcaccgtgg   1080
```

-continued

```
acaagagcag gtggcagcag gggaacgtct tctcatgctc cgtgatgcat gaggctctgc   1140
acaaccacta cacgcagaag agcctctccc tgtctccggg taaaagaaga gctagtctcc   1200
atcatcatca tcatcattga taagtcgac                                    1229
```

<210> SEQ ID NO 16
<211> LENGTH: 404
<212> TYPE: PRT
<213> ORGANISM: Mus musculus

<400> SEQUENCE: 16

```
Met Gly Pro Ser Trp Leu Leu Trp Thr Val Ala Val Ala Val Leu Leu
1               5                   10                  15

Leu Thr Arg Ala Ala Ser Met Glu Ala Ser Ser Phe Cys Gly His Leu
            20                  25                  30

Glu Tyr Trp Asn Ser Asp Lys Arg Cys Cys Ser Arg Cys Leu Gln Arg
        35                  40                  45

Phe Gly Pro Pro Ala Cys Pro Asp His Glu Phe Thr Glu Asn Cys Gly
    50                  55                  60

Leu Asn Asp Phe Gly Asp Thr Val Ala His Pro Phe Lys Lys Cys Ser
65                  70                  75                  80

Pro Gly Tyr Cys Asn Pro Asn Gly Thr Glu Leu Cys Ser Gln Cys Ser
                85                  90                  95

Ser Gly Ala Ala Ala Ala Pro Ala His Val Glu Ser Pro Gly Arg Thr
            100                 105                 110

His Lys Gln Cys Arg Lys Lys Pro Val Pro Lys Asp Val Cys Pro
        115                 120                 125

Leu Lys Pro Glu Asp Ala Gly Ala Ser Ser Pro Gly Arg Trp Ser
    130                 135                 140

Leu Gly Gln Thr Thr Lys Asn Glu Val Ala Ala Arg Arg Ala Ser
145                 150                 155                 160

Val Glu Pro Lys Ser Cys Asp Lys Thr His Thr Cys Pro Pro Cys Pro
                165                 170                 175

Ala Pro Glu Leu Leu Gly Gly Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser His Glu Asp Pro Glu Val Lys Phe Asn Trp Tyr
    210                 215                 220

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
                245                 250                 255

Gln Asp Trp Leu Asn Gly Lys Glu Tyr Lys Cys Lys Val Ser Asn Lys
            260                 265                 270

Ala Leu Pro Ala Pro Ile Glu Lys Thr Ile Ser Lys Ala Lys Gly Gln
        275                 280                 285

Pro Arg Glu Pro Gln Val Tyr Thr Leu Pro Pro Ser Arg Asp Glu Leu
    290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Lys Thr Thr Pro Pro Val Leu Asp Ser Asp Gly Ser Phe Phe Leu
```

```
                   340                 345                 350
Tyr Ser Lys Leu Thr Val Asp Lys Ser Arg Trp Gln Gln Gly Asn Val
            355                 360                 365

Phe Ser Cys Ser Val Met His Glu Ala Leu His Asn His Tyr Thr Gln
        370                 375                 380

Lys Ser Leu Ser Leu Ser Pro Gly Lys Arg Arg Ala Ser Leu His His
385                 390                 395                 400

His His His His

<210> SEQ ID NO 17
<211> LENGTH: 110
<212> TYPE: PRT
<213> ORGANISM: Mus musculus

<400> SEQUENCE: 17

Met Ala Pro Arg Ala Arg Arg Arg Gln Leu Pro Ala Pro Leu Leu
1               5                   10                  15

Ala Leu Cys Val Leu Leu Val Pro Leu Gln Val Thr Leu Gln Val Thr
                20                  25                  30

Pro Pro Cys Thr Gln Glu Arg His Tyr Glu His Leu Gly Arg Cys Cys
            35                  40                  45

Ser Arg Cys Glu Pro Gly Lys Tyr Leu Ser Ser Lys Cys Thr Pro Thr
        50                  55                  60

Ser Asp Ser Val Cys Leu Pro Cys Gly Pro Asp Glu Tyr Leu Asp Thr
65                  70                  75                  80

Trp Asn Glu Glu Asp Lys Cys Leu Leu His Lys Val Cys Asp Ala Gly
                85                  90                  95

Lys Ala Leu Val Ala Val Asp Pro Gly Asn His Thr Ala Pro
            100                 105                 110

<210> SEQ ID NO 18
<211> LENGTH: 204
<212> TYPE: PRT
<213> ORGANISM: Mus musculus

<400> SEQUENCE: 18

Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
                20                  25                  30

Leu Arg Arg Arg Val His Glu Thr Asp Lys Asn Cys Ser Glu Gly Leu
            35                  40                  45

Tyr Gln Gly Gly Pro Phe Cys Cys Gln Pro Cys Gln Pro Gly Lys Lys
        50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160
```

```
Cys Arg Lys Gln Ser Pro Arg Asn Arg Leu Trp Leu Leu Thr Ile Leu
            165                 170                 175

Val Leu Leu Ile Pro Leu Val Phe Ile Tyr Arg Lys Tyr Arg Lys Arg
            180                 185                 190

Lys Cys Trp Lys Arg Arg Gln Asp Asp Pro Glu Ser
            195                 200
```

```
<210> SEQ ID NO 19
<211> LENGTH: 257
<212> TYPE: PRT
<213> ORGANISM: Mus musculus

<400> SEQUENCE: 19

Glu His Trp Asn Tyr Leu Thr Ile Cys Gln Leu Cys Arg Pro Cys Asp
1               5                   10                  15

Pro Val Met Gly Leu Glu Glu Ile Ala Pro Cys Thr Ser Lys Arg Lys
            20                  25                  30

Thr Gln Cys Arg Cys Gln Pro Gly Met Phe Cys Ala Ala Trp Ala Leu
        35                  40                  45

Glu Cys Thr His Cys Glu Leu Leu Ser Asp Cys Pro Pro Gly Thr Glu
    50                  55                  60

Ala Glu Leu Lys Asp Glu Val Gly Lys Gly Asn Asn His Cys Val Pro
65                  70                  75                  80

Cys Lys Ala Gly His Phe Gln Asn Thr Ser Ser Pro Ser Ala Arg Cys
                85                  90                  95

Gln Pro His Thr Arg Cys Glu Asn Gln Gly Leu Val Glu Ala Ala Pro
            100                 105                 110

Gly Thr Ala Gln Ser Asp Thr Thr Cys Lys Asn Pro Leu Glu Pro Leu
        115                 120                 125

Pro Pro Glu Met Ser Gly Thr Met Leu Met Leu Ala Val Leu Leu Pro
    130                 135                 140

Leu Ala Phe Phe Leu Leu Leu Ala Thr Val Phe Ser Cys Ile Trp Lys
145                 150                 155                 160

Ser His Pro Ser Leu Cys Arg Lys Leu Gly Ser Leu Leu Lys Arg Arg
                165                 170                 175

Pro Gln Gly Glu Gly Pro Asn Pro Val Ala Gly Ser Trp Glu Pro Pro
            180                 185                 190

Lys Ala His Pro Tyr Phe Pro Asp Leu Val Gln Pro Leu Leu Pro Ile
        195                 200                 205

Ser Gly Asp Val Ser Pro Val Ser Thr Gly Leu Pro Ala Ala Pro Val
    210                 215                 220

Leu Glu Ala Gly Val Pro Gln Gln Gln Ser Pro Leu Asp Leu Thr Arg
225                 230                 235                 240

Glu Pro Gln Leu Glu Pro Gly Glu Gln Ser Gln Val Ala His Gly Thr
                245                 250                 255

Asn
```

```
<210> SEQ ID NO 20
<211> LENGTH: 25
<212> TYPE: DNA
<213> ORGANISM: primer

<400> SEQUENCE: 20
ggtgaccacc tcgtgggcaa cgtct                                        25
```

```
<210> SEQ ID NO 21
<211> LENGTH: 25
<212> TYPE: DNA
<213> ORGANISM: primer

<400> SEQUENCE: 21
ggctcagggt ccagcagtac aatca                                       25

<210> SEQ ID NO 22
<211> LENGTH: 11
<212> TYPE: PRT
<213> ORGANISM: Peptide of HIV TAT protein

<400> SEQUENCE: 22

Tyr Gly Arg Lys Lys Arg Arg Gln Arg Arg Arg
1               5                   10

<210> SEQ ID NO 23
<211> LENGTH: 24
<212> TYPE: DNA
<213> ORGANISM: primer

<400> SEQUENCE: 23
cggacgcgtg ggcggacgcg tggg                                        24

<210> SEQ ID NO 24
<211> LENGTH: 24
<212> TYPE: DNA
<213> ORGANISM: primer

<400> SEQUENCE: 24
agcaaactct gactcagcca agtt                                        24

<210> SEQ ID NO 25
<211> LENGTH: 16
<212> TYPE: PRT
<213> ORGANISM: Homo sapiens

<400> SEQUENCE: 25

Met Glu Ala Ser Gln Gln Ala Trp Pro Asn His His His His His His
1               5                   10                  15

<210> SEQ ID NO 26
<211> LENGTH: 39
<212> TYPE: DNA
<213> ORGANISM: primer

<400> SEQUENCE: 26
gaggaataac atatggaagc ctctcagtat tgcggccgc                        39

<210> SEQ ID NO 27
<211> LENGTH: 54
<212> TYPE: DNA
<213> ORGANISM: primer

<400> SEQUENCE: 27
cggccgatcc tcgagttaat gatgatgatg atgatgattc ggccaggcct gctg        54

<210> SEQ ID NO 28
<211> LENGTH: 9
<212> TYPE: PRT
<213> ORGANISM: Homo sapiens

<400> SEQUENCE: 28
```

Met Glu Ala Ser Gln Ser Pro Gly Lys
1               5

<210> SEQ ID NO 29
<211> LENGTH: 14
<212> TYPE: PRT
<213> ORGANISM: Homo sapiens

<400> SEQUENCE: 29

Gln Ala Trp Pro Asn Gly Gly Gly Gly Asp Lys Thr His
1               5                   10

<210> SEQ ID NO 30
<211> LENGTH: 39
<212> TYPE: DNA
<213> ORGANISM: primer

<400> SEQUENCE: 30
gaggaataac atatggaagc ctctcagtat tgcggccgc                              39

<210> SEQ ID NO 31
<211> LENGTH: 51
<212> TYPE: DNA
<213> ORGANISM: primer

<400> SEQUENCE: 31
acatgtgtga gttttgtcac caccaccacc accattcggc caggcctgct g                51

<210> SEQ ID NO 32
<211> LENGTH: 51
<212> TYPE: DNA
<213> ORGANISM: primer

<400> SEQUENCE: 32
cagcaggcct ggccgaatgg tggtggtggt ggtgacaaaa ctcacacatg t                51

<210> SEQ ID NO 33
<211> LENGTH: 39
<212> TYPE: DNA
<213> ORGANISM: primer

<400> SEQUENCE: 33
ccgcggatcc tcgagttatt tacccggaga cagggagag                              39

<210> SEQ ID NO 34
<211> LENGTH: 39
<212> TYPE: DNA
<213> ORGANISM: primer

<400> SEQUENCE: 34
cagcccaagc tttagaccac catggggcct ggacgatgc                              39

<210> SEQ ID NO 35
<211> LENGTH: 24
<212> TYPE: DNA
<213> ORGANISM: primer

<400> SEQUENCE: 35
caggtcgaca ggctcagggg tcct                                              24

<210> SEQ ID NO 36
<211> LENGTH: 380
<212> TYPE: PRT
<213> ORGANISM: Homo sapiens

<400> SEQUENCE: 36

```
Met Gly Pro Gly Arg Cys Leu Leu Thr Ala Leu Leu Leu Leu Ala Leu
1               5                   10                  15

Ala Pro Pro Glu Ala Ser Gln Tyr Cys Gly Arg Leu Glu Tyr Trp
            20                  25                  30

Asn Pro Asp Asn Lys Cys Cys Ser Ser Cys Leu Gln Arg Phe Gly Pro
            35                  40                  45

Pro Pro Cys Pro Asp Tyr Glu Phe Arg Glu Asn Cys Gly Leu Asn Asp
        50                  55                  60

His Gly Asp Phe Val Thr Pro Pro Phe Arg Lys Cys Ser Ser Gly Gln
65                  70                  75                  80

Cys Asn Pro Asp Gly Ala Glu Leu Cys Ser Pro Cys Gly Gly Gly Ala
                85                  90                  95

Val Thr Pro Thr Pro Ala Ala Gly Gly Gly Arg Thr Pro Trp Arg Cys
            100                 105                 110

Arg Glu Arg Pro Val Pro Ala Lys Gly His Cys Pro Leu Thr Pro Gly
        115                 120                 125

Asn Pro Gly Ala Pro Ser Ser Gln Glu Arg Ser Ser Pro Ala Ser Ser
    130                 135                 140

Ile Ala Trp Arg Thr Pro Glu Pro Val Asp Lys Thr His Thr Cys Pro
145                 150                 155                 160

Pro Cys Pro Ala Pro Glu Leu Leu Gly Gly Pro Ser Val Phe Leu Phe
                165                 170                 175

Pro Pro Lys Pro Lys Asp Thr Leu Met Ile Ser Arg Thr Pro Glu Val
            180                 185                 190

Thr Cys Val Val Val Asp Val Ser His Glu Asp Pro Glu Val Lys Phe
        195                 200                 205

Asn Trp Tyr Val Asp Gly Val Glu Val His Asn Ala Lys Thr Lys Pro
    210                 215                 220

Arg Glu Glu Gln Tyr Asn Ser Thr Tyr Arg Val Val Ser Val Leu Thr
225                 230                 235                 240

Val Leu His Gln Asp Trp Leu Asn Gly Lys Glu Tyr Lys Cys Lys Val
                245                 250                 255

Ser Asn Lys Ala Leu Pro Ala Pro Ile Glu Lys Thr Ile Ser Lys Ala
            260                 265                 270

Lys Gly Gln Pro Arg Glu Pro Gln Val Tyr Thr Leu Pro Pro Ser Arg
        275                 280                 285

Asp Glu Leu Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Val Phe Ser Cys Ser Val Met His Glu Ala Leu His Asn His
        355                 360                 365

Tyr Thr Gln Lys Ser Leu Ser Leu Ser Pro Gly Lys
    370                 375                 380
```

<210> SEQ ID NO 37
<211> LENGTH: 39
<212> TYPE: DNA

```
-continued

<213> ORGANISM: primer

<400> SEQUENCE: 37
cagcccaagc tttagaccac catggggccc agctggctt                                      39

<210> SEQ ID NO 38
<211> LENGTH: 24
<212> TYPE: DNA
<213> ORGANISM: primer

<400> SEQUENCE: 38
caggtcgacc tcattcttgg ttgt                                                      24

<210> SEQ ID NO 39
<211> LENGTH: 380
<212> TYPE: PRT
<213> ORGANISM: Mus musculus

<400> SEQUENCE: 39
```

| Met | Gly | Pro | Ser | Trp | Leu | Leu | Trp | Thr | Val | Ala | Val | Ala | Val | Leu | Leu |
|---|---|---|---|---|---|---|---|---|---|---|---|---|---|---|---|
| 1 | | | | 5 | | | | | 10 | | | | | 15 | |

| Leu | Thr | Arg | Ala | Ala | Ser | Met | Glu | Ala | Ser | Ser | Phe | Cys | Gly | His | Leu |
|---|---|---|---|---|---|---|---|---|---|---|---|---|---|---|---|
| | | | 20 | | | | | 25 | | | | | 30 | | |

| Glu | Tyr | Trp | Asn | Ser | Asp | Lys | Arg | Cys | Cys | Ser | Arg | Cys | Leu | Gln | Arg |
|---|---|---|---|---|---|---|---|---|---|---|---|---|---|---|---|
| | | 35 | | | | | 40 | | | | | 45 | | | |

| Phe | Gly | Pro | Pro | Ala | Cys | Pro | Asp | His | Glu | Phe | Thr | Glu | Asn | Cys | Gly |
|---|---|---|---|---|---|---|---|---|---|---|---|---|---|---|---|
| | 50 | | | | | 55 | | | | | 60 | | | | |

| Leu | Asn | Asp | Phe | Gly | Asp | Thr | Val | Ala | His | Pro | Phe | Lys | Lys | Cys | Ser |
|---|---|---|---|---|---|---|---|---|---|---|---|---|---|---|---|
| 65 | | | | | 70 | | | | | 75 | | | | | 80 |

| Pro | Gly | Tyr | Cys | Asn | Pro | Asn | Gly | Thr | Glu | Leu | Cys | Ser | Gln | Cys | Ser |
|---|---|---|---|---|---|---|---|---|---|---|---|---|---|---|---|
| | | | | 85 | | | | | 90 | | | | | 95 | |

| Ser | Gly | Ala | Ala | Ala | Ala | Pro | Ala | His | Val | Glu | Ser | Pro | Gly | Arg | Thr |
|---|---|---|---|---|---|---|---|---|---|---|---|---|---|---|---|
| | | | 100 | | | | | 105 | | | | | 110 | | |

| His | Lys | Gln | Cys | Arg | Lys | Lys | Pro | Val | Pro | Pro | Lys | Asp | Val | Cys | Pro |
|---|---|---|---|---|---|---|---|---|---|---|---|---|---|---|---|
| | | 115 | | | | | 120 | | | | | 125 | | | |

| Leu | Lys | Pro | Glu | Asp | Ala | Gly | Ala | Ser | Ser | Ser | Pro | Gly | Arg | Trp | Ser |
|---|---|---|---|---|---|---|---|---|---|---|---|---|---|---|---|
| | 130 | | | | | 135 | | | | | 140 | | | | |

| Leu | Gly | Gln | Thr | Thr | Lys | Asn | Glu | Val | Asp | Lys | Thr | His | Thr | Cys | Pro |
|---|---|---|---|---|---|---|---|---|---|---|---|---|---|---|---|
| 145 | | | | | 150 | | | | | 155 | | | | | 160 |

| Pro | Cys | Pro | Ala | Pro | Glu | Leu | Leu | Gly | Gly | Pro | Ser | Val | Phe | Leu | Phe |
|---|---|---|---|---|---|---|---|---|---|---|---|---|---|---|---|
| | | | | 165 | | | | | 170 | | | | | 175 | |

| Pro | Pro | Lys | Pro | Lys | Asp | Thr | Leu | Met | Ile | Ser | Arg | Thr | Pro | Glu | Val |
|---|---|---|---|---|---|---|---|---|---|---|---|---|---|---|---|
| | | | 180 | | | | | 185 | | | | | 190 | | |

| Thr | Cys | Val | Val | Val | Asp | Val | Ser | His | Glu | Asp | Pro | Glu | Val | Lys | Phe |
|---|---|---|---|---|---|---|---|---|---|---|---|---|---|---|---|
| | | 195 | | | | | 200 | | | | | 205 | | | |

| Asn | Trp | Tyr | Val | Asp | Gly | Val | Glu | Val | His | Asn | Ala | Lys | Thr | Lys | Pro |
|---|---|---|---|---|---|---|---|---|---|---|---|---|---|---|---|
| | 210 | | | | | 215 | | | | | 220 | | | | |

| Arg | Glu | Glu | Gln | Tyr | Asn | Ser | Thr | Tyr | Arg | Val | Val | Ser | Val | Leu | Thr |
|---|---|---|---|---|---|---|---|---|---|---|---|---|---|---|---|
| 225 | | | | | 230 | | | | | 235 | | | | | 240 |

| Val | Leu | His | Gln | Asp | Trp | Leu | Asn | Gly | Lys | Glu | Tyr | Lys | Cys | Lys | Val |
|---|---|---|---|---|---|---|---|---|---|---|---|---|---|---|---|
| | | | | 245 | | | | | 250 | | | | | 255 | |

| Ser | Asn | Lys | Ala | Leu | Pro | Ala | Pro | Ile | Glu | Lys | Thr | Ile | Ser | Lys | Ala |
|---|---|---|---|---|---|---|---|---|---|---|---|---|---|---|---|
| | | | 260 | | | | | 265 | | | | | 270 | | |

| Lys | Gly | Gln | Pro | Arg | Glu | Pro | Gln | Val | Tyr | Thr | Leu | Pro | Pro | Ser | Arg |
|---|---|---|---|---|---|---|---|---|---|---|---|---|---|---|---|
| | | 275 | | | | | 280 | | | | | 285 | | | |

| Asp | Glu | Leu | Thr | Lys | Asn | Gln | Val | Ser | Leu | Thr | Cys | Leu | Val | Lys | Gly |
|---|---|---|---|---|---|---|---|---|---|---|---|---|---|---|---|

```
                290                 295                 300
Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Lys Leu Thr Val Asp Lys Ser Arg Trp Gln Gln
                340                 345                 350

Gly Asn Val Phe Ser Cys Ser Val Met His Glu Ala Leu His Asn His
                355                 360                 365

Tyr Thr Gln Lys Ser Leu Ser Leu Ser Pro Gly Lys
                370                 375                 380

<210> SEQ ID NO 40
<211> LENGTH: 26
<212> TYPE: DNA
<213> ORGANISM: primer

<400> SEQUENCE: 40
ttcccagttt ttcatctgca ctgcca                                        26

<210> SEQ ID NO 41
<211> LENGTH: 20
<212> TYPE: DNA
<213> ORGANISM: primer

<400> SEQUENCE: 41
tgctggaccc aacacaaatg                                               20

<210> SEQ ID NO 42
<211> LENGTH: 20
<212> TYPE: DNA
<213> ORGANISM: primer

<400> SEQUENCE: 42
tgccatccaa ccactcagtc                                               20

<210> SEQ ID NO 43
<211> LENGTH: 22
<212> TYPE: DNA
<213> ORGANISM: primer

<400> SEQUENCE: 43
ctgcctgctg cctggtccac ct                                            22

<210> SEQ ID NO 44
<211> LENGTH: 20
<212> TYPE: DNA
<213> ORGANISM: primer

<400> SEQUENCE: 44
acacctggcc gcaagatatg                                               20

<210> SEQ ID NO 45
<211> LENGTH: 20
<212> TYPE: DNA
<213> ORGANISM: primer

<400> SEQUENCE: 45
gactcggcct cagcgaatag                                               20
```